(12) United States Patent
Oikawa et al.

(10) Patent No.: US 7,375,170 B2
(45) Date of Patent: May 20, 2008

(54) ORGANOSILICON COMPOUND

(75) Inventors: Hisao Oikawa, Ichihara (JP); Mikio Yamahiro, Ichihara (JP); Koji Ohguma, Ichihara (JP); Nobumasa Ootake, Ichihara (JP); Kenichi Watanabe, Ichihara (JP); Kohji Ohno, Uji (JP); Yoshinobu Tsujii, Uji (JP); Takeshi Fukuda, Uji (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 318 days.

(21) Appl. No.: 11/316,847

(22) Filed: Dec. 27, 2005

(65) Prior Publication Data

US 2006/0175684 A1 Aug. 10, 2006

(30) Foreign Application Priority Data

Dec. 28, 2004 (JP) ............................. 2004-378486

(51) Int. Cl.
*C08F 4/58* (2006.01)
(52) U.S. Cl. .................... 526/194; 528/25; 528/31; 528/34; 528/37; 556/465; 556/479; 525/100; 525/106; 526/90
(58) Field of Classification Search ...................... None
See application file for complete search history.

(56) References Cited

U.S. PATENT DOCUMENTS

| | | | | |
|---|---|---|---|---|
| 7,169,873 | B2 * | 1/2007 | Morimoto et al. | 528/37 |
| 7,256,243 | B2 * | 8/2007 | Oikawa et al. | 526/126 |
| 7,294,732 | B2 * | 11/2007 | Ohno et al. | 556/428 |
| 2005/0009982 | A1 | 1/2005 | Inagaki et al. | |
| 2006/0094849 | A1 * | 5/2006 | Toyoda | 528/34 |
| 2006/0287454 | A1 * | 12/2006 | Yamahiro et al. | 526/279 |

FOREIGN PATENT DOCUMENTS

| EP | 1 428 795 | 6/2004 |
|---|---|---|
| JP | 2004-331647 | 11/2004 |

OTHER PUBLICATIONS

"Novel Inorganic-Organic Hybrid Block Copolymers as Pore Generators for Nanoporous Ultralow Dielectric Constant Films" authored by Yoon et al. and published in Macromolecules 2005, 38, 1031-1034.*
"Living Radical Polymerization by Polyhedral Oligomeric Silsesquioxane-Holding Initiators: Precision Synthesis of Tadpole-Shaped Organic/Inorganic Hybrid Polymers" authored by Fukuda et al and published in Macromolecules 2004, 37, 8517-8522.*
The abstract for an article entitled "Modified Cubic Spherosilicates as Macroinitiators for the Synthesis of Inorganic-Organic Starlike Polymers" authored by Holzinger et al. and published in the Journal of Polymer Science, Part A: Polymer Chemistry 2002, 40(21) 3858-3872.*

"Organic/Inorganic Nanocomposite star Polymers via Atom Transfer Radical Polymerization of Methyl Methacrylate Using Octafunctional Silsesquioxane Cores" authored by Laine et al. and published in Macromolecules 2001, 34, 5398-5407.*
Chunxin Zhang et al., "Hydrosilylation of Allyl Alcohol with [HSiMe$_2$OSiO$_{1.5}$]$_8$: Octa(3-hydroxypropyldimethylsiloxy) octasilsesquioxane and Its Octamethacrylate Derivative as Potential Precursors to Hybrid Nanocomposites", J. Am. Chem. Soc., 122, pp. 6979-6988, 2000.
Alan Sellinger et al., "Silsesquioxanes as Synthetic Platforms. 3. Photocurable, Liquid Epoxides as Inorganic/Organic Hybrid Precursors", Chemistry of Materials, 8, pp. 1592-1593, 1996.
Alan Sellinger et al., "Silsesquioxanes as Synthetic Platforms. Thermally Curable and Photocurable Inorganic/Organic Hybrids", Macromolecules, 29, pp. 2327-2330, 1996.
Krzysztof Matyjaszewski et al., "Atom Transfer Radical Polymerization", Chem. Rev., 101, pp. 2921-2990, 2001.
Frank J. Feher et al., "Enhanced Silylation Reactivity of a Model for Silica Surfaces", J. Am. Chem. Soc., 112, pp. 1931-1936, 1990.
A. Ramakrishnan et al., "Controlled Growth of PMMA Brushes on Silicon Surfaces at Room Temperature", Macromol. Rapid Commun., 23, No. 10/11, pp. 612-616, 2002.
Jin-Shan Wang et al., "Controlled/"Living" Radical Polymerization. Atom Transfer Radical Polymerization in the Presence of Transition-Metal Complexes", J. Am. Chem. Soc., 117, pp. 5614-5615, 1995.

(Continued)

*Primary Examiner*—Marc S. Zimmer
(74) *Attorney, Agent, or Firm*—Wenderoth, Lind & Ponack, L.L.P.

(57) ABSTRACT

Since the majority of conventional organic/inorganic composite materials are obtained by mechanical blending of a silsesquioxane and an organic polymer or other means, it was extremely difficult to control the structure of the composite as a molecular agglomerate. In order to solve such a problem, the invention is to provide a silicon compound represented by Formula (1). This novel silicon compound has a living radical polymerization initiating ability for addition polymerizable monomers of a wide range. In Formula (1), $R^1$ is hydrogen, an alkyl, an aryl, or an arylalkyl; $R^2$ is an alkyl, phenyl, or cyclohexyl; and A is a group having a polymerization initiating ability for addition polymerizable monomers

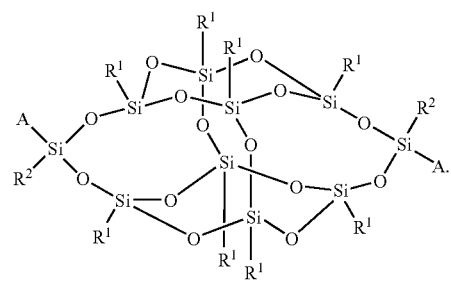

(1)

53 Claims, 2 Drawing Sheets

OTHER PUBLICATIONS

Jin-Shan Wang et al., "Controlled/"Living" Radical Polymerization. Halogen Atom Transfer Radical Polymerization Promoted by a Cu(I)/Cu(II) Redox Process", Macromolecules, 28, pp. 7901-7910, 1995.

Timothy E. Patten et al., "Polymers with Very Low Polydispersities from Atom Transfer Radical Polymerization", Science, vol. 272, pp. 866-869, May 10, 1996.

Takayuki Otsu et al., "Living Mono- and Biradical Polymerizations in Homogeneous System Synthesis of AB and ABA Type Block Copolymers", Polymer Bulletin, 11, pp. 135-142, 1984.

Takayuki Otsu, "Synthesis, Reactivity, and Role of 4-Vinylbenzyl N,N-Diethyldithiocarbamate as a Monomer-Iniferter in Radical Polymerization", Macromolecules, 19, pp. 287-290, 1986.

* cited by examiner

<Figure 1>
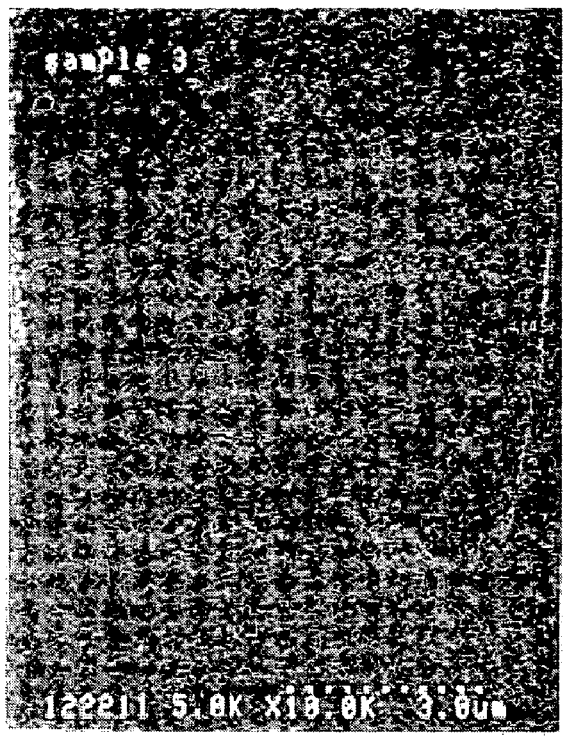
<Figure 2>
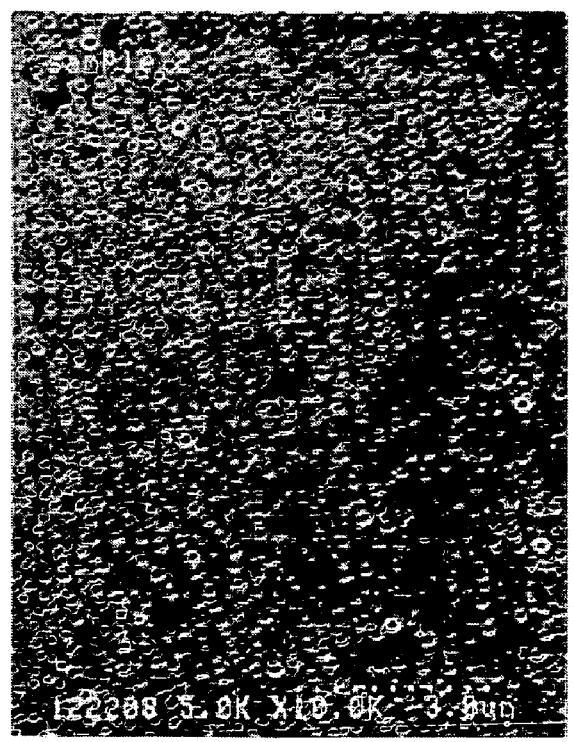

<Figure 3>
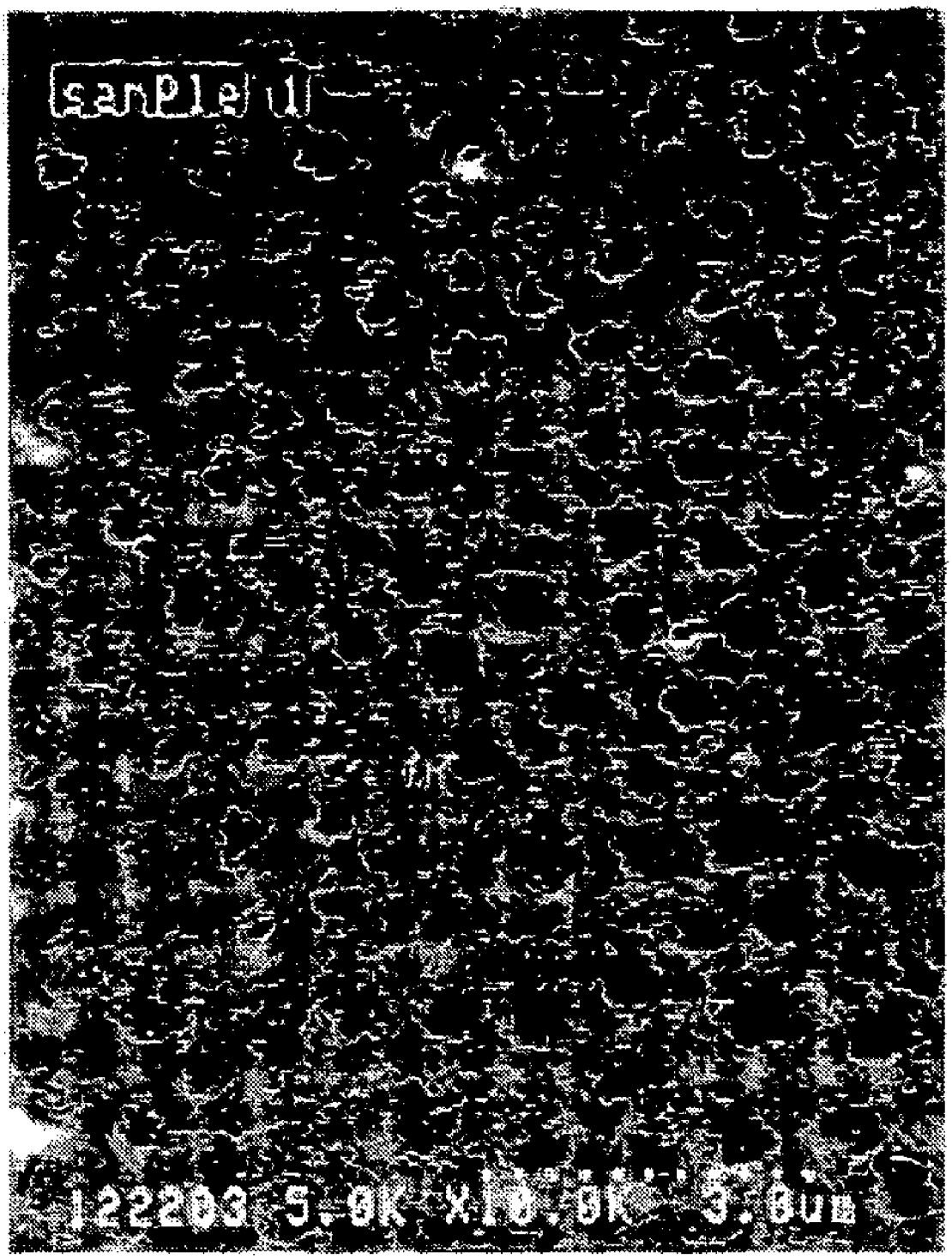

ORGANOSILICON COMPOUND

FIELD OF THE INVENTION

The present invention relates to a novel silicon compound which is characterized by having a polymerization initiating ability for addition polymerizable monomers, a process for producing the same, and a polymer obtained by using the same.

BACKGROUND OF THE INVENTION

Polymers have been utilized in various fields not only as general-purpose structure forming materials but also as high value added type materials having high function or performance. Following this, importance in manufacturing a polymer material on the basis of a precise design is increasing. Cage-type silsesquioxane derivatives having a dimethylsiloxane group are watched as an organic/inorganic composite material containing a silsesquioxane as an inorganic component. This is because they are expected to be utilized for precursors of organic/inorganic hybrid materials, low-dielectric materials, optical crystals, materials for forming a liquid crystal display element, and the like, and the reason for this resides in the matter that the silsesquioxane derivatives have a structure closed to silica or zeolite. Then, there are reported cage-type silsesquioxanes in which a hydroxyl group, an epoxy group or a methacryloyloxy group is bound to a dimethylsiloxane group (see Non-Patent Documents 1 to 3). So-called organic/inorganic composite materials between an organic polymer and a silsesquioxane are prepared by utilizing such functional groups. Organic/inorganic composite materials can be obtained by radical polymerizing a cage-type silsesquioxane having a methacryloyloxy group singly or in the co-presence of an acrylic monomer.

In order to optimize a function of a polymer material depending upon the purpose, it is necessary to precisely analyze molecular properties of a polymer or properties as a molecular agglomerate. For that reason, a polymer having a distinct structure must be used. However, conventional organic/inorganic composite materials including the foregoing composite materials do not contain a structure-controlled polymer as an organic component. Since the majority of organic/inorganic composite materials are obtained by mechanical blending of a silsesquioxane and an organic polymer or other means, it was extremely difficult to control the structure of the composite as a molecular agglomerate. Then, it was attempted to control the structure of the polymer by using a polymerization initiator. Non-Patent Document 4 discloses that an α-haloester group is a good initiator of living radical polymerization for a styrene based monomer and a methacrylic acid based monomer. However, any silsesquioxane derivative having an α-haloester group has not been known so far.

[Non-Patent Document 1]
  J. Am. Chem. Soc., 122 (2000), 6979
[Non-Patent Document 2]
  Chemistry of Materials, 8 (1996), 1592
[Non-Patent Document 3]
  Macromolecules, 29 (1996), 2327
[Non-Patent Document 4]
  Chem. Rev., 101 (2001), 2921

An object of the invention is to provide a novel silicon compound having a living radical polymerization initiating ability for addition polymerizable monomers of a wide range and a polymer obtained by using the same, thereby solving the foregoing problems regarding the conventional organic/inorganic composite materials.

SUMMARY OF THE INVENTION

The present inventors have known that a silicon compound represented by Formula (1) having a functional group has a living radical polymerization initiating ability for addition polymerizable monomers of a wide range. Then, the present inventors have known that this silicon compound is effective for solving the foregoing problems and accomplished the present invention on the basis of this finding. The first item of the invention is shown by the following item [1].

[1] A silicon compound represented by Formula (1):

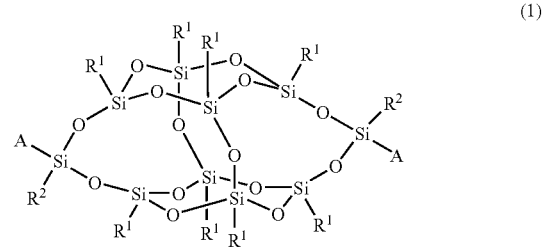

(1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and A is a group having a polymerization initiating ability for addition polymerizable monomers.

BRIEF DESCRIPTION OF THE DRAWINGS

FIG. 1 is a photograph of a thin film of Polymer (2a) by a scanning electron microscope.

FIG. 2 is a photograph of a thin film of Polymer (2b) by a scanning electron microscope.

FIG. 3 is a photograph of a thin film of Polymer (a) by a scanning electron microscope.

DETAILED DESCRIPTION OF THE INVENTION

The present invention is constructed of the foregoing item [1] and the following items [2] to [53].

[2] The silicon compound as set forth in the item [1], wherein each $R^1$ is a group independently selected from hydrogen, an alkyl having 1 to 45 carbon atoms in which arbitrary hydrogen may be replaced by fluorine and arbitrary —$CH_2$— may be replaced by —O— or a cycloalkylene, a substituted or unsubstituted aryl, and an arylalkyl constituted of a substituted or unsubstituted aryl group and an alkylene group in which arbitrary hydrogen may be replaced by fluorine and arbitrary —$CH_2$— may be replaced by —O— or a cycloalkylene; each $R^2$ is a group independently selected from an alkyl having 1 to 8 carbon atoms, phenyl, and cyclohexyl; and A is a group having a living radical polymerization initiating ability for addition polymerizable monomers.

[3] The silicon compound as set forth in the item [1], wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and A is a group represented by any one of Formula (2-1), Formula (2-2), Formula (2-3) and Formula (2-4):

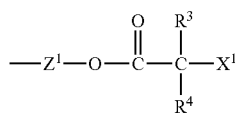

(2-1)

wherein $Z^1$ is an alkylene having 3 to 20 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen:

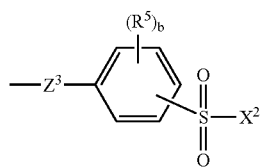

(2-2)

wherein $Z^3$ is an alkylene having 2 to 10 carbon atoms in which arbitrary —$CH_2$— may be replaced by —O—, —COO—, or —OCO—; $R^5$ is an alkyl having 1 to 3 carbon atoms; b is an integer of 0 to 2; $X^2$ is a halogen; the bonding position of —$SO_2X^2$ on the benzene ring is an ortho-position, a meta-position, or a para-position with respect to the bonding position of $Z^3$; and the bonding position of $R^5$ is an arbitrary position excluding the respective bonding positions of $Z^3$ and —$SO_2X^2$:

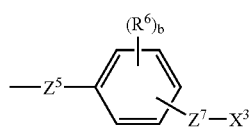

(2-3)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^5$; and the bonding position of $R^6$ is an arbitrary position excluding the respective bonding positions of $Z^5$ and $Z^7$:

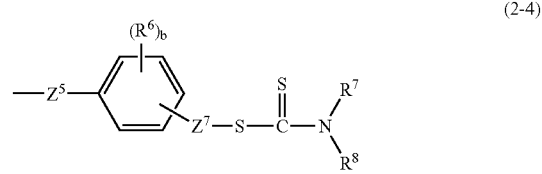

(2-4)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-positive with respect to the bonding position of $Z^5$; and the bonding position of $R^6$ is an arbitrary position excluding the respective bonding positions of $Z^5$ and $Z^7$.

[4] The silicon compound as set forth in the item [3], wherein each $R^1$ is a group independently selected from hydrogen and an alkyl having 1 to 30 carbon atoms; and in this alkyl, arbitrary hydrogen may be replaced by fluorine, and arbitrary —$CH_2$— may be replaced by —O— or a cycloalkylene.

[5] The silicon compound as set forth in the item [3], wherein each $R^1$ is a group independently selected from phenyl in which arbitrary hydrogen may be replaced by a halogen or an alkyl having 1 to 10 carbon atoms and unsubstituted naphthyl; in the alkyl as a substituent of the phenyl, arbitrary hydrogen may be replaced by fluorine, and arbitrary —$CH_2$— may be replaced by —O—, a cycloalkylene, or phenylene; and when the phenyl has plural substituents, those substituents may be the same group or a different group.

[6] The silicon compound as set forth in the item [3], wherein each $R^1$ is a group independently selected from a phenylalkyl constituted of a phenyl group in which arbitrary hydrogen may be replaced by a halogen or an alkyl having 1 to 12 carbon atoms and an alkylene group having 1 to 12 carbon atoms in which arbitrary hydrogen may be replaced by fluorine, and arbitrary —$CH_2$— may be replaced by —O— or a cycloalkylene; in the alkyl as a substituent of the phenyl group, arbitrary hydrogen may be replaced by fluorine, and arbitrary —$CH_2$— may be replaced by —O—, a cycloalkylene or phenylene; and when the phenyl group has plural substituents, those substituents may be the same group or a different group.

[7] The silicon compound as set forth in the item [3], wherein each $R^1$ is a group independently selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; and when the phenyl or the phenyl group of the phenylalkyl has plural substituents, those substituents may be the same group or a different group.

[8] The silicon compound as set forth in the item [3], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl and cyclohexyl.

[9] The silicon compound as set forth in the item [3], wherein $R^1$ is phenyl.

[10] The silicon compound as set forth in the item [3], wherein $R^1$s is phenyl; and $R^2$ is methyl.

[11] The silicon compound as set forth in the item [3], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-1):

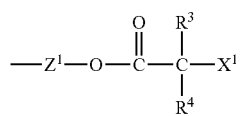

(2-1)

wherein $Z^1$ is an alkylene having 3 to 20 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen.

[12] The silicon compound as set forth in the item [11], wherein $R^1$ is phenyl; and $Z^1$ is an alkylene having 3 to 10 carbon atoms in which arbitrary —$CH_2$— may be replaced by —O—.

[13] The silicon compound as set forth in the item [11], wherein $R^1$ is phenyl; $R^2$ is methyl; $Z^1$ is —$C_3H_6$— or —$C_3H_6$—O—$C_2H_4$—; $R^3$ and $R^4$ are each methyl; and $X^1$ is bromine.

[14] The silicon compound as set forth in the item [3], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-2):

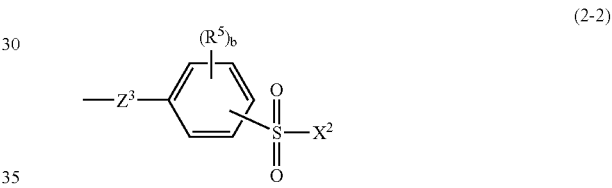

(2-2)

wherein $Z^3$ is an alkylene having 2 to 10 carbon atoms in which arbitrary —$CH_2$— may be replaced by —O—, —COO—, or —OCO—; $R^5$ is an alkyl having 1 to 3 carbon atoms; b is an integer of 0 to 2; $X^2$ is a halogen; the bonding position of —$SO_2X^2$ on the benzene ring is an ortho-position, a meta-position, or a para-position with respect to the bonding position of $Z^3$; and the bonding position of $R^5$ is an arbitrary position excluding the respective bonding positions of $Z^3$ and —$SO_2X^2$.

[15] The silicon compound as set forth in the item [14], wherein $R^1$ is phenyl; $Z^3$ is —$C_2H_4$-$Z^4$; and $Z^4$ is a single bond or an alkylene having 1 to 8 carbon atoms in which arbitrary —$CH_2$— may be replaced by —O—, —COO—, or —OCO—.

[16] The silicon compound as set forth in the item [14], wherein $R^1$ is phenyl; $R^2$ is methyl; $Z^3$ is —$C_2H_4$—; $X^2$ is chlorine or bromine; and b is 0.

[17] The silicon compound as set forth in the item [3], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-3):

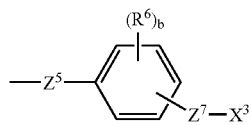

(2-3)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^5$; and the bonding position of $R^6$ is an arbitrary position excluding the respective bonding positions of $Z^5$ and $Z^7$.

[18] The silicon compound as set forth in the item [17], wherein $R^1$ is phenyl; $Z^5$ is —$C_2H_4$-$Z^6$; and $Z^6$ is a single bond or an alkylene having 1 to 8 carbon atoms in which arbitrary —$CH_2$— may be replaced by —O—, —COO—, or —OCO—.

[19] The silicon compound as set forth in the item [17], wherein $R^1$ is phenyl; $R^2$ is methyl; $Z^5$ is —$C_2H_4$—; $Z^7$ is —$CH_2$—; $X^3$ is chlorine or bromine; and b is 0.

[20] The silicon compound as set forth in the item [3], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-4):

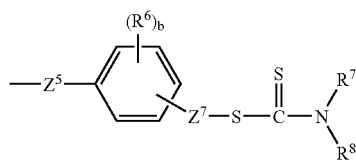

(2-4)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-positive with respect to the bonding position of $Z^5$; and the bonding position of $R^6$ is an arbitrary position excluding the respective bonding positions of $Z^5$ and $Z^7$.

[21] The silicon compound as set forth in the item [20], wherein $R^1$ is phenyl; $Z^5$ is —$C_2H_4$-$Z^6$; and $Z^6$ is a single bond or an alkylene having 1 to 8 carbon atoms in which arbitrary —$CH_2$— may be replaced by —O—, —COO—, or —OCO—.

[22] The silicon compound as set forth in the item [20], wherein $R^1$ is phenyl; $R^2$ is methyl; $Z^5$ is —$C_2H_4$—; $R^7$ and $R^8$ are each ethyl; $Z^7$ is —$CH_2$—; and b is 0.

[23] A process for producing a silicon compound represented by Formula (1-1), characterized by carrying out the following step (a), step (b) and step (c), successively:

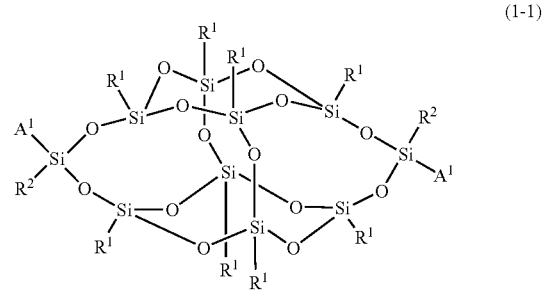

(1-1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

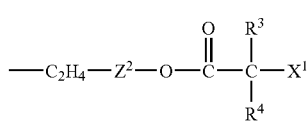

(2-1-1)

wherein $Z^2$ is an alkylene having 1 to 18 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

Step (a)

A step for reacting a compound represented by Formula (3-1) and a compound represented by Formula (4) to obtain a compound represented by Formula (5):

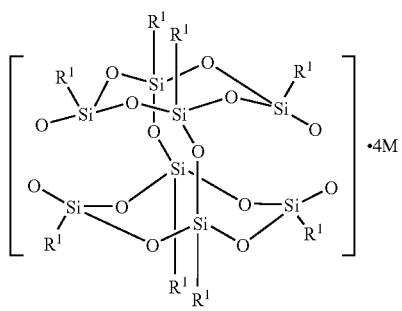

(3-1)

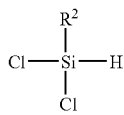

(4)

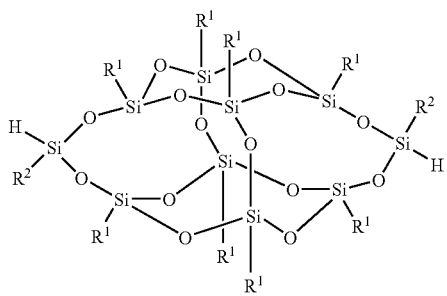

(5)

wherein $R^1$ and $R^2$ have the same meanings as those in Formula (1-1), respectively; and M is a monovalent alkali metal atom;

Step (b)

A step for reacting the compound represented by Formula (5) and a compound represented by Formula (6) in the presence of a transition metal catalyst to obtain a silicon compound represented by Formula (7):

wherein $Z^2$ has the same meaning as $Z^2$ in Formula (2-1-1); and $R^1$ and $R^2$ have the same meanings as those in Formula (1-1), respectively;

Step (c)

A step for reacting the compound represented by Formula (7) and a compound represented by Formula (8) to obtain the silicon compound represented by Formula (1-1):

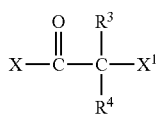

(8)

wherein $R^3$, $R^4$ and $X^1$ have the same meanings as those in Formula (2-1-1), respectively; and X is a halogen.

[24] The process as set forth in the item [23], wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[25] The process as set forth in the item [23], wherein $R^1$ is phenyl; and $R^2$ is methyl.

[26] A process for producing a silicon compound represented by Formula (1-1), characterized by carrying out the following step (d), step (b) and step (c), successively:

(7)

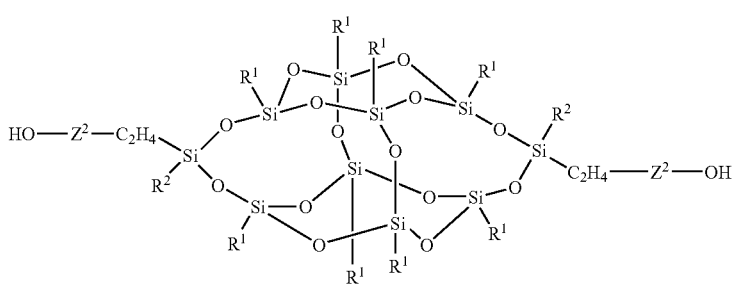

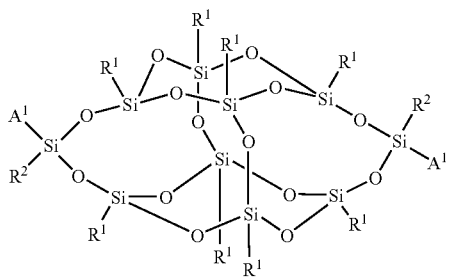
(1-1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —CH$_2$— may be replaced by —O— or a cycloalkylene; in the alkylene group of the arylalkyl, arbitrary hydrogen may be replaced by fluorine, and arbitrary —CH$_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

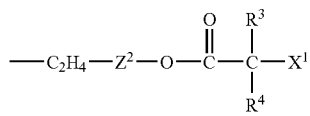
(2-1-1)

wherein $Z^2$ is a single bond or an alkylene having 1 to 18 carbon atoms, and arbitrary —CH$_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

Step (d)

A step for reacting a compound represented by Formula (3-2) and a compound represented by Formula (4) to obtain a compound represented by following formula (5):

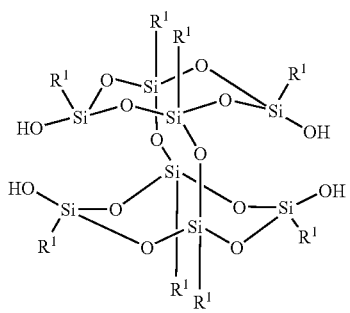
(3-2)

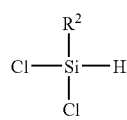
(4)

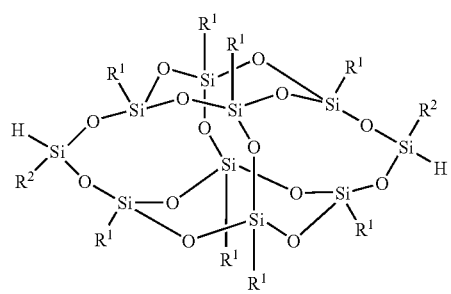
(5)

wherein $R^1$ and $R^2$ have the same meanings as those in Formula (1-1), respectively;

Step (b)

A step for reacting the compound represented by Formula (5) and a compound represented by Formula (6) in the presence of a transition metal catalyst to obtain a silicon compound represented by Formula (7):

(6)

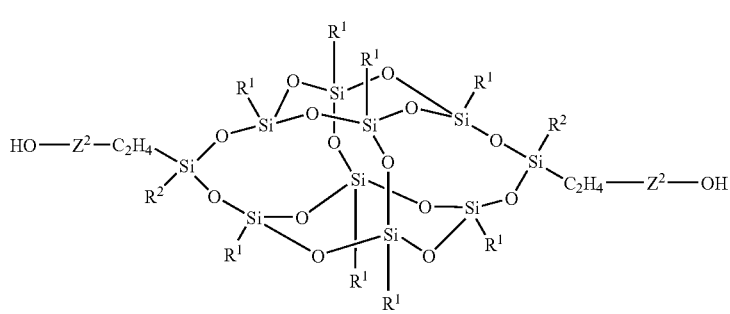
(7)

wherein $Z^2$ has the same meaning as $Z^2$ in Formula (2-1-1); and $R^1$ and $R^2$ have the same meanings as those in Formula (1-1), respectively;

Step (c)

A step for reacting the compound represented by Formula (7) and a compound represented by Formula (8) to obtain the silicon compound represented by Formula (1-1):

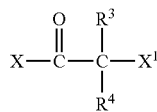
(8)

wherein $R^3$, $R^4$ and $X^1$ have the same meanings as those in Formula (2-1-1), respectively; and X is a halogen.

[27] The process as set forth in the item [26], wherein all $R^1$'s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[28] The process as set forth in the item [26], wherein $R^1$ is phenyl; and $R^2$ is methyl.

[29] A process for producing a silicon compound represented by Formula (1-3), characterized by carrying out the following step (e) and step (f), successively:

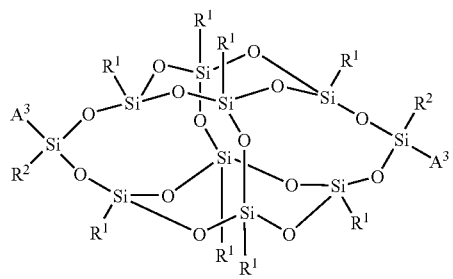
(1-3)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^3$ is a group represented by Formula (2-3-1):

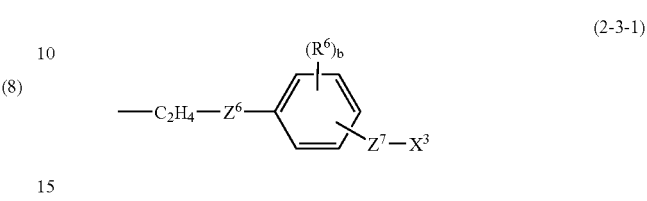
(2-3-1)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^6$; and the bonding position of $R^6$ is an arbitrary position excluding the respective bonding positions of $Z^6$ and $Z^7$;

Step (e)

A step for reacting a compound represented by Formula (4) and a compound represented by Formula (3-1) or a compound represented by Formula (3-2) to obtain a silicon compound represented by Formula (5):

(4)

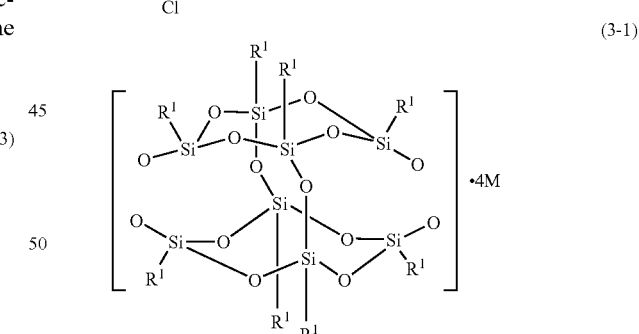
(3-1)

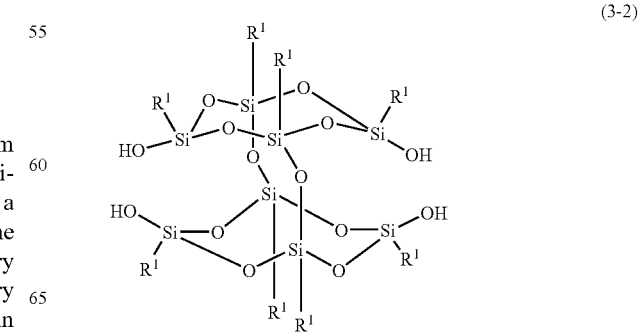
(3-2)

-continued

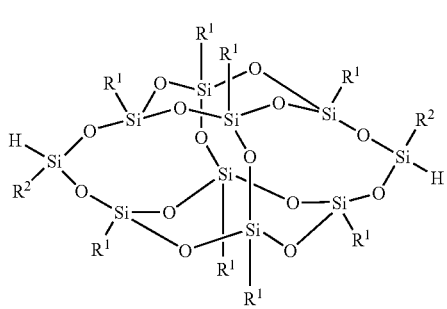 (5)

wherein R¹ and R² have the same meanings as those in Formula (1-3), respectively; and M is a monovalent alkali metal atom;

Step (f)

A step for reacting the compound represented by Formula (5) and a compound represented by Formula (2-3-2) to obtain the silicon compound represented by Formula (1-3):

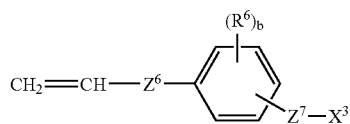 (2-3-2)

wherein $Z^6$, $R^6$, b, $Z^7$ and $X^3$ have the same meanings as those in Formula (2-3-1), respectively; and the bonding positions of $Z^7$ and $Z^6$ on the benzene ring are the same as the bonding positions of $Z^7$ and $Z^6$ in Formula (2-3-1), respectively.

[30] The process as set forth in the item [29], wherein all R¹s are the same group selected from an alkyl having 1 to 8 carbon atoms in which arbitrary hydrogen may be replaced by fluorine and arbitrary —CH₂— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH₂— may be replaced by —O— or a cycloalkylene; when the phenyl or the phenyl group of the phenylalkyl has plural substituents, those substituents may be the same group or a different group; and each R² is a group independently selected from an alkyl having 1 to 4 carbon atoms, phenyl, and cyclohexyl.

[31] The process as set forth in the item [29], wherein R¹ is phenyl; and R² is methyl.

[32] A process for producing a silicon compound represented by Formula (1-4), characterized by reacting a silicon compound represented by Formula (1-3) and a compound represented by Formula (9):

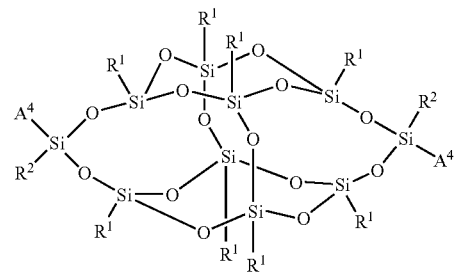 (1-4)

wherein each R¹ is a group independently selected from hydrogen, an alkyl having 1 to 45 carbon atoms in which arbitrary hydrogen may be replaced by fluorine and arbitrary —CH₂— may be replaced by —O— or a cycloalkylene, a substituted or unsubstituted aryl, and an arylalkyl constituted of a substituted or unsubstituted aryl group and an alkylene group in which arbitrary hydrogen may be replaced by fluorine and arbitrary —CH₂— may be replaced by —O— or a cycloalkylene; each R² is group independently selected from an alkyl having 1 to 8 carbon atoms, phenyl, and cyclohexyl; and A⁴ is a group represented by Formula (2-4-1):

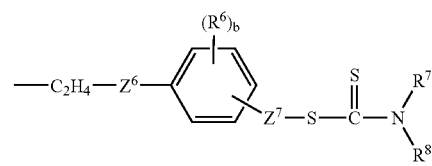 (2-4-1)

wherein $Z^6$ is a single bond or an alkylene having 1 to 8 carbon atoms in which arbitrary —CH₂— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —CH₂— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-position with respect to the bonding position of $Z^6$; and the bonding position of $R^6$ is an arbitrary position excluding the respective bonding positions of $Z^6$ and $Z^7$;

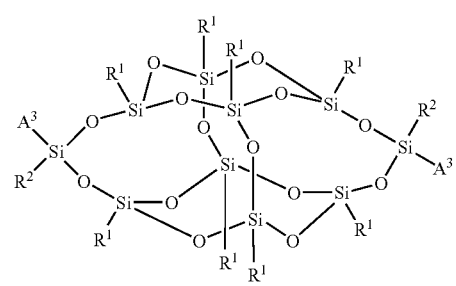 (1-3)

wherein $R^1$ and $R^2$ have the same meanings as those in Formula (1-4), respectively; and $A^3$ is a group represented by Formula (2-3-1):

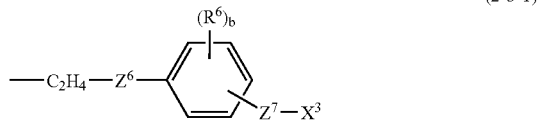

(2-3-1)

wherein $Z^6$, $R^6$, b and $Z^7$ have the same meanings as those in Formula (2-4-1), respectively; $X^3$ is a halogen; and the bonding positions of $Z^7$ and $Z^6$ on benzene ring are the same as the bonding positions of $Z^7$ and $Z^6$ in Formula (2-4-1), respectively;

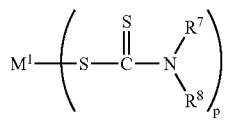

(9)

wherein $R^7$ and $R^8$ have the same meanings as those in Formula (2-4-1), respectively; $M^1$ is a metal atom belonging to the group 1 or group 2 of the periodic table; and p is a value equal to the valence of $M^1$.

[33] The process as set forth in the item [32], wherein all $R^1$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[34] The process as set forth in the item [32], wherein $R^1$ is phenyl; and $R^2$ is methyl.

[35] A process for producing a silicon compound represented by Formula (1-1), characterized by carrying out the following step (g) and step (h), successively:

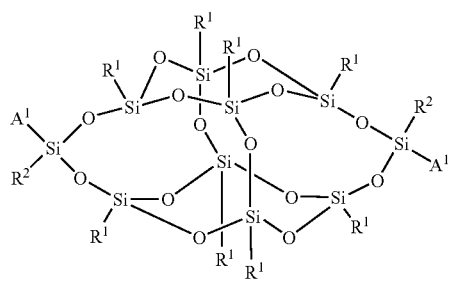

(1-1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

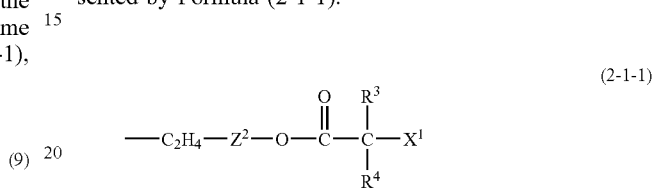

(2-1-1)

wherein $Z^2$ is an alkylene having 1 to 18 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

Step (g)

A step for reacting a compound represented by Formula (4) and a compound represented by Formula (2-1-2) in the presence of a transition metal catalyst to obtain a compound represented by Formula (2-1-3):

(4)

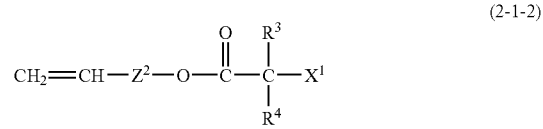

(2-1-2)

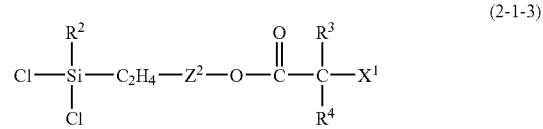

(2-1-3)

wherein $R^2$ has the same meaning as $R^2$ in Formula (1-1); and $Z^2$, $R^3$, $R^4$ and $X^1$ have the same meanings as those in Formula (2-1-1), respectively;

Step (h)

A step for reacting the compound represented by Formula (2-1-3) and a compound represented by Formula (3-1) or a compound represented by Formula (3-2) to obtain the silicon compound represented by Formula (1-1):

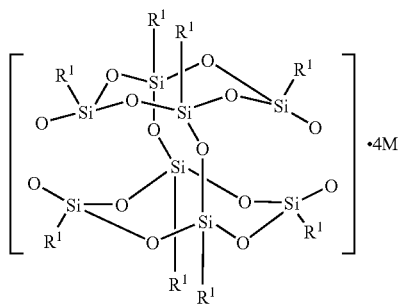

(3-1)

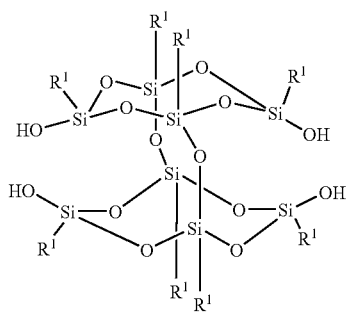

(3-2)

wherein $R^1$ has the same meaning as $R^1$ in Formula (1-1); and M is a monovalent alkali metal atom.

[36] The process as set forth in the item [35], wherein all $R^1$'s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[37] The process as set forth in the item [35], wherein $R^1$ is phenyl; and $R^2$ is methyl.

[38] A process for producing a silicon compound represented by Formula (1-2), characterized by carrying out the following step (i) and step (j), successively:

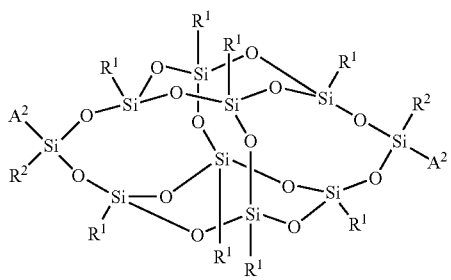

(1-2)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^2$ is a group represented by Formula (2-2-1):

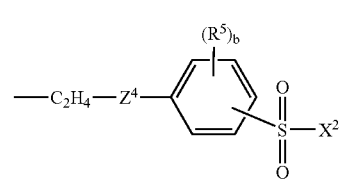

(2-2-1)

wherein $Z^4$ is a single bond or an alkylene having 1 to 8 carbon atoms, and arbitrary —$CH_2$— in this alkylene may be replaced by —O—, —COO—, or —OCO—; $R^5$ is an alkyl having 1 to 3 carbon atoms; b is an integer of 0 to 2; $X^2$ is a halogen; the bonding position of —$SO_2X^2$ on the benzene ring is an ortho-position, a meta-position, or a para-position with respect to the bonding position of $Z^4$; and the bonding position of $R^5$ is an arbitrary position excluding the respective bonding positions of $Z^4$ and —$SO_2X^2$;

Step (i)

A step for reacting a compound represented by Formula (4) and a compound represented by Formula (2-2-2) in the presence of a transition metal catalyst to obtain a compound represented by Formula (2-2-3):

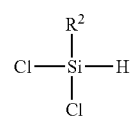

(4)

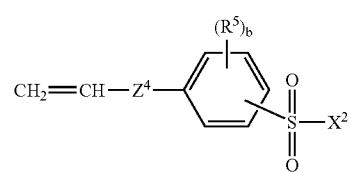

(2-2-2)

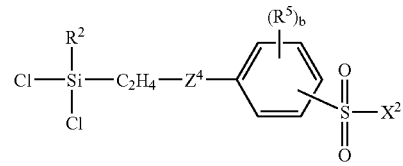

(2-2-3)

wherein $R^2$ has the same meaning as $R^2$ in Formula (1-2); $Z^4$, $R^5$, b and $X^2$ have the same meanings as those in Formula (2-2-1), respectively; and the bonding positions of —$SO_2X^2$ and $R^5$ on the benzene ring are the same as the bonding positions of —$SO_2X^2$ and $R^5$ in Formula (2-2-1), respectively;

Step (j)

A step for reacting the compound represented by Formula (2-2-3) and a compound represented by Formula (3-1) or a compound represented by Formula (3-2) to obtain the silicon compound represented by Formula (1-2):

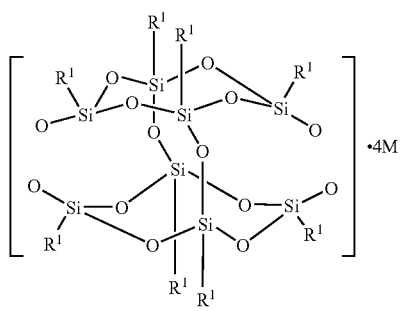

(3-1)

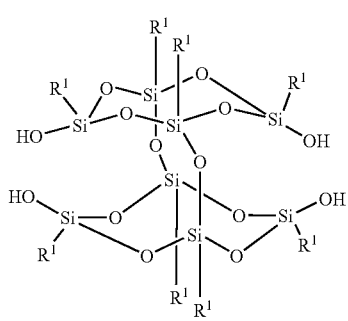

(3-2)

wherein $R^1$ has the same meaning as $R^1$ in Formula (1-2); and M is a monovalent alkali metal atom.

[39] The process as set forth in the item [38], wherein all $R^1$'s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[40] The process as set forth in the item [38], wherein $R^1$ is phenyl; and $R^2$ is methyl.

[41] A process for producing a silicon compound represented by Formula (1-3), characterized by carrying out the following step (k) and step (l), successively:

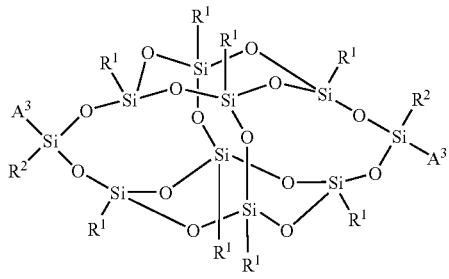

(1-3)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl and cyclohexyl; and $A^3$ is a group represented by Formula (2-3-1):

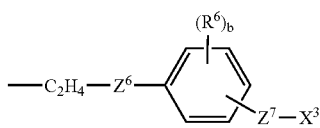

(2-3-1)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^5$ on the benzene ring is a meta-position or a para-position with respect to the bonding position of $Z^6$; and the bonding position of $R^6$ is an arbitrary position excluding the respective bonding positions of $Z^6$ and $Z^7$;

Step (k)

A step for reacting a compound represented by Formula (4) and a compound represented by Formula (2-3-2) in the presence of a transition metal catalyst to obtain a compound represented by Formula (2-3-3):

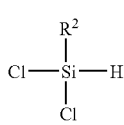

(4)

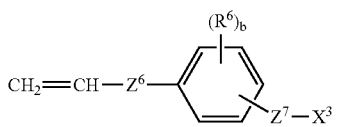

(2-3-2)

-continued

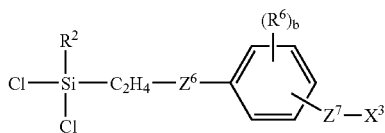
(2-3-3)

wherein $R^2$ has the same meaning as $R^2$ in Formula (1-3); $Z^6$, $R^6$, b, $Z^7$ and $X^3$ have the same meanings as those in Formula (2-3-1), respectively; and the bonding positions of $Z^7$ and $Z^6$ on the benzene ring are the same as the bonding positions of $Z^7$ and $Z^6$ in Formula (2-3-1), respectively;

Step (1)

A step for reacting the compound represented by Formula (2-3-3) and a compound represented by Formula (3-1) or a compound represented by Formula (3-2) to obtain the silicon compound represented by Formula (1-3):

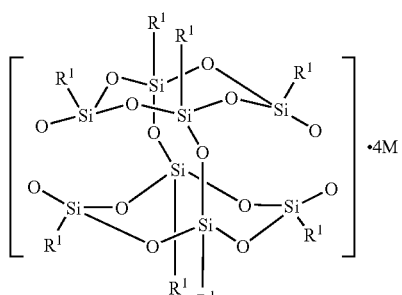
(3-1)

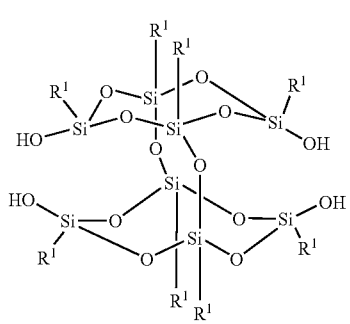
(3-2)

wherein $R^1$ has the same meaning as $R^1$ in Formula (1-3); and M is a monovalent alkali metal atom.

[42] The process as set forth in the item [41], wherein all $R^1$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

[43] The process as set forth in the item [41], wherein $R^1$ is phenyl; and $R^2$ is methyl.

[44] A polymer obtained by polymerizing an addition polymerizable monomer using the silicon compound as set forth in the item [1] as an initiator in the presence of a transition metal complex as a catalyst.

[45] A polymer obtained by polymerizing an addition polymerizable monomer using the silicon compound as set forth in the item [3] as an initiator in the presence of a transition metal complex as a catalyst.

[46] A polymer represented by Formula (P-1)

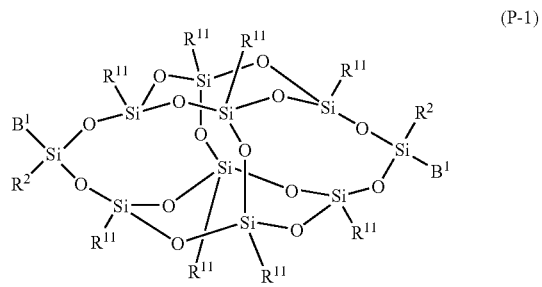
(P-1)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^1$ is a group represented by Formula (2-1-P):

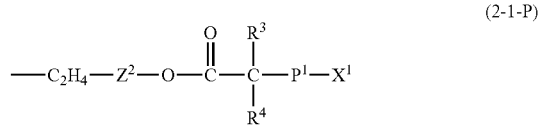
(2-1-P)

wherein $Z^2$ is an alkylene group having 1 to 18 carbon atom, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; $X^1$ is a halogen; and $P^1$ is a chain of a constitutional unit obtained by polymerization of an addition polymerizable monomer.

[47] A polymer represented by Formula (P-2):

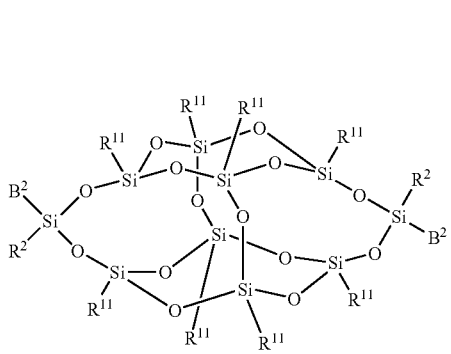

(P-2)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^2$ is a group represented by Formula (2-2-P):

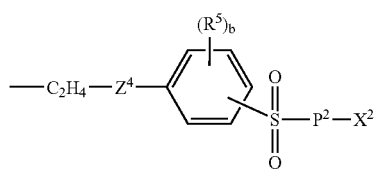

(2-2-P)

wherein $Z^4$ is a single bond or an alkylene having 1 to 8 carbon atoms in which arbitrary —$CH_2$— may be replaced by —O—, —COO— or —OCO—; $R^5$ is an alkyl having 1 to 3 carbon atoms; b is an integer of 0 to 2; $X^2$ is a halogen; the bonding position of —$SO_2$—$P^2$—$X^2$ on the benzene ring is an ortho-position, a meta-position, or a para-position with respect to the bonding position of $Z^4$; the bonding position of $R^5$ is an arbitrary position excluding the respective bonding positions of $Z^4$ and —$SO_2$—$P^2$—$X^2$; and $P^2$ is a chain of a constitutional unit obtained by polymerization of an addition polymerizable monomer.

[48] A polymer represented by Formula (P-3):

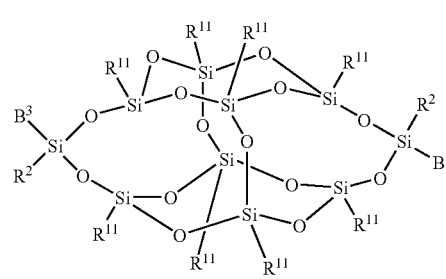

(P-3)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^3$ is a group represented by Formula (2-3-P):

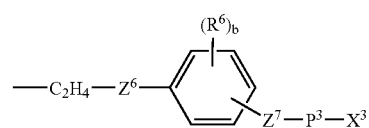

(2-3-P)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^6$; the bonding position of $R^6$ is an arbitrary position excluding the respective bonding positions of $Z^6$ and $Z^7$; and $P^3$ is a chain of a constitutional unit obtained by polymerization of an addition polymerizable monomer.

[49] A polymer represented by Formula (P-4):

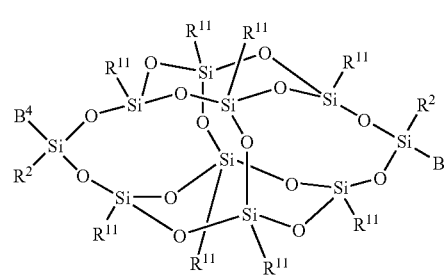

(P-4)

wherein all R[11]s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^4$ is a group represented by Formula (2-4-P):

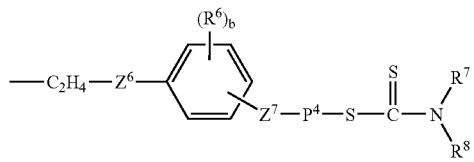

(2-4-P)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-position with respect to the bonding position of $Z^6$; the bonding position of $R^6$ is an arbitrary position excluding the respective bonding positions of $Z^6$ and $Z^7$; and $P^4$ is a chain of a constitutional unit obtained by polymerization of an addition polymerizable monomer.

[50] The polymer as set forth in the item [46], wherein the addition polymerizable monomer is at least one member selected from (meth)acrylic acid derivatives and styrene derivatives.

[51] The polymer as set forth in the item [47], wherein the addition polymerizable monomer is at least one member selected from a (meth)acrylic acid derivative and a styrene derivative.

[52] The polymer as set forth in the item [48], wherein the addition polymerizable monomer is at least one member selected from a (meth)acrylic acid derivative and a styrene derivative.

[53] The polymer as set forth in the item [49], wherein the addition polymerizable monomer is at least one member selected from (meth)acrylic acid derivatives and styrene derivatives.

The present invention will be hereunder described in more detail.

First of all, the terminologies as used in the present invention will be described. The term "arbitrary" means that not only the position but also the number can be arbitrarily selected. When arbitrary —$CH_2$— may be replaced by —O—, the case where the continuous plural number of —$CH_2$— is replaced by —O— is not included. The expression that arbitrary A may be replaced by B or C, comprises not only the case where arbitrary A is replaced by B and the case where arbitrary A is replaced by C, but also the case where arbitrary A is replaced by B and at the same time, remaining arbitrary A is replaced by C. For example, the alkyl in which arbitrary —$CH_2$— may be replaced by —O— or a cycloalkylene includes an alkyl, an alkoxy, an alkoxyalkyl, a cycloalkyl, a cycloalkyloxy, an alkylcycloalkyl, an alkoxycycloalkyl, a cycloalkylalkyl, and a cycloalkyloxyalkyl. All of the alkyl and the alkylene may be a linear group or a branched group. All of the cycloalkyl and the cycloalkenyl may be or may not be a group having a crosslinked ring structure. The (meth)acrylic acid derivative is used as a general term of an acrylic acid derivative and a methacrylic acid derivative. The (meth)acrylate is used as a general term of an acrylate and a methacrylate. The (meth)acryloyloxy is used as a general term of an acryloyloxy and a methacryloyloxy.

The silicon compound of the invention is represented by Formula (1). In the following description, the compound represented by Formula (1) is sometimes expressed as "compound (1)". With respect to compounds represented by other formulae, they are sometimes expressed by the same abbreviation method.

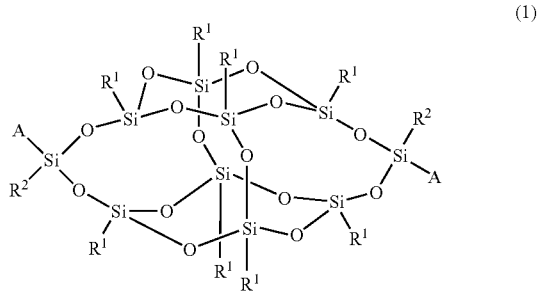

(1)

In Formula (1), each $R^1$ is a group independently selected from hydrogen, an alkyl, a substituted or unsubstituted aryl, and an arylalkyl constituted of a substituted or unsubstituted aryl group and an alkylene group. Though it is preferred that all $R^1$s are the same group, they may be constituted of two or more kinds of different groups. Examples of the case where eight $R^1$s are constituted of different groups include the case where they are constituted of two or more kinds of alkyls, the case where they are constituted of two or more kinds of aryls, the case where they are constituted of two or more kinds of arylalkyls, the case where they are constituted of hydrogen and at least kind of an aryl, the case where they are constituted of at least one kind of an alkyl and at least one kind of an aryl, the case where they are constituted of at least one kind of an alkyl and at least one kind of an arylalkyl, and the case where they are constituted of at least one kind of an aryl and at least one kind of an arylalkyl. Combinations other than these examples may also be employed. The compound (1) having at least two kinds of different $R^1$s can be obtained by using two or more kinds of raw materials in producing this compound. The raw materials will be described later.

When $R^1$ is an alkyl, the alkyl has 1 to 45 carbon atoms, preferably 1 to 30 carbon atoms, and more preferably 1 to 8 carbon atoms. Arbitrary hydrogen may be replaced by fluorine; and arbitrary —$CH_2$— may be replaced by —O— or a cycloalkylene. Preferred examples of the alkyl include an unsubstituted alkyl having 1 to 30 carbon atoms, an alkoxyalkyl having 2 to 29 carbon atoms, an alkyl having 1 to 8 carbon atoms in which one —CH$_2$— is replaced by a cycloalkylene, and the foregoing groups in which, however, arbitrary hydrogen is replaced by fluorine. The cycloalkylene preferably has 3 to 8 carbon atoms.

Examples of the unsubstituted alkyl having 1 to 30 carbon atoms include methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl, and triacontyl.

Examples of the fluorinated alkyl having 1 to 30 carbon atoms include 2-fluoroethyl, 2,2-difluoroethyl, 3,3,3-trifluoropropyl, hexafluoropropyl, nonafluoro-1,1,2,2-tetrahydrohexyl, tridecafluoro-1,1,2,2-tetrahydrooctyl, heptadecafluoro-1,1,2,2-tetrahydrodecyl, perfluoro-1,1,2,2-tetrahydrododecyl, and perfluoro-1,1,2,2-tetrahydrotetradecyl.

Examples of the alkoxyalkyl and the fluorinated alkoxyalkyl each having 2 to 29 carbon atoms include 3-methoxypropyl, methoxyethoxyundecyl, 2-fluoroethyloxypropyl, 2,2,2-trifluoroethyloxypropyl, 2-fluoro-1-fluoromethylethyloxypropyl, 2,2,3,3-tetrafluoropropyloxypropyl, 2,2,3,3,3-pentafluoropropyloxypropyl, hexafluoroisopropyloxypropyl, heptafluoroisopropyloxypropyl, hexafluorobutyloxypropyl, heptafluorobutyloxypropyl, octafluoroisobutyloxypropyl, octafluoropentyloxypropyl, 2-fluoroethyloxybutyl, 2,2,2-trifluoroethyloxybutyl, 2-fluoro-1-fluoromethylethyloxybutyl, 2,2,3,3-tetrafluoropropyloxybutyl, 2,2,3,3,3-pentafluoropropyloxybutyl, hexafluoroisopropyloxybutyl, hexafluorobutyloxybutyl, heptafluorobutyloxybutyl, octafluoroisobutyloxybutyl, octafluoropentyloxybutyl, 2-fluoroethyloxyisobutyl, 2,2,2-trifluoroethyloxyisobutyl, 2-fluoro-1-fluoromethylethyloxyisobutyl, 2,2,3,3-tetrafluoropropyloxypropyl, 2,2,3,3,3-pentafluoropropyloxybutyl, hexafluoroisopropyloxybutyl, hexafluorobutyloxyisobutyl, heptafluorobutyloxyisobutyl, octafluoroisobutyloxyisobutyl, and octafluoropentyloxyisobutyl.

Examples of the alkyl having 1 to 8 carbon atoms in which one —CH$_2$— is replaced by a cycloalkylene include cyclohexylmethyl, adamantanethyl, cyclopentyl, cyclohexyl, 2-bicycloheptyl, and cyclooctyl. The cyclohexyl is an example in which —CH$_2$— of methyl is replaced by cyclohexylene. The cyclohexylmethyl is an example in which —CH$_2$— at the β-position of ethyl is replaced by cyclohexylene.

Examples of the case where R$^1$ in Formula (1) is a substituted or unsubstituted aryl include phenyl in which arbitrary hydrogen may be replaced by a halogen or an alkyl having 1 to 10 carbon atoms and unsubstituted naphthyl. Preferred examples of the halogen include fluorine, chlorine and bromine. In the alkyl as a substituent of phenyl, arbitrary hydrogen may be replaced by fluorine; and arbitrary —CH$_2$— may be replaced by —O— or phenylene. That is, specific examples of the preferred aryl include phenyl, unsubstituted naphthyl, an alkylphenyl, an alkyloxyphenyl, phenyl having, as a substituent, an alkyl in which at least one —CH$_2$— is replaced by phenylene, and the foregoing groups in which, however, arbitrary hydrogen is replaced by a halogen. Incidentally, when expressed merely as "phenyl" without particularly saying, it is meant that the phenyl is unsubstituted phenyl.

Examples of the halogenated phenyl include pentafluorophenyl, 4-chlorophenyl, and 4-bromophenyl.

Examples of the alkylphenyl include 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl, and 2,4,6-tris(1-methylethyl)phenyl.

Examples of the alkyloxyphenyl include (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl, and 4-(1,1-dimethylethoxy)phenyl.

Examples of the phenyl having, as a substituent, a group in which at least one —CH$_2$— in the alkyl is replaced by phenylene include 4-phenoxyphenyl, 3-(phenylmethyl)phenyl, biphenyl, and terphenyl. The terphenyl is phenyl having, as a substituent, a group in which two of —CH$_2$— in ethyl are replaced by phenylene.

Examples of the phenyl in which a part of hydrogens in the benzene ring is replaced by a halogen and other hydrogens are replaced by an alkyl or an alkyloxy include 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, and 2,3-difluoro-4-propoxyphenyl.

Next, examples of the case where R$^1$ in Formula (1) is a substituted or unsubstituted arylalkyl will be described. In the alkylene group of the arylalkyl, arbitrary hydrogen may be replaced by fluorine; and arbitrary —CH$_2$— may be replaced by —O— or a cycloalkylene. A preferred example of the arylalkyl is a phenylalkyl. At this time, arbitrary hydrogen of the phenyl group may be replaced by a halogen or an alkyl having 1 to 12 carbon atoms. In this alkyl, arbitrary hydrogen may be replaced by fluorine; and arbitrary —CH$_2$— may be replaced by —O—, a cycloalkylene, or phenylene. The alkylene group preferably has 1 to 12 carbon atoms, and more preferably 1 to 8 carbon atoms.

Examples of the unsubstituted phenylalkyl include phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl, and 1-phenylhexyl.

Examples of the phenylalkyl group in which at least one hydrogen of the phenyl group is replaced by fluorine include 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl, and 2-(4-fluorophenyl)propyl.

Examples of the phenylalkyl in which at least one hydrogen of the phenyl group is replaced by chlorine include 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-trichlorophenyl)ethyl, 2-(2,3,6-trichlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6- trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl, and 1-(4-chlorophenyl)butyl.

Examples of the phenylalkyl in which at least one hydrogen of the phenyl group is replaced by bromine include 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl, and 2-(4-bromophenyl)propyl.

Examples of the phenylalkyl in which at least one hydrogen of the phenyl group is replaced by an alkyl having 1 to 12 carbon atoms include 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)propyl, 2-(2,4-dimethylphenyl)propyl, 2-(3,4-dimethylphenyl)propyl, 2-(2,5-dimethylphenyl)butyl, (4-(1-methylethyl)phenyl)methyl, 2-(4-(1,1-dimethylethyl)phenyl)ethyl, 2-(4-(1-methylethyl)phenyl)propyl, and 2-(3-(1-methylethyl)phenyl)propyl.

Examples of the phenylalkyl having, as a substituent of the phenyl group, an alkyl having 1 to 12 carbon atoms in which at least one hydrogen is replaced by fluorine include 3-(trifluoromethyl)phenylmethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl) ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl) propyl, 1-methyl-1-(4-nonafluorobutylphenyl) ethyl, 2-(4-tridecafluorohexylphenyl)propyl, 1-methyl-1i-(4-tridecafluorohexylphenyl)ethyl, 2-(4-heptadecafluorooctylphenyl)propyl, and 1-methyl-1-(4-heptadecafluorooctylphenyl)ethyl.

Examples of the phenylalkyl having, as a substituent of the phenyl group, a group in which one —CH$_2$— in an alkyl group having 1 to 12 carbon atoms is replaced by —O— include 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, and 2-(3-(methoxymethyl)phenyl)ethyl.

Examples of the phenylalkyl having, as a substituent of the phenyl group, an alkyl having 1 to 12 carbon atoms in which one —CH$_2$— is replaced by a cycloalkylene and another —CH$_2$— may be replaced by —O— include cyclopentylphenylmethyl, cyclopentyloxyphenylmethyl, cyclohexylphenylmethyl, cyclohexylphenylethyl, cyclohexylphenylpropyl, and cyclohexyloxyphenylmethyl.

Examples of the phenylalkyl having, as a substituent of the phenyl group, an alkyl having 1 to 12 carbon atoms in which one —CH$_2$— is replaced by phenylene and another —CH$_2$— may be replaced by —O— include 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl, and 2-(4-biphenylyl)propyl.

Examples of the phenylalkyl in which at least two hydrogens of the phenyl group are replaced by a different group include 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl, and 11-(3-chloro-4-methoxyphenyl)undecyl.

Most preferred examples of the phenyl group in the phenylalkyl include an unsubstituted phenyl group and a phenyl having, as a substituent, at least one of fluorine, an alkyl having 1 to 4 carbon atoms, and methoxy.

Examples of the phenylalkyl in which in the alkylene group constituting the phenylalkyl, at least one —CH$_2$— is replaced by —O— or a cycloalkylene include 3-phenoxypropyl, phenylcyclohexyl, and phenoxycyclohexyl.

Incidentally, an aliphatic unsaturated bond may be contained in R$^1$ so far as it does not hinder the polymerization of the addition polymerizable monomer.

More preferred specific examples of R$^1$ include ethyl, 2-fluoroethyl, 2,2-difluoroethyl, propyl, 3,3,3-trifluoropropyl, hexafluoropropyl, 2-methylpropyl, 2,4,4-trimethylpentyl, tridecafluoro-1,1,2,2-tetrahydrooctyl, cyclopentyl, cyclohexyl, phenyl, a halogenated phenyl, methylphenyl, dimethylphenyl, methoxyphenyl, unsubstituted naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-methoxyphenylpropyl, and phenoxypropyl. R$^1$ is most preferably phenyl.

In the present invention, R$^1$ may also be a group which is used for alignment control of a liquid crystal. Examples thereof are given below.

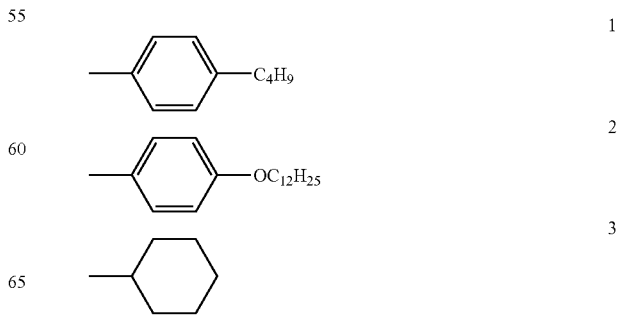

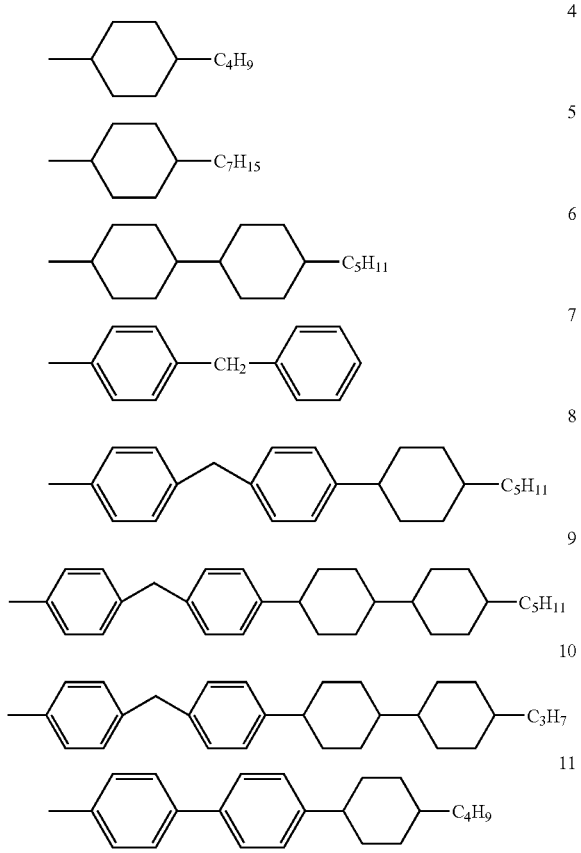

A group having a steroid skeleton may be present in the group which is used for alignment control. Examples of the group having such a steroid skeleton include cholesteryl, androsteryl, β-cholesteryl, epiandrosteryl, ergosteryl, estryl, 11α-hydroxymethylsteryl, 11α-progesteryl, lanosteryl, melatonyl, methyltestosteryl, norethisteryl, pregnenonyl, β-cytosteryl, stigmasteryl, testosteryl, and acetic acid cholesterol ester. These groups may be bound to silicon via phenyl or may be a group directly bound to silicon.

In Formula (1), each $R^2$ is independently an alkyl having 1 to 8 carbon atoms, phenyl, or cyclohexyl. Examples of the alkyl include methyl, ethyl, propyl, isopropyl, butyl, isobutyl, pentyl, 2-methylbutyl, hexyl, 2-methylpentyl, heptyl, 2-methylhexyl, octyl, 2-methylheptyl, and 2-ethylhexyl. Of these, alkyls having 1 to 4 carbon atoms are preferred. A most preferred example of $R^2$ is methyl.

In Formula (1), A is a group having a polymerization initiating ability, and preferably a living radical polymerization initiating ability for the addition polymerizable monomer. Examples of A include a group having an α-haloester group, a group having a halogenated sulfonyl group, a group having a haloalkylphenyl group, a group having an MgBr group, a group having a dithiocarbamate group, and a group having a nitroxyl group. Examples of the haloalkylphenyl group include chloromethylphenyl, bromomethylphenyl, and iodomethylphenyl.

The MgBr group can be introduced in the following manner. First of all, a silsesquioxane derivative having a double bond such as a styryl group and a vinyl group is synthesized. Next, the double bond site of this derivative is subjected to hydroboration by using a borane-dimethyl sulfide complex, to form a boron-containing silsesquioxane derivative. By reacting this boron-containing silsesquioxane derivative and pentane-1,5-diyl-di(magnesium bromide), the MgBr group can be introduced.

The nitroxyl group can be introduced in the following manner. First of all, a silsesquioxane derivative having a styryl group is synthesized. To this, a nitroxide capable of forming a stable radical which does not participate in the polymerization, such as di-t-butyl nitroxide, 2,2,6,6-tetramethylpiperidinyl-1-oxy, and N-t-butyl-1-diethylphosphone-2,2-dimethylpropyl nitroxide, is added, and (N,N'-bis(3,5-di-t-butylsalicylidene)-1,2-cyclohexanediaminato) manganese(III) chloride (Jacobsen catalyst) is further introduced. Next, a styryl radical is generated in the co-presence of, for example, di-t-butyl peroxide and sodium borohydride as radical generators, whereby the desired nitroxyl group can be introduced. The resulting silsesquioxane derivative can be utilized as a polymerization initiator for styrene or methyl (meth)acrylate.

In Formula (1), A also includes an exchange chain transfer radical polymerization initiating group represented by reversible addition-fragmentation chain transfer (RAFT). Examples of such A include a group having a dithioester group.

The dithioester group can be introduced in the following manner. Benzyl bromide and metallic magnesium are reacted with each other to form phenyl magnesium bromide, to which is then added carbon disulfide to form dithiophenyl magnesium bromide. Then, by reacting the subject compound and a silsesquioxane derivative having a haloalkylphenyl group or an α-haloester group, the desired dithioester group can be introduced. The resulting silsesquioxane derivative can be utilized as an exchange chain transfer radical polymerization initiator for styrene, acrylates, methyl (meth)acrylate, acrylic acid, styrenesulfonic acid, methyl (meth)acrylamide, or N-isopropyl acrylamide by using a polymerization active catalyst such as benzoyl peroxide and azobisisobutyronitrile.

Preferred examples of A include a group having an α-haloester group, a group having a halogenated sulfonyl group, a group having a haloalkylphenyl group, and a group having a dithiocarbamate group.

The group having an α-haloester group means a group having an α-halocarbonyloxy in the terminal thereof. As a polymerization method in which this α-halocarbonyloxy is used as an initiating group of radical polymerization, an atom transfer radical polymerization method is known. A polymerization catalyst which is used in this method is a metal complex containing, as a central metal atom, an element belonging to the Group 8, the Group 9, the Group 10, or the Group 11 of the Periodic Table. In this atom transfer radical polymerization, it is known that a group having an α-halocarbonyloxy has an excellent polymerization initiating ability. It is also well known that this polymerization proceeds in a living polymerization way. That is, the silicon compound having an α-haloester group according to the invention has an excellent polymerization initiating ability in the presence of a transition metal complex so that it can continue to keep living polymerization properties. Moreover, the silicon compound having an α-haloester group according to the invention can initiate polymerization for any radical polymerizable monomers. In particular, the silicon compound having an α-haloester group according to the invention can reveal excellent living polymerization properties for (meth)acrylic acid derivatives or styrene based derivatives.

Incidentally, since the silicon compound having an α-haloester group according to the invention has an α-halocarbonyloxy in the terminal thereof, it can be derived into a number of derivatives by applying a variety of organic reactions. For example, by reacting this silicon compound and lithium, magnesium, zinc, etc., it can be derived into a silsesquioxane derivative having an organometal functional group. Concretely, by reacting the silicon compound having an α-haloester group according to the invention and zinc to derive it into a silsesquioxane derivative having an organozinc functional group and then adding an aldehyde or a ketone, it is possible to convert the aldehyde or ketone into an alcohol. Accordingly, the silsesquioxane derivative having an organozinc functional group is useful as an intermediate raw material to be used in a so-called Reformatsky reaction.

Since the α-halocarbonyloxy group has strong electrophilicity, it can be converted into an amino group, a mercapto group, or the like by using a variety of nucleophilic reagents. In addition, by treating the α-halocarbonyloxy group with an enamine to form an imine salt and hydrolyzing this imine salt, it is possible to convert the imine salt into a ketone. That is, the silicon compound having an α-halocarbonyloxy group according to the invention is also useful as an intermediate raw material to be used in a Stork-enamine reaction. By reacting this silicon compound and an aliphatic or aromatic Grignard reagent, silsesquioxane derivatives having an organic functional group or a polymerizable functional group of every kind can also be formed. Accordingly, the silicon compound having an α-halocarbonyloxy group according to the invention can be utilized as not only a polymerization initiator but also a useful intermediate for a variety of organic syntheses.

In Formula (1), A may be a group having an anionic polymerization initiating ability or a group having a cationic polymerization initiating ability. For example, the haloalkylphenyl group becomes an initiator of cationic polymerization in the co-presence of silver perchlorate, and the MgBr group can be utilized as an anionic polymerization initiator for styrene or methyl (meth)acrylate. In Formula (1), A may be a group having a usual radical polymerization initiating ability. Examples of such A include a group having an organic peroxide, a group having an azo group, and a group having benzophenone.

A preferred example of the group having an α-haloester group is a group represented by Formula (2-1).

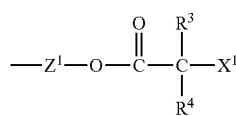

(2-1)

In Formula (2-1), the respective symbols have the following meanings. $Z^1$ is an alkylene having 3 to 20 carbon atoms, and arbitrary —CH$_2$— in this alkylene may be replaced by —O—. $R^3$ is hydrogen, an alkyl having 1 to 20 carbon atoms, an aryl having 6 to 20 carbon atoms, or an arylalkyl having 7 to 20 carbon atoms; and $R^4$ is an alkyl having 1 to 20 carbon atoms, an aryl having 6 to 20 carbon atoms, or an arylalkyl having 7 to 20 carbon atoms. $X^1$ is a halogen.

A preferred example of the silicon compound having an α-haloester group according to the invention is a compound represented by Formula (1-1).

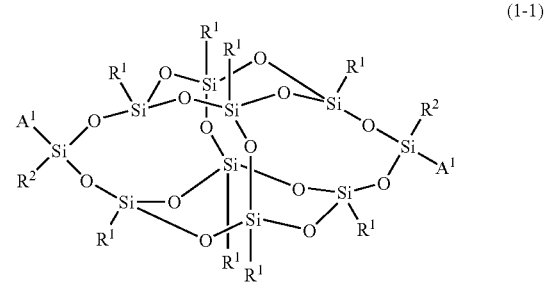

(1-1)

In Formula (1-1), $R^1$ and $R^2$ have the same meanings as those in Formula (1), respectively; and $A^1$ is a group represented by Formula (2-1-1).

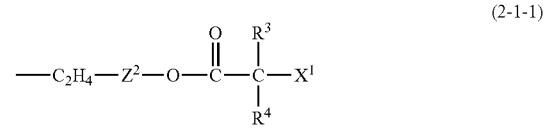

(2-1-1)

In bonding an organic group to an Si atom, representative examples of a method for obtaining a derivative which is not hydrolyzed include a method for reacting Si-halogen and a Grignard reagent and a method for reacting Si—H and an aliphatic unsaturated bond-containing compound. The latter is usually called a hydrosilylation reaction method. In the invention, the hydrosilylation reaction method is more easily applicable in view of easiness of availability of raw materials. That is, a preferred method for introducing a functional group into the silsesquioxane derivative is a method for bonding an Si—H functional silsesquioxane derivative to a compound having an unsaturated bond in the terminal thereof by a hydrosilylation reaction. That is, Formula (2-1-1) is a preferred example of Formula (2-1).

In Formula (2-1-1), $Z^2$ is an alkylene having 1 to 18 carbon atoms. A more preferred example of $Z^2$ is an alkylene having 1 to 8 carbon atoms. Arbitrary —CH$_2$— in this alkylene may be replaced by —O—. Preferred examples of such an alkylene include —CH$_2$—, —C$_2$H$_4$—, —C$_3$H$_6$—, and —CH$_2$—O—C$_2$H$_4$—. $R^3$ is hydrogen, an alkyl having 1 to 20 carbon atoms, an aryl having 6 to 20 carbon atoms, or an arylalkyl having 7 to 20 carbon atoms; and $R^4$ is an alkyl having 1 to 20 carbon atoms, an aryl having 6 to 20 carbon atoms, or an arylalkyl having 7 to 20 carbon atoms. Preferred examples of $R^3$ include hydrogen, an alkyl having 1 to 20 carbon atoms, phenyl in which arbitrary hydrogen may be replaced by an alkyl having 1 to 14 carbon atoms, and a phenylalkyl constituted of a phenyl group in which arbitrary hydrogen may be replaced by an alkyl having 1 to 14 carbon atoms and an alkylene group having 1 to 14 carbon atoms, with the number of carbon atoms of the sum of these groups being 7 to 20. More preferred examples of $R^3$ include hydrogen and an alkyl having 1 to 20 carbon atoms. Further preferred examples of $R^3$ include hydrogen, methyl, and ethyl. Preferred examples, more preferred example and further preferred examples of $R^4$ are the same as the preferred examples, more preferred examples and further preferred examples of $R^3$, respectively, except that hydrogen is excluded from the respective examples. A most preferred example of $R^3$ and $R^4$ is methyl. $X^1$ is a halogen, and examples thereof include chlorine, bromine, and iodine.

As the initiating group for the atom transfer radical polymerization, chlorine and bromine are most preferred.

As a polymerization method using a halogenated sulfonyl group as an initiating group for radical polymerization, an atom transfer radical polymerization method is known. In this method, a metal complex containing, as a central metal, an element belonging to the Group 8, the Group 9, the Group 10, or the Group 11 of the Periodic Table is used as a catalyst. In this atom transfer radical polymerization, it is known that a halogenated sulfonyl has an excellent polymerization initiating ability. It is also well known that this polymerization proceeds in a living polymerization way. That is, the silicon compound having a halogenated sulfonyl according to the invention has an excellent polymerization initiating ability in the presence of a transition metal catalyst so that it can continue to keep living polymerization properties. Moreover, the silicon compound having a halogenated sulfonyl according to the invention can initiate polymerization for any radical polymerizable monomers. In particular, the silicon compound having a halogenated sulfonyl according to the invention can reveal excellent living polymerization properties for (meth)acrylic acid derivatives.

Incidentally, since the halogenated sulfonyl group has strong electrophilicity, by making a nucleic reagent of every kind act on the silicon compound having a halogenated sulfonyl group according to the invention, a variety of derivatives can be synthesized. For example, it is possible to achieve conversion into sulfonic acid by hydrolysis under an acidic condition, conversion into sulfonic acid by hydrolysis and subsequent conversion into a sulfonic acid salt by a treatment with sodium hydroxide, conversion into a sulfonic acid ester by a treatment with an alcohol with every kind under a basic condition, or conversion into a sulfonic acid amide by a treatment with ammonia or an amine. In view of these characteristic features, the silicon compound of the invention can also be utilized as a protective group. Also, a part of sulfonic acid amide derivatives can be utilized as a sulfa drug as, for example, an antibacterial drug. Furthermore, the silicon compound can achieve conversion into a mercapto group by using a reducing agent of every kind such as lithium aluminum hydride and can achieve derivation into an aromatic sulfone by using an aromatic Grignard reagent of every kind. That is, this silicon compound can be effectively utilized as not only an attribute as a polymerization initiator but also a useful intermediate for a variety of organic syntheses.

A preferred example of the group having a halogenated sulfonyl is a group represented by Formula (2-2).

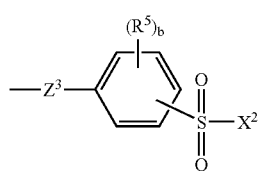

(2-2)

In Formula (2-2), the respective symbols have the following meanings. $Z^3$ is an alkylene having 2 to 10 carbon atoms in which arbitrary —$CH_2$— may be replaced by —O—, —COO—, or —OCO—. $R^5$ is an alkyl having 1 to 3 carbon atoms; and b is an integer of 0 to 2. $X^2$ is a halogen; the bonding position of —$SO_2X^2$ on the benzene ring is an ortho-position, a meta-position, or a para-position with respect to the bonding position of $Z^3$. The bonding position of $R^5$ is an arbitrary position excluding the respective bonding positions of $Z^3$ and —$SO_2X^2$.

A preferred example of the silicon compound having a halogenated sulfonyl according to the invention is a compound represented by Formula (1-2).

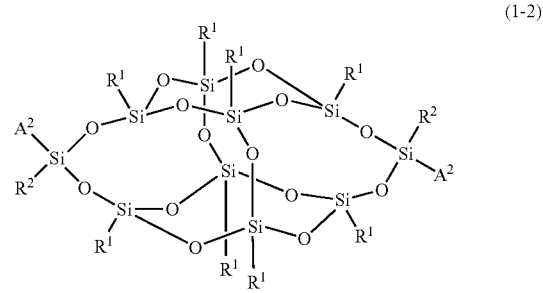

(1-2)

In Formula (1-2), $R^1$ and $R^2$ have the same meanings as those in Formula (1), respectively. $A^2$ is a group represented by Formula (2-2-1).

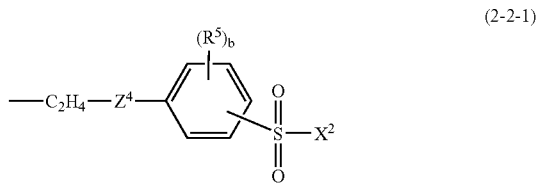

(2-2-1)

In Formula (2-2-1), —$C_2H_4$-$Z^4$- is a preferred example of $Z^3$ in Formula (2-2). $Z^4$ is a single bond or an alkylene having 1 to 3 carbon atoms. A most preferred example of $Z^4$ is a single bond. The bonding position of —$SO_2X^2$ on the benzene ring is an ortho-position, a meta-position, or a para-position with respect to the bonding position of $Z^3$. $R^5$ is an alkyl having 1 to 3 carbon atoms. b is 0, 1 or 2, and most preferably 0. The bonding position of $R^5$ is an arbitrary position excluding the respective bonding positions of $Z^3$ and —$SO_2X^2$. $X^2$ is a halogen, and examples thereof include chlorine, bromine and iodine. As the initiating group for the atom transfer radical polymerization, chlorine and bromine are most preferred.

As a polymerization method using a haloalkylphenyl as an initiating group for radical polymerization, an atom transfer radical polymerization method is known. In this method, a metal complex containing, as a central metal, an element belonging to the Group 8, the Group 9, the Group 10, or the Group 11 of the Periodic Table is used as a catalyst. In this atom transfer radical polymerization, it is known that a haloalkylphenyl has an excellent polymerization initiating ability. It is also well known that this polymerization proceeds in a living polymerization way. That is, the silicon compound having a haloalkylphenyl according to the invention has an excellent polymerization initiating ability in the presence of a transition metal complex so that it can continue to keep living polymerization properties. Moreover, the silicon compound having a haloalkylphenyl according to the invention can initiate polymerization for any radical polymerizable monomers. In particular, the silicon compound having a haloalkylphenyl according to the invention can reveal excellent living polymerization properties for styrene based derivatives.

Incidentally, since the haloalkylphenyl has strong electrophilicity, it is possible to introduce an amino group, a hydroxyl group, a mercapto group, etc. into the silicon compound having a haloalkylphenyl according to the invention by utilizing a variety of nucleophilic reagents. That is, this silicon compound can be effectively utilized as a useful intermediate.

A preferred example of the group having a haloalkylphenyl is a group represented by Formula (2-3).

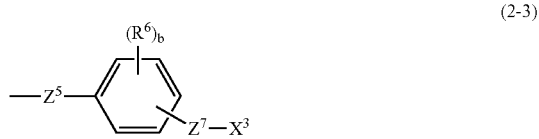

(2-3)

In Formula (2-3), the respective symbols have the following meanings. $Z^5$ is an alkylene having 2 to 10 carbon atoms in which arbitrary —CH$_2$— may be replaced by —O—, —COO—, or —OCO—. $R^6$ is an alkyl having 1 to 3 carbon atoms; and b is an integer of 0 to 2. $Z^7$ is an alkylene having 1 to 3 carbon atoms in which arbitrary —CH$_2$— may be replaced by —O—. $X^3$ is a halogen. The bonding position of $Z^7$ on the benzene ring is a meta-position or a para-position with respect to the bonding position of $Z^5$; and the bonding position of $R^6$ is an arbitrary position excluding the respective bonding positions of $Z^5$ and $Z^7$.

A preferred example of the silicon compound having a haloalkylphenyl according to the invention is a compound represented by Formula (1-3).

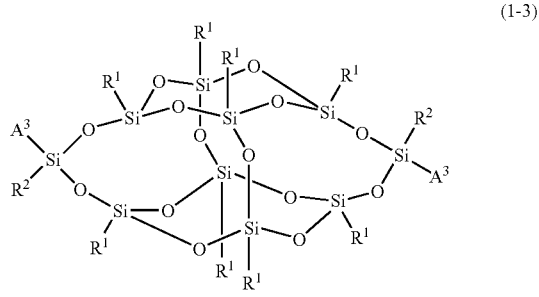

(1-3)

In Formula (1-3), $R^1$ and $R^2$ have the same meanings as those in Formula (1), respectively. $A^3$ is a group represented by Formula (2-3-1).

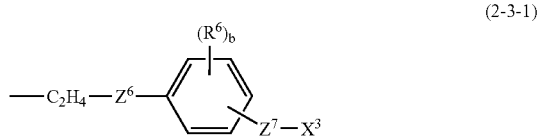

(2-3-1)

In Formula (2-3-1), —C$_2$H$_4$-Z$^6$- is a preferred example of $Z^5$ in Formula (2-3). $Z^6$ is a single bond or an alkylene having 1 to 8 carbon atoms in which arbitrary —CH$_2$— may be replaced by —O—, —COO—, or —OCO—. Preferred examples of $Z^6$ include a single bond, —CH$_2$—, —COO—, —COOCH$_2$—, —CH$_2$OCO—, —CH$_2$O—, and —CH$_2$OCH$_2$—. A most preferred example of $Z^6$ is a single bond. $R^6$ is an alkyl having 1 to 3 carbon atoms. b is an integer of 0 to 2 and most preferably 0. $Z^7$ is an alkylene having 1 to 3 carbon atoms in which arbitrary —CH$_2$— may be replaced by —O—. A most preferred example of $Z^7$ is —CH$_2$—. $X^3$ is a halogen, and examples thereof include chlorine, bromine, and iodine. As the initiating group for the atom transfer radical polymerization, chlorine and bromine are most preferred. The bonding position of $Z^7$ on the benzene ring is a meta-position or a para-position with respect to the bonding position of $Z^6$; and the bonding position of $R^6$ is an arbitrary position excluding the respective bonding positions of $Z^6$ and $Z^7$.

As a photopolymerization method using a dithiocarbamate group as a polymerization initiating group, a photoiniferter (photo initiator-transfer agent-terminator) polymerization method is known. In the photoiniferter polymerization, it is well known that the dithiocarbamate group causes radical dissociation by light and has excellent polymerization initiating ability and sensitization ability. It is also well known that this photopolymerization proceeds in a living polymerization way. Accordingly, the silicon compound having a dithiocarbamate group according to the invention can continue to keep a polymerization initiating ability so far as light is irradiated and has a photopolymerization initiating ability for any radical polymerizable monomers. In particular, it is possible to reveal excellent living polymerization properties for (meth)acrylic acid derivatives. Since the dithiocarbamate group has radiation resistance, pharmacological activity such as a herbicidal effect, a complex forming ability, hydrophilicity, and the like in addition to characteristics as its photopolymerization initiating group, it is also possible to effectively utilize these characteristics.

A preferred example of the group having a dithiocarbamate group is a group represented by Formula (2-4).

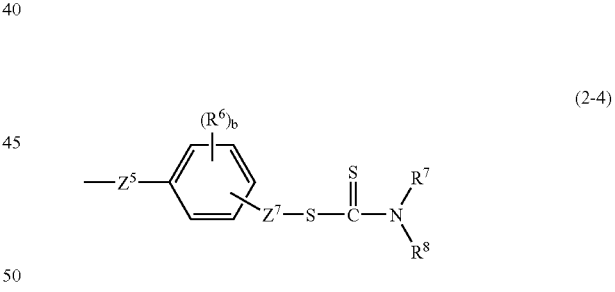

(2-4)

In Formula (2-4), the respective symbols have the following meanings. $Z^5$ is an alkylene having 2 to 10 carbon atoms in which arbitrary —CH$_2$— may be replaced by —O—, —COO—, or —OCO—. $R^6$ is an alkyl having 1 to 3 carbon atoms; and b is an integer of 0 to 2. $Z^7$ is an alkylene having 1 to 3 carbon atoms in which arbitrary —CH$_2$— may be replaced by —O—. $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N. The bonding position of $Z^7$ on the benzene ring is a meta-position or a para-positive with respect to the bonding position of $Z^5$; and the bonding position of $R^6$ is an arbitrary position excluding the respective bonding positions of $Z^5$ and $Z^7$.

A preferred example of the silicon compound having a dithiocarbamate group according to the invention is a compound represented by Formula (1-4).

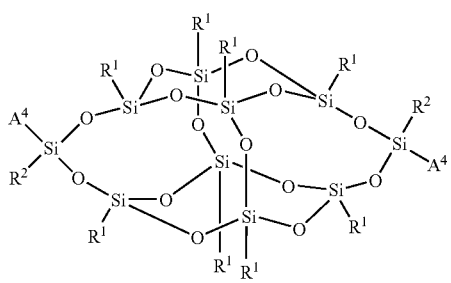
(1-4)

In Formula (1-4), $R^1$ and $R^2$ have the same meanings as those in Formula (1), respectively; and $A^4$ is a group represented by Formula (2-4-1).

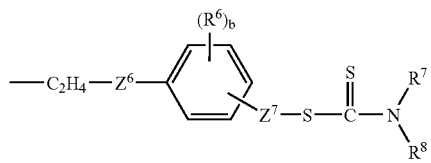
(2-4-1)

In Formula (2-4-1), $Z^6$, $R^6$, $Z^7$, and b have the same meanings as those in Formula (2-3-1), respectively; and the bonding positions of $Z^7$ and $Z^6$ on the benzene ring are the same as $Z^7$ and $Z^6$ in Formula (2-3-1), respectively. $R^7$ and $R^8$ are each independently hydrogen, an alkyl having 1 to 12 carbon atoms, a cycloalkyl having 5 to 10 carbon atoms, or an aryl having 6 to 10 carbon atoms. Besides hydrogen, examples of $R^7$ or $R^8$ include methyl, ethyl, propyl, isopropyl, butyl, isobutyl, pentyl, 2-methylbutyl, hexyl, 2-methylpentyl, heptyl, 2-methylhexyl, octyl, 2-methylheptyl, 2-ethylhexyl, decyl, phenyl, cyclopentyl, and cyclohexyl. Both $R^7$ and $R^8$ may be each one of these groups. One of $R^7$ and $R^8$ may be one of these groups, with the other being hydrogen.

$R^7$ and $R^8$ may be bound to each other to form a ring together with N. In this case, examples of the dithiocarbamate group include an N-cyclotrimethylenedithiocarbamate group, an N-cyclotetramethylenedithiocarbamate group, an N-cyclopentamethylenedithiocarbamate group, an N-cyclohexamethylenedithiocarbamate group, an N-cycloheptamethylenedithiocarbamate group, and an N-cyclooctamethylenedithiocarbamate group. The dithiocarbamate group is preferably an N,N-dimethyldithiocarbamate group, an N,N-diethyldithiocarbamate group, an N-methyldithiocarbamate group, and an N-ethyldithiocarbamate group. Of these, an N,N-diethyldithiocarbamate group is most preferred.

Next, a part of specific examples of the silicon compound of the invention will be given in the following Tables 2 to 5 by using symbols as shown in Table 1.

TABLE 1

| Formula | Symbol |
|---|---|
| —CH₃ | Me |
| —C₂H₅ | Et |
| (phenyl) | Ph |
| —Cl | CL |
| —Br | BR |
| (S-C(=S)-N(C₂H₅)₂) | Q |
| Single bond | — |
| —CH₂— | C1 |
| —C₂H₄— | C2 |
| —C₃H₆— | C3 |
| (para-phenylene) | Phe |

Examples of the compound (1-1) are shown in Table 2 while using Formula (1-1-1). The formula (1-1-1) is a formula of the case where in Formula (1-1), $R^1$ is phenyl and $R^2$ is —CH₃.

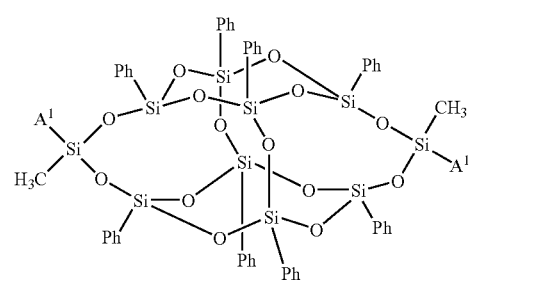
(1-1-1)

In this formula, $A^1$ is a group represented by Formula (2-10 1-1).

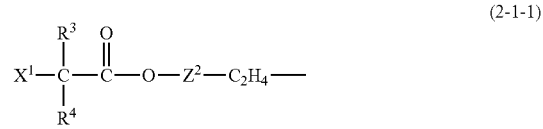
(2-1-1)

The respective symbols in Formula (2-1-1) have the meanings as described above.

TABLE 2

| No. | $Z^2$ | $R^3$ | $R^4$ | $X^1$ | Formula (1-1-1) |
|---|---|---|---|---|---|
| 1 | C1 | H | Me | CL | (Ph—)$_8$(CL—CH(Me)—COO—C3—Si(Me)—)$_2$Si$_8$O$_{14}$ |
| 2 | C2 | H | Me | CL | (Ph—)$_8$(CL—CH(Me)—COO—C4—Si(Me)—)$_2$Si$_8$O$_{14}$ |
| 3 | C3 | H | Me | CL | (Ph—)$_8$(CL—CH(Me)—COO—C5—Si(Me)—)$_2$Si$_8$O$_{14}$ |
| 4 | C2—O—C1 | H | Me | CL | (Ph—)$_8$(CL—CH(Me)—COO—C2—O—C3—Si(Me)—)$_2$Si$_8$O$_{14}$ |
| 5 | C1 | Me | Me | CL | (Ph—)$_8$(CL—C(Me)$_2$—COO—C3—Si(Me)—)$_2$Si$_8$O$_{14}$ |
| 6 | C2 | Me | Me | CL | (Ph—)$_8$(CL—C(Me)$_2$—COO—C4—Si(Me)—)$_2$Si$_8$O$_{14}$ |
| 7 | C3 | Me | Me | CL | (Ph—)$_8$(CL—C(Me)$_2$—COO—C5—Si(Me)—)$_2$Si$_8$O$_{14}$ |
| 8 | C2—O—C1 | Me | Me | CL | (Ph—)$_8$(CL—C(Me)$_2$—COO—C2—O—C3—Si(Me)—)$_2$Si$_8$O$_{14}$ |
| 9 | C1 | Et | Et | CL | (Ph—)$_8$(CL—C(Et)$_2$—COO—C3—Si(Me)—)$_2$Si$_8$O$_{14}$ |
| 10 | C2 | Et | Et | CL | (Ph—)$_8$(CL—C(Et)$_2$—COO—C4—Si(Me)—)$_2$Si$_8$O$_{14}$ |
| 11 | C3 | Et | Et | CL | (Ph—)$_8$(CL—C(Et)$_2$—COO—C5—Si(Me)—)$_2$Si$_8$O$_{14}$ |
| 12 | C2—O—C1 | Et | Et | CL | (Ph—)$_8$(CL—C(Et)$_2$—COO—C2—O—C3—Si(Me)—)$_2$Si$_8$O$_{14}$ |
| 13 | C1 | H | Me | BR | (Ph—)$_8$(BR—CH(Me)—COO—C3—Si(Me)—)$_2$Si$_8$O$_{14}$ |
| 14 | C2 | H | Me | BR | (Ph—)$_8$(BR—CH(Me)—COO—C4—Si(Me)—)$_2$Si$_8$O$_{14}$ |
| 15 | C3 | H | Me | BR | (Ph—)$_8$(BR—CH(Me)—COO—C5—Si(Me)—)$_2$Si$_8$O$_{14}$ |
| 16 | C2—O—C1 | H | Me | BR | (Ph—)$_8$(BR—CH(Me)—COO—C2—O—C3—Si(Me)—)$_2$Si$_8$O$_{14}$ |
| 17 | C1 | Me | Me | BR | (Ph—)$_8$(BR—C(Me)$_2$—COO—C3—Si(Me)—)$_2$Si$_8$O$_{14}$ |
| 18 | C2 | Me | Me | BR | (Ph—)$_8$(BR—C(Me)$_2$—COO—C4—Si(Me)—)$_2$Si$_8$O$_{14}$ |
| 19 | C3 | Me | Me | BR | (Ph—)$_8$(BR—C(Me)$_2$—COO—C5—Si(Me)—)$_2$Si$_8$O$_{14}$ |
| 20 | C2—O—C1 | Me | Me | BR | (Ph—)$_8$(BR—C(Me)$_2$—COO—C2—O—C3—Si(Me)—)$_2$Si$_8$O$_{14}$ |
| 21 | C1 | Et | Et | BR | (Ph—)$_8$(BR—C(Et)$_2$—COO—C3—Si(Me)—)$_2$Si$_8$O$_{14}$ |
| 22 | C2 | Et | Et | BR | (Ph—)$_8$(BR—C(Et)$_2$—COO—C4—Si(Me)—)$_2$Si$_8$O$_{14}$ |
| 23 | C3 | Et | Et | BR | (Ph—)$_8$(BR—C(Et)$_2$—COO—C5—Si(Me)—)$_2$Si$_8$O$_{14}$ |
| 24 | C2—O—C1 | Et | Et | BR | (Ph—)$_8$(BR—C(Et)$_2$—COO—C2—O—C3—Si(Me)—)$_2$Si$_8$O$_{14}$ |

Examples of the compound (1-2) are shown in Table 3 while using Formula (1-2-1). The formula (1-2-1) is a formula of the case where in Formula (1-2), $R^1$ is phenyl, $R^2$ is —CH$_3$ and $A^2$ is a group represented by Formula (2-2-2).

TABLE 3

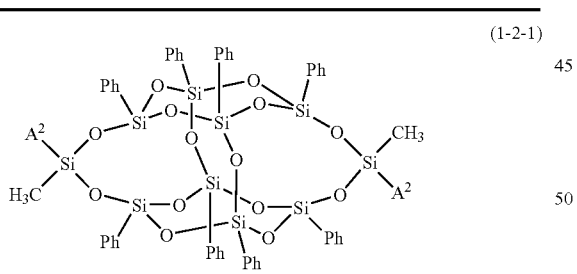
(1-2-1)

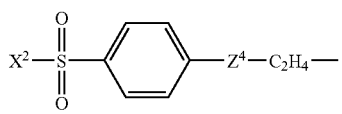
(2-2-2)

| No. | $Z^4$ | $X^2$ | Formula (1-2-1) |
|---|---|---|---|
| 1 | — | CL | (Ph—)$_8$(CL—SO$_2$—Phe—C2—Si(Me)—)$_2$Si$_8$O$_{14}$ |
| 2 | C1 | CL | (Ph—)$_8$(CL—SO$_2$—Phe—C3—Si(Me)—)$_2$Si$_8$O$_{14}$ |
| 3 | C2 | CL | (Ph—)$_8$(CL—SO$_2$—Phe—C4—Si(Me)—)$_2$Si$_8$O$_{14}$ |
| 4 | C3 | CL | (Ph—)$_8$(CL—SO$_2$—Phe—C5—Si(Me)—)$_2$Si$_8$O$_{14}$ |
| 5 | — | BR | (Ph—)$_8$(BR—SO$_2$—Phe—C2—Si(Me)—)$_2$Si$_8$O$_{14}$ |
| 6 | C1 | BR | (Ph—)$_8$(BR—SO$_2$—Phe—C3—Si(Me)—)$_2$Si$_8$O$_{14}$ |

TABLE 3-continued

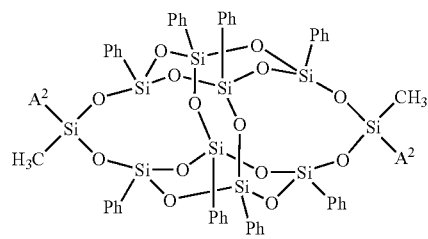
(1-2-1)

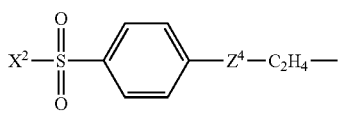
(2-2-2)

| No. | $Z^4$ | $X^2$ | Formula (1-2-1) |
|---|---|---|---|
| 7 | C2 | BR | (Ph—)$_8$(BR—SO$_2$—Phe—C4—Si(Me)—)$_2$Si$_8$O$_{14}$ |
| 8 | C3 | BR | (Ph—)$_8$(BR—SO$_2$—Phe—C5—Si(Me)—)$_2$Si$_8$O$_{14}$ |

Examples of the compound (1-3) are shown in Table 4 while using Formula (1-3-1). The formula (1-3-1) is a formula of the case where in Formula (1-3), $R^1$ is phenyl, $R^2$ is —CH$_3$ and $A^3$ is a group represented by Formula (2-3-2).

TABLE 4

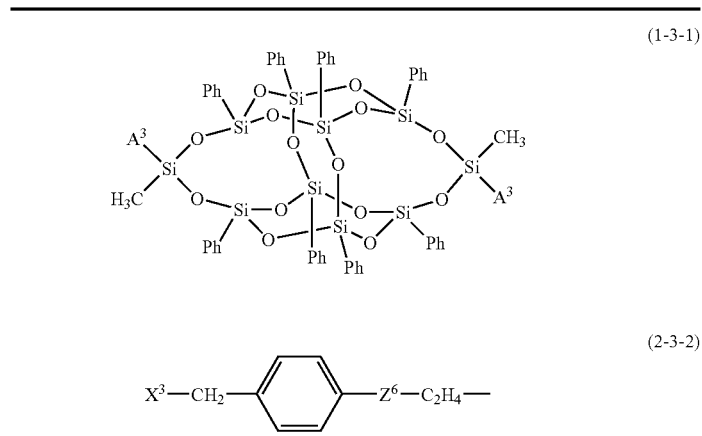

(1-3-1)

(2-3-2)

| No. | $Z^6$ | $X^3$ | Formula (1-3-1) |
|---|---|---|---|
| 1 | — | CL | (Ph—)$_8$(CL—C1—Phe—C2—Si(Me)—)$_2$Si$_8$O$_{14}$ |
| 2 | C1 | CL | (Ph—)$_8$(CL—C1—Phe—C3—Si(Me)—)$_2$Si$_8$O$_{14}$ |
| 3 | OCO | CL | (Ph—)$_8$(CL—C1—Phe—OCO—C2—Si(Me)—)$_2$Si$_8$O$_{14}$ |
| 4 | C1—OCO | CL | (Ph—)$_8$(CL—C1—Phe—C1—OCO—C2—Si(Me)—)$_2$Si$_8$O$_{14}$ |
| 5 | COO—C1 | CL | (Ph—)$_8$(CL—C1—Phe—COO—C3—Si(Me)—)$_2$Si$_8$O$_{14}$ |
| 6 | — | BR | (Ph—)$_8$(BR—C1—Phe—C2—Si(Me)—)$_2$Si$_8$O$_{14}$ |
| 7 | C1 | BR | (Ph—)$_8$(BR—C1—Phe—C3—Si(Me)—)$_2$Si$_8$O$_{14}$ |
| 8 | OCO | BR | (Ph—)$_8$(BR—C1—Phe—OCO—C2—Si(Me)—)$_2$Si$_8$O$_{14}$ |
| 9 | C1—OCO | BR | (Ph—)$_8$(BR—C1—Phe—C1—OCO—C2—Si(Me)—)$_2$Si$_8$O$_{14}$ |
| 10 | COO—C1 | BR | (Ph—)$_8$(BR—C1—Phe—COO—C3—Si(Me)—)$_2$Si$_8$O$_{14}$ |

Examples of the compound (1-4) are shown in Table 5 while using Formula (1-4-1). The formula (1-4-1) is a formula of the case where in Formula (1-4), $R^1$ is phenyl, $R^2$ is —CH$_3$ and $A^3$ is a group represented by Formula (2-4-2).

Incidentally, it should not be construed that the compound (1-1), the compound (1-2), the compound (1-3), and the compound (1-4) are limited to the examples as described in Tables 2 to 5.

TABLE 5

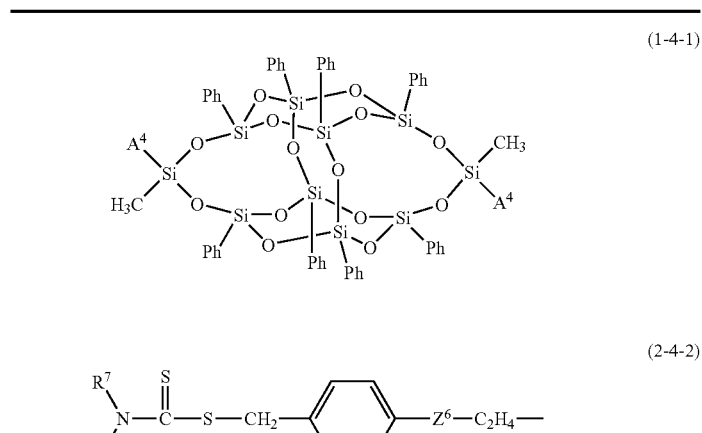

(1-4-1)

(2-4-2)

| No. | $Z^6$ | Formula (1-3-1) |
|---|---|---|
| 1 | — | (Ph—)$_8$(Q—C1—Phe—C2—Si(Me)—)$_2$Si$_8$O$_{14}$ |
| 2 | C1 | (Ph—)$_8$(Q—C1—Phe—C3—Si(Me)—)$_2$Si$_8$O$_{14}$ |
| 3 | OCO | (Ph—)$_8$(Q—C1—Phe—OCO—C2—Si(Me)—)$_2$Si$_8$O$_{14}$ |
| 4 | C1—OCO | (Ph—)$_8$(Q—C1—Phe—C1—OCO—C2—Si(Me)—)$_2$Si$_8$O$_{14}$ |
| 5 | COO—C1 | (Ph—)$_8$(Q—C1—Phe—COO—C3—Si(Me)—)$_2$Si$_8$O$_{14}$ |

Next, the production process of the compound (1-1) among the silicon compounds of the invention, will be hereunder described.

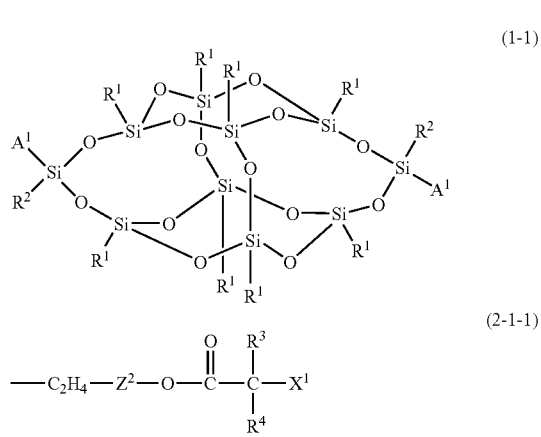

(1-1)

(2-1-1)

In Formula (1-1), $A^1$ is a group represented by Formula (2-1-1). $R^1$ and $R^2$ and the respective symbols in Formula (2-1-1) have the meanings as described above.

A preferred raw material which is used in the invention is the following compound (3-1).

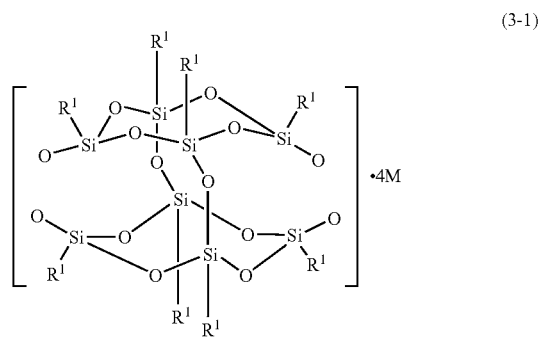

(3-1)

In Formula (3-1), $R^1$ has the same meaning as $R^1$ in Formula (1); and M is a monovalent alkali metal atom. Preferred examples of the alkali metal include sodium and potassium. A most preferred example of the alkali metal is sodium.

The compound (3-1) is obtained by hydrolyzing and condensing a silane compound having three hydrolyzable groups in the presence of an organic solvent, water and an alkali metal hydroxide. According to this method, the compound (3-1) can be produced in a high yield within a short period of time (see WO 03/024870). In producing the compound (3-1), by using at least two silane compounds each having three hydrolyzable groups, the compound (3-1) wherein in Formula (3-1), eight $R^1$s are constituted of at least two different groups can be obtained. Since the compound (3-1) exhibits high reactivity, if this compound is used as the raw material, its derivative can be easily synthesized in a high yield. For example, by reacting the compound (3-1) and an Si—H functional organodichlorosilane, an Si—H functional silsesquioxane derivative can be produced.

The Si—H functional organodichlorosilane is represented by Formula (4). $R^2$ has the same meaning as $R^2$ in Formula (1) and is an alkyl having 1 to 8 carbon atoms, phenyl, or cyclohexyl. An especially preferred example of $R^2$ is methyl.

That is, an especially preferred example of the compound (4) is methyldichlorosilane. The following compound (5) is obtained by reacting the compound (3-1) and the following compound (4).

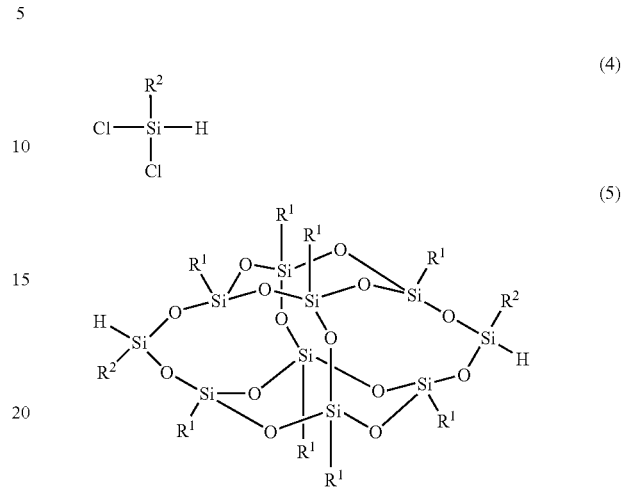

(4)

(5)

For the purpose of synthesizing the compound (5) by reacting the compound (3-1) and the compound (4), a method of utilizing nucleophilic substitution can be employed. This method is described in, for example, *J. Am. Chem. Soc.*, 112 (1990), 1931. A condition for selecting a solvent which is used for this nucleophilic substitution reaction is laid on the matters that the solvent is not reactive with the compound (3-1) and the compound (4) and that the solvent is thoroughly dehydrated. Examples of the solvent include hexane, heptane, benzene, toluene, diethyl ether, tetrahydrofuran, ethyl acetate, and chloroform. Most preferred examples of the solvent include thoroughly dehydrated tetrahydrofuran and thoroughly dehydrated toluene. These solvents may be used as a mixture thereof. A preferred amount of the compound (4) to be used is 1 to 50 times in terms of an equivalent ratio to the compound (3-1). A more preferred amount of the compound (4) to be used is 1 to 25 times in terms of an equivalent ratio to the compound (3-1). In this reaction, triethylamine may be used as a catalytic role for rapidly achieving progress of the reaction. In the case of using trielhylamine, the triethylamine is preferably used in an amount of 0.05 to 50 times in terms of an equivalent ratio to the compound (3-1).

The reaction temperature is not particularly limited so far as side reactions do not concur and the nucleophilic substitution reaction quantitatively proceeds. However, the raw materials may be charged under a low temperature condition, for example, on an ice bath. The subsequent reaction may be carried out under a room temperature condition or a heating condition. Concretely, the reaction temperature is in the range of 0 to 150° C., and more preferably 0 to 50° C. The reaction time is not particularly limited so far as it is sufficient for advancing the nucleophilic substitution reaction quantitatively. Usually, the desired silicon compound can be obtained for 1 to 15 hours.

In addition, since the compound (3-1) has —ONa as a reaction active group, even if a chlorosilane is used in a synthesis reaction of the derivative, it does not generate hydrogen chloride. Accordingly, it is possible to make the reaction operation easy and to carry out the reaction completely.

Another preferred raw material which is used in the invention is the following compound (3-2).

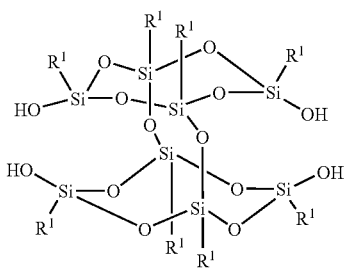
(3-2)

In Formula (3-2), $R^1$ has the same meaning as $R^1$ in Formula (1). Such a compound is easily obtained by reacting an acid and the compound (3-1). At this time, in the reaction with an acid, an organic solvent can be used, if desired. A method in which the compound (3-1) and an organic solvent are mixed and this mixture is added dropwise to the acid, thereby advancing the reaction can be employed.

A condition for selecting the organic solvent which is used in this reaction is laid on only the matter that the solvent does not hinder progress of the reaction. Examples of this organic solvent include aliphatic hydrocarbons (for example, hexane and heptane), aromatic hydrocarbons (for example, benzene, toluene, and xylene), ethers (for example, diethyl ether, tetrahydrofuran, and dioxane), halogenated hydrocarbons (for example, methylene chloride and carbon tetrachloride), and acetic acid esters (for example, methyl acetate, ethyl acetate, and butyl acetate). More preferred examples of the organic solvent include tetrahydrofuran and ethyl acetate.

When mixed in the solvent, a preferred proportion of the compound (3-1) is 0.0005 to 0.50 in terms of a weight ratio to the solvent. When this proportion is not more than 0.50, the concentration of a salt as a by-product can be lowered, and therefore, such is advantageously in advancing the reaction. When the proportion is 0.0005 or more, good volume efficiency is exhibited, and therefore, such is preferred in view of the costs. The proportion is preferably 0.01 to 0.10.

The acid which is used in this reaction is a proton donator (Brønsted acid) and is not particularly limited so far as it is reactive with the compound (3-1) so that the compound (3-2) can be obtained. Examples of the acid include cyanic acid, isocyanic acid, thiocyanic acid, isothiocyanic acid, nitric acid, nitrous acid, sulfuric acid, sulfurous acid, carbonic acid, hydrochloric acid, hydrobromic acid, phosphoric acid, boric acid, formic acid, acetic acid, propionic acid, butyric acid, stearic acid, oxalic acid, malonic acid, succinic acid, adipic acid, acrylic acid, methacrylic acid, oleic acid, maleic acid, chloroformic acid, chloroacetic acid, trifluoroacetic acid, cyclohexanecarboxylic acid, pivalic acid, benzoic acid, toluic acid, naphthoic acid, phthalic acid, cinnamic acid, nicotinic acid, thiophenecarboxylic acid, S-thioacetic acid, dithioacetic acid, S-thiobenzoic acid, dithiobenzoic acid, thiocarbonic acid, trithiocarbonic acid, xanthogenic acid, methanesulfonic acid, benzenesulfonic acid, p-toluenesulfonic acid, phenylphosphonic acid, and diphenylphosphinic acid. Of these, organic acids are preferred; carboxylic acids are more preferred; and acetic acid is most preferred.

When such an acid is used in an amount of 4 times by mole or more for the compound (3-1), the reaction can be completed. When the proportion of the acid to be used falls within this range, a possibility that an undesired side reaction is caused is low and it is enough that the amount of a neutralizing agent to be used in a post-treatment step is small, and therefore, such is efficient. In addition, the proportion of the acid to be used is preferably 4 times by mole to 10 times by mole, and more preferably 4 times by mole to 5 times by mole for the compound (3-1).

The reaction temperature may be room temperature. For the purpose of promoting the reaction, heating may be carried out, if desired. Alternatively, for the purpose of controlling the heat generation due to the reaction or preventing undesired reactions from occurring, cooling may be carried out, if desired.

The reaction time is 0.5 to 8 hours. However, since the reaction time is generally influenced by not only reactivity of the raw materials but also the concentration of the raw materials, the reaction temperature, the shape of a device (stirring efficiency), the shape of a product or by-products, and the like, it is not meant that this range of the reaction time limits the invention.

Likewise the case of the compound (3-1), the compound (5) can be synthesized by reacting the compound (3-2) and the compound (4) while utilizing nucleophilic substitution. When the compound (4) is reacted with all Si—OH (silanol) groups of the compound (3-2), a preferred amount of the compound (4) to be used is 3 to 15 times in terms of an equivalent ratio to the compound (3-2). At the time of this reaction, since hydrogen chloride is generated due to the reaction between hydrogen of the silanol and chlorine of the chlorosilane, this hydrogen chloride must be removed from the reaction system. Though a method for removing hydrogen chloride is not limited, it is most preferred to use triethylamine. A preferred amount of triethylamine to be used is 3 to 15 times in terms of an equivalent ratio to the compound (3-2). A preferred solvent to be used in this reaction is the same as in the case of the reaction using the compound (3-1). A preferred reaction temperature is a temperature at which side reactions do not concur and the nucleophilic substitution reaction quantitatively proceeds. However, it is most preferred that the raw materials are charged under a low temperature condition, for example, on an ice bath, and the subsequent reaction may be carried out under a room temperature condition. The reaction time is not particularly limited so far as it is sufficient for advancing the nucleophilic substitution reaction quantitatively. Usually, the desired silicon compound can be obtained for 10 to 15 hours.

In synthesizing the silicon compound of the invention, it is preferred to employ a hydrosilylation reaction method using the foregoing compound (5). That is, this reaction is a reaction between the compound (5) and the following compound (6) in the presence of a transition metal catalyst.

 (6)

In this formula, $Z^2$ has the same meaning as $Z^2$ in Formula (2-1-1).

Examples of the transition metal catalyst which is used include platinum, rhodium, iridium, ruthenium, palladium, molybdenum, iron, cobalt, nickel, and manganese. Of these, a platinum catalyst is more preferred. Such a catalyst can be used as a homogeneous catalyst dissolved in a solvent or a solid catalyst supported on carbon, silica, or the like. The catalyst may be used in a form that a phosphine, an amine, potassium acetate, or the like is coexistent. A preferred amount of the transition metal catalyst to be used is $1 \times 10^{-6}$ to $1 \times 10^{-2}$ moles as a transition metal catalyst atom per mole of the Si—H group in the compound (5).

An amount of the compound (6) to be used is preferably 1 to 5 times in terms of an equivalent ratio to the Si—H group in the compound (5). Since the hydrosilylation reaction substantially quantitatively proceeds, it is not meaningful so much to make this equivalent ratio high. However, since an effect for shortening the reaction time can be expected, an adverse influence is laid on only cost efficiency due to the use of a large amount of the compound (6). On the other hand, in the case where it is intended to leave a part of the Si—H groups in an unreacted state, it is only required to make the foregoing equivalent ratio lower than 1. In this way, a compound represented by Formula (7) is obtained.

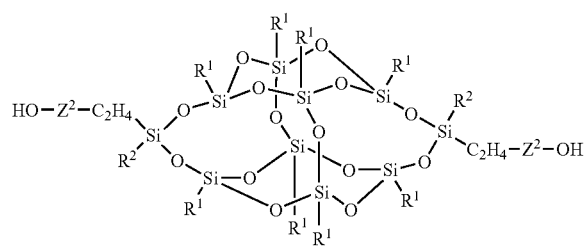

(7)

In Formula (7), $R^1$ and $R^2$ have the same meanings as those in Formula (1), respectively; and $Z^2$ has the same meaning as $Z^2$ in Formula (6).

A preferred reaction temperature in the hydrosilylation reaction is not higher than the boiling point of the solvent to be used. The compound (6) is a compound having a polymerizable unsaturated bond. For the purpose of preventing spontaneous polymerization of this compound during the hydrosilylation reaction from occurring, a preferred reaction temperature is 20 to 80° C. For the purpose of suppressing this polymerization reaction, a polymerization inhibitor such as phenol derivatives, phenothiazine derivatives, and N-nitrosophenylamine salt derivatives may be used. A most preferred polymerization inhibitor is 4-tert-butylpyrocatechol. A preferred amount of the polymerization inhibitor to be used is in the range of 1 to 100,000 ppm, and more preferably 100 to 20,000 ppm on the basis of the total weight of the reaction solution.

The organic solvent which is used in this hydrosilylation reaction is not particularly limited so far as it readily dissolves the raw materials therein without being reacted therewith. Preferred examples of the organic solvent include aliphatic hydrocarbons (for example, hexane and heptane), aromatic hydrocarbons (for example, toluene and xylene), and cyclic ethers (for example, tetrahydrofuran and dioxane). When dissolution properties of the compound (5) are taken into consideration, toluene is most preferred. For the purpose of controlling activity of the catalyst, an alcohol such as 2-propanol may be added.

The compound (7) can also be produced by the following method. First of all, the compound (5) and an alkenyl group-containing compound (6-T) are subjected to a hydrosilylation reaction in toluene in the presence of a platinum-divinyltetramethyldisiloxane complex, thereby producing a compound (7-T). Next, the trimethylsilyl group as a protective group is removed by alcoholysis using a large excess of methanol at room temperature or under a condition of slightly heating (40° C.), thereby deriving the compound (7-T) into the compound (7).

(6-T)

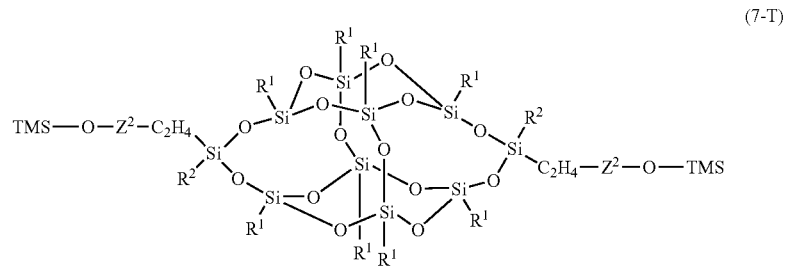

(7-T)

In these formulae, $Z^2$ has the same meaning as $Z^2$ in Formula (6); $R^1$ and $R^2$ have the same meanings as those in Formula (7), respectively; and TMS is a trimethylsilyl group.

Then, the compound (7) is reacted with a compound (8) in which a halogen is bound on carbon at the α-position to obtain the compound (1-1).

(8)

In Formula (8), $R^3$, $R^4$, and $X^1$ have same meanings as those in Formula (2-1-1); and X is a halogen. Examples of this halogen include chlorine, bromine, and iodine. Of these, chlorine and bromine are preferred. $X^1$ may be the same as or different from X.

In this reaction, a hydrogen halide which is formed as a by-product induce side reactions such as dehydration and addition to a double bond site. Thus, in order to remove this, the reaction is carried out in the co-presence of an organic base. Examples of the organic base include pyridine, dimethylaniline, triethylamine, and tetramethylurea. Other organic bases may be used so far as they can suppress the side reactions and rapidly advance the reaction. A most preferred example of the organic base is triethylamine. Though this reaction is a nucleophilic substitution reaction which quantitatively proceeds, an amount of the compound (8) to be used is preferably 1 to 10 times in terms of an equivalent ratio to the compound (7). By making the amount of the compound (8) to be used high, it is possible to react the compound (7) entirely and to shorten the reaction time.

This reaction is usually carried out in an inert gas atmosphere such as an argon gas and a nitrogen gas by using a dry organic solvent which is inert for the raw materials. Examples of the organic solvent include cyclic ethers (for example, THF and dioxane), aromatic hydrocarbons (for example, toluene and xylene), halogenated hydrocarbons (for example, methylene chloride and chloroform), and carbon tetrachloride. A preferred example of the organic solvent is methylene chloride. The reaction temperature is not particularly limited. However, since this reaction vigorously proceeds while being accompanied with heat generation, it is desired that the reaction is usually carried out under a low temperature condition. The reaction temperature is preferably not higher than 100° C., and most preferably not higher than 35° C. Actually, the reaction may be carried out under irregular reaction temperature adjustment. For example, at the initial stage, the reaction may be carried out while cooling using a dry ice-methanol bath or an ice bath and after raising the temperature in the vicinity of room temperature, and the reaction may be then continued. The reaction time is not particularly limited. Usually, the desired silicon compound can be obtained for 1 to 10 hours.

The compound (1-1) can also be produced in a process in which the reaction step between the compound (6) and the compound (8) is first carried out. First of all, the compound (6) and the compound (8) are reacted with each other to synthesize a compound represented by Formula (2-1-2).

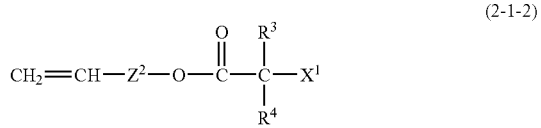

(2-1-2)

In Formula (2-1-2), $Z^2$ has the same meaning as $Z^2$ in Formula (6); and $X^1$, $R^3$, and $R^4$ have the same meanings as those in Formula (8), respectively.

Next, the compound (2-1-2) and the compound (4) are subjected to a hydrosilylation reaction to synthesize a compound represented by Formula (2-1-3), which is then reacted with the compound (3-1) or the compound (3-2) to synthesize the compound (1-1). A method for synthesizing the compound (2-1-3) is described in, for example, *Macromol. Rapid Commun.*, 23 (2002), 612.

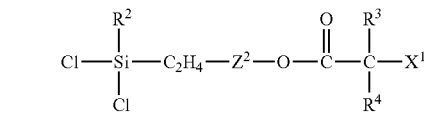

(2-1-3)

In Formula (2-1-3), $Z^2$ has the same meaning as $Z^2$ in Formula (6); $R^2$ has the same meaning as $R^2$ in Formula (1-1); and $X^1$, $R^3$, and $R^4$ have the same meanings as those in Formula (8), respectively.

The reaction between the compound (6) and the compound (8) can be carried out in the same manner as in the reaction between the compound (7) and the compound (8). The hydrosilylation reaction between the compound (2-1-2) and the compound (4) can be carried out in the same manner as in the reaction between the compound (6) and the compound (5). The reaction between the compound (2-1-3) and the compound (3-1) or the compound (3-2) can be carried out in the same manner as in the reaction between the compound (4) and the compound (3-1) or the compound (3-2).

In the following description, the unreacted raw material compound and solvent will be sometimes generically named "impurities". When a distillation method is applied for the purpose of removing the impurities, there is some possibility that the desired compound is decomposed because it is held under a high temperature condition over a long period of time. Accordingly, in order to efficiently remove the impurities without hindering the purity of the compound (1-1), it is preferred to carry out purification by a reprecipitation operation. This purification method is carried out in the following way. First of all, a reaction solution is dissolved in a solvent capable of dissolving both the compound (1-1) and the impurities therein. Roughly speaking, at this time, a preferred concentration of the compound (1-1) is 1 to 15% by weight. Next, a so-called precipitating agent which is a solvent which does not dissolve the compound (1-1) therein but dissolves the impurities therein is added to this solution, thereby precipitating only the compound (1-1). A preferred amount of the precipitating agent to be used is 20 to 50 times on the basis of the weight of the solvent to be used for the purpose of dissolving both the compound (1-1) and the impurities therein. This range of use amount is a rough basis and may not always fall within this range along with the foregoing concentration range of the compound (1-1).

A preferred solvent for dissolving the compound (1-1) therein is a solvent having a large dissolving power and a relatively low boiling point. The precipitating agent is preferably a solvent which is compatible with the solvent for dissolving the compound (1-1) therein, does not at all dissolve the compound (1-1) therein but dissolves only the impurities therein, and has a relatively low boiling point. An example of the preferred precipitating agent is a lower alcohol. Methanol is especially preferred as the precipitating agent. In order to further enhance the degree of purification, the number of repetition of the reprecipitation operation may be increased.

After removing the polymerizable unreacted material, in order to further purify the compound (1-1), it is preferred to employ column chromatography. An adsorbing agent which is used on this occasion is s silica gel. Preferred examples of a developing solvent include hexane, cyclohexane, toluene, chloroform, ethyl acetate, and acetone. A more preferred developing solvent is a mixed solvent of ethyl acetate and hexane. Incidentally, though a mixing ratio of the solvent is not particularly limited, it may be adjusted such that a transfer ratio (Rf value) of the desired material to the developing solvent falls within the range of 0.1 to 0.7.

The production process of the compound (1-2) will be hereunder described.

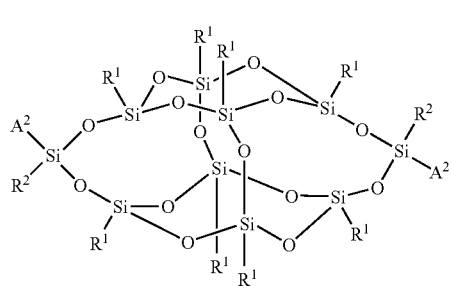

(1-2)

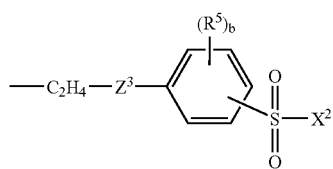

(2-2-1)

In Formula (1-2), $A^2$ is a group represented by Formula (2-2-1). $R^1$, $R^2$ and the respective symbols in Formula (2-2-1) have the meanings as describe above.

First of all, the compound (4) and a compound (2-2-2) are subjected to a hydrosilylation reaction to synthesize a compound represented by Formula (2-2-3).

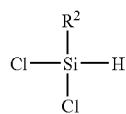

(4)

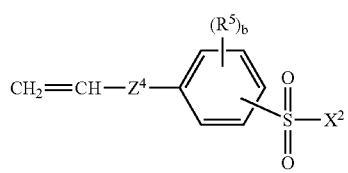

(2-2-2)

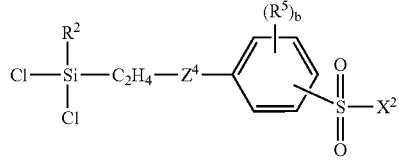

(2-2-3)

In these formulae, $Z^4$ is a single bond or an alkylene having 1 to 8 carbon atoms, and arbitrary —$CH_2$— in this alkylene may be replaced by —O— or —COO—; $R^5$, $X^2$, and $a$ have the same meanings as those in Formula (2-2), respectively; the bonding position of —$SO_2X^2$ on the benzene ring is an ortho-position, a meta-position, or a para-position with respect to the bonding position of $Z^4$; the bonding position of $R^5$ is an arbitrary position excluding the respective bonding positions of $Z^4$ and —$SO_2X^2$; and $R^2$ has the same meaning as $R^2$ in Formula (1-2).

Subsequently, the compound (2-2-3) and the foregoing compound (3-1) or compound (3-2) are reacted with each other to produce the compound (1-2).

The hydrosilylation ion between the compound (4) and the compound (2-2-2) can be carried out in the same manner as in the reaction between the compound (5) and the compound (6) The reaction between the compound (2-2-3) and the compound (3-1) or the compound (3-2) can be carried out in the same manner as in the reaction between the compound (4) and the compound (3-1) or the compound (3-2). For the purification of the compound (1-2) in the reaction mixture, the foregoing purification method by a reprecipitation operation or/and column chromatography can be employed.

The production process of the compound (1-3) will be hereunder described.

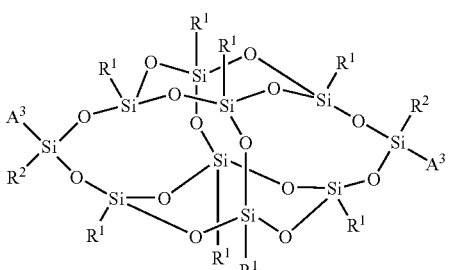

(1-3)

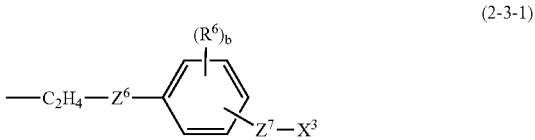

(2-3-1)

In Formula (1-2), $A^3$ is a group represented by Formula (2-3-1). $R^1$, $R^2$ and the respective symbols in Formula (2-3-1) have the meanings as describe above.

A preferred production process of the compound (1-3) is a process for subjecting a compound (2-3-2) and the foregoing compound (5) to a hydrosilylation reaction.

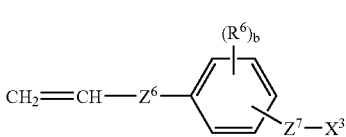

(2-3-2)

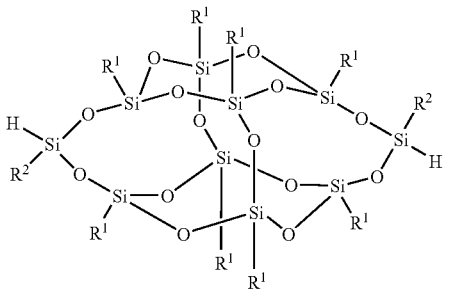

(5)

In Formula (2-3-2), the respective symbols have the same meanings as those in Formula (2-3-1), respectively.

The hydrosilylation reaction between the compound (5) and the compound (2-3-2) can be carried out in the same manner as in the reaction between the compound (5) and the compound (6). For the purification of the compound (1-3) in the reaction mixture, the foregoing purification method by a reprecipitation operation or/and column chromatography can be employed.

The compound (1-4) can be obtained by reacting the compound (1-3) and a dithiocarbamic acid metal salt represented by Formula (9).

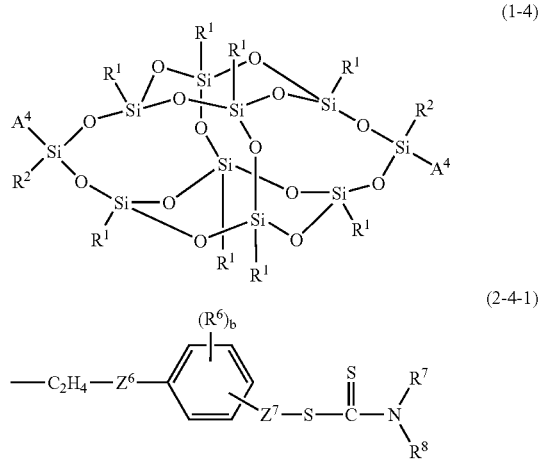
(1-4)

(2-4-1)

In Formula (1-4), $A^4$ is a group represented by Formula (2-4-1). $R^1$, $R^2$ and the respective symbols in Formula (2-4-1) have the meanings as described above.

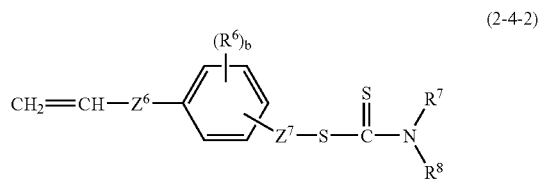
(9)

In Formula (9), $R^7$ and $R^8$ have the same meanings as those in Formula (2-4-1), respectively; $M^1$ is a metal atom belonging to the Group 1 or the Group 2 of the Periodic Table; and p is a value equal to the valence of $M^1$. Examples of $M^1$ include Li, Na, K, Cu, Mg, Ca, and Zn. Preferred examples of $M^1$ include Na and K.

The reaction between the compound (1-3) and the compound (9) is a quantitative nucleophilic substitution reaction, and side reactions do not occur. However, a preferred amount of the dithiocarbamic acid salt to be used is 1 to 5 times in terms of an equivalent ratio to the halogen in the compound (1-3). By using a large amount of this salt, the reaction time can be shortened. The reaction is usually carried out in a dry organic solvent which is inert to the raw materials in an inert gas atmosphere such as a nitrogen gas. Examples of the organic solvent include lower alcohols (for example, methanol), cyclic ethers (for example, tetrahydrofuran and dioxane), and aromatic hydrocarbons (for toluene and xylene). Preferred examples of the organic solvent include tetrahydrofuran and methanol. Taking into consideration a possibility that the dithiocarbamate is thermally decomposed, the reaction temperature is preferably not higher 120° C., and more preferably not higher than 100° C. Though the reaction time is not particularly limited, in general, the desired silicon compound can be obtained for 1 to 10 hours. If desired, a phase transfer catalyst can be used in this reaction. Examples of the phase transfer catalyst include benzyltrimethylammonium chloride, tetramethylammonium chloride, tetrabutylammonium bromide, trioctylammonium chloride, dioctylmethylammonium chloride, triethylamine, and dimethylaniline.

For the purification of the compound (1-4) in the reaction mixture, the foregoing purification method by a reprecipitation operation or/and column chromatography can be employed. The reaction between the dithiocarbamic acid salt and the compound (1-3) and the purification of the compound (1-4) must be carried out in a draft installed with an ultraviolet ray-cut fluorescent lamp and an ultraviolet ray-cut film. Since the compound (1-4) has a dithiocarbamate which is a photosensitizing group, it must be charged in a light-shielded container having an inert gas (for example, nitrogen and argon) enclosed therein in a non-aqueous atmosphere and stored in a cool, dark place.

The compound (1-4) can also be produced in a process in which the reaction step between the dithiocarbamic acid metal salt and the halogenated alkyl group is first carried out. This production process is a process for first reacting the compound (2-3-2) and the compound (9) to form a compound represented by Formula (2-4-2).

(2-4-2)

In Formula (2-4-2), the respective symbols have the same meanings as those in Formula (2-4-1), respectively; and the bonding positions of $Z^7$ and $R^6$ on the benzene ring are the same as the bonding positions of $Z^7$ and $R^6$ in Formula (2-4-1), respectively.

The reaction itself is basically the same as the foregoing reaction between the compound (1-3) and the compound (9) and can be carried out in the same manner as in this reaction. However, the same care as in the case of the reaction between the compound (5) and the compound (2-3-2) in the foregoing production process must be taken in view of the point of handling a polymerizable group-containing compound. That is, the reaction temperature is considerably low and must be adjusted at from about 20 to 80° C., and a polymerization inhibitor must be used. Moreover, ultraviolet rays must be blocked as far as possible not only in the reaction and the purification step but also in the storage of a product. The compound (1-4) can be obtained by a hydrosilylation reaction between this compound (2-4-2) and the foregoing compound (5). The hydrosilylation reaction can be carried out in the same manner as in the reaction between the compound (5) and the compound (6).

The compound (1-3) can also be produced in a production process in which the reaction using the compound (3-1) or the compound (3-2) is a final reaction step. First of all, the compound (4) and the compound (2-3-2) are subjected to a hydrosilylation reaction in the presence of a transition metal catalyst to produce a compound represented by Formula (2-3-3).

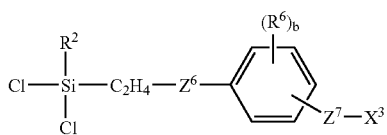

(2-3-3)

In Formula (2-3-3), $R^2$ has the same meaning as $R^2$ in Formula (4); other symbols have the same meanings as those in Formula (2-3-2), respectively; and the bonding positions of $Z^7$ and $R^6$ on the benzene ring are the same as the bonding positions of $Z^7$ and $R^6$ in Formula (2-3-2), respectively.

Then, the compound (2-3-3) and the compound (3-1) or the compound (3-2) are reacted with each other to produce the compound (1-3). The hydrosilylation reaction between the compound (4) and the compound (2-3-2) can be carried out in the same manner as in the hydrosilylation reaction between the compound (5) and the compound (6). The reaction between the compound (2-3-3) and the compound (3-1) or the compound (3-2) can be carried out in the same manner as in the reaction between the compound (4) and the compound (3-1) or the compound (3-2).

Next, the addition polymerizable monomer capable of initiating the polymerization using the compound (1) will be hereunder described. This addition polymerizable monomer is a monomer having at least one addition polymerizable double bond. One of examples of a monomer having one addition polymerizable double bond is a (meth)acrylic acid derivative. Specific examples thereof include (meth)acrylic acid, methyl(meth)acrylate, ethyl(meth)acrylate, n-propyl (meth)acrylate, isopropyl(meth)acrylate, n-butyl(meth)acrylate, isobutyl(meth)acrylate, tert-butyl(meth)acrylate, n-pentyl(meth)acrylate, n-hexyl(meth)acrylate, cyclohexyl(meth) acrylate, n-heptyl(meth)acrylate, n-octyl(meth)acrylate, 2-ethylhexyl(meth)acrylate, nonyl(meth)acrylate, decyl (meth)acrylate, dodecyl(meth)acrylate, phenyl(meth)acrylate, toluyl(meth)acrylate, benzyl(meth)acrylate, 2-methoxyethyl(meth)acrylate, 3-methoxypropyl(meth)acrylate, 3-methoxybutyl(meth)acrylate, 2-hydroxyethyl(meth)acrylate, 2-hydroxypropyl(meth)acrylate, stearyl(meth)acrylate, glycidyl(meth)acrylate, 3-ethyl-3-(meth)acryloyloxymethyloxetane, 2-(meth)acryloyloxyethylisocyanate, 2-aminoethyl(meth)acrylate, 2-(2-bromopropanoyloxy)ethyl(meth) acrylate, 2-(2-bromoisobutyryloxy)ethyl(meth)acrylate, 1-(meth)acryloyloxy-2-phenyl-2-(2,2,6,6-tetramethyl-1-piperidinyloxy)ethane, (1-(4-((4-(meth)acryloyloxy)ethoxyethyl)phenylethoxy)piperidine, γ-(methacryloyloxypropyl) trimethoxysilane, 3-(3,5,7,9,11,13,15-heptaethylpentacyclo [9.5.1.1$^{3,9}$.1$^{5,15}$.1$^{7,13}$]octasiloxan-1-yl)propyl(meth) acrylate, 3-(3,5,7,9,11,13,15-heptaisobutylpentacyclo [9.5.1.1$^{3,9}$.1$^{5,15}$.1$^{7,13}$]octasiloxan-yl)propyl(meth)acrylate, 3-(3,5,7,9,11,13,15-heptaisooctylpentacyclo[9.5.1.1$^{3,9}$. 1$^{5,15}$. 1$^{7,13}$]octasiloxan-1-yl)propyl(meth)acrylate, 3-(3,5,7, 9,11,13,15-heptacyclopentylpentacyclo[9.5.1.1$^{3,9}$.1$^{5,15}$. 1$^{7,13}$]octasiloxan-1-yl)propyl(meth)acrylate, 3-(3,5,7,9,11, 13,15-heptaphenylpentacyclo[9.5.1.1$^{3,9}$.1$^{5,15}$.1$^{7,13}$]octasiloxan-1-yl)propyl(meth)acrylate, 3-[(3,5,7,9,11,13,15-heptaethylpentacyclo[9.5.1.1$^{3,9}$.1$^{5,15}$.1$^{7,13}$]octasiloxan-1-yloxy) dimethylsilyl]propyl(meth)acrylate, 3-[(3,5,7,9,11,13,15-heptaisobutylpentacyclo[9.5.1.1$^{3,9}$.1$^{5,15}$.1$^{7,13}$]octasiloxan-1-yloxy)dimethylsilyl]propyl(meth)acrylate, 3-[(3,5,7,9,11, 13,15-heptaisooctylpentacyclo[9.5.1.1$^{3,9}$.1$^{5,15}$.1$^{7,13}$] octasiloxan-1-yloxy)dimethylsilyl]propyl(meth)acrylate, 3-[(3,5,7,9,11,13,15-heptacyclopentylpentacyclo[9.5.1. 1$^{3,9}$.1$^{5,15}$.1$^{7,13}$]octasiloxan-1-yloxy)dimethylsilyl]propyl (meth)acrylate, 3-[(3,5,7,9,11,13,15-heptaphenylpentacyclo [9.5.1.1$^{3,9}$.1$^{5,15}$.1$^{7,13}$]octasiloxan-1-yloxy)dimethylsilyl] propyl(meth)acrylate, an ethylene oxide adduct of (meth) acrylic acid, trifluoromethylmethyl(meth)acrylate, 2-trifluoromethylethyl(meth)acrylate, 2-perfluoroethylethyl (meth)acrylate, 2-perfluoroethyl-2-perfluorobutylethyl (meth)acrylate, 2-perfluoroethyl(meth)acrylate, trifluoromethyl(meth)acrylate, diperfluoromethylmethyl(meth) acrylate, 2-perfluoromethyl-2-perfluoroethylethyl(meth) acrylate, 2-perfluorohexylethyl(meth)acrylate, 2-perfluorodecylethyl(meth)acrylate, 2-perfluorohexadecylethyl(meth)acrylate, and 2-(meth)acryloyloxyethylphosphorylcholine.

Another example of a monomer having one addition polymerizable double bond is a styrene based monomer.

Specific examples thereof include styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropanoyloxy)styrene, 2-(2-bromoisobutyryloxy)styrene, 1-(2-((4-vinylphenyl)methoxy)-1-phenylethoxy)-2,2,6,6-tetramethylpiperidine, 1-(4-vinylphenyl)-3,5,7,9,11,13,15-heptaethylpentacyclo[9.5.1.1$^{3,9}$.1$^{5,15}$.1$^{7,13}$]octasiloxane, 1-(4-vinylphenyl)-3,5,7,9,11,13,15-heptaisobutylpentacyclo [9.5.1.1$^{3,9}$.1$^{5,15}$.1$^{7,13}$]octasiloxane, 1-(4-vinylphenyl)-3,5,7, 9,11,13,15-heptaisooctylpentacyclo[9.5.1.1$^{3,9}$.1$^{5,15}$.1$^{7,13}$] octasiloxane, 1-(4-vinylphenyl)-3,5,7,9,11,13,15-heptacyclopentylpentacyclo[9.5.1.1$^{3,9}$.1$^{5,15}$.1$^{7,13}$] octasiloxane, 1-(4-vinylphenyl)-3,5,7,9,11,13,15-heptaphenylpentacyclo[9.5.1.1$^{3,9}$.1$^{5,15}$.1$^{7,13}$] octasiloxane, 3-(3,5,7,9,11,13,15-heptaethylpentacyclo[9.5.1.1$^{3,9}$.1$^{5,15}$. 1$^{7,13}$]octasiloxan-1-yl)ethylstyrene, 3-(3,5,7,9,11,13,15-heptaisobutylpentacyclo[9.5.1.1$^{3,9}$.1$^{5,15}$.1$^{7,13}$]octasiloxan-1-yl)ethylstyrene, 3-(3,5,7,9,11,13,15-heptaisooctylpentacyclo]9.5.1.1$^{3,9}$.1$^{5,15}$.1$^{7,13}$]octasiloxan-1-yl)ethylstyrene, 3-(3,5,7,9,11,13,15-heptacyclopentylpentacyclo[9.5.1. 1$^{3,9}$.1$^{5,15}$.1$^{7,13}$]octasiloxan-1-yl)ethylstyrene, 3-(3,5,7,9,11, 13,15-heptaphenylpentacyclo[9.5.1.1$^{3,9}$.1$^{5,15}$.1$^{7,13}$]octasiloxan-1-yl)ethylstyrene, 3-((3,5,7,9,11,13,15-heptaethylpentacyclo[9.5.1.1$^{3,9}$.1$^{5,15}$.1$^{7,13}$]octasiloxan-1-yloxy) dimethylsilyl)ethylstyrene, 3-((3,5,7,9,11,13,15-heptaisobutylpentacyclo [9.5.1.1$^{3,9}$.1$^{5,15}$.1$^{7,13}$]octasiloxan-1-yloxy)dimethylsilyl)ethylstyrene, 3-((3,5,7,9,11,13,15-heptaisooctylpentacyclo[9.5.1.1$^{3,9}$.1$^{5,15}$.1$^{7,13}$]octasiloxan-1-yloxy)dimethylsilyl)ethylstyrene, 3-((3,5,7,9,11,13,15-heptacyclopentylpentacyclo[9.5.1.1$^{3,9}$.1$^{5,15}$.1$^{7,13}$] octasiloxan-1-yloxy)dimethylsilyl)ethylstyrene, and 3-((3,5, 7,9,11,13,15-heptaphenylpentacyclo[9.5.1.1$^{3,9}$.1$^{5,15}$.1$^{7,13}$] octasiloxan-1-yloxy)dimethylsilyl)ethylstyrene.

Other examples of a monomer having one addition polymerizable double bond include fluorine-containing vinyl monomers (for example, perfluoroethylene, perfluoropropylene, and vinylidene fluoride), silicon-containing addition polymerizable monomers (for example, vinyltrimethoxysilane and vinyltriethoxysilane), maleic anhydride, maleic acid, monoalkyl esters and dialkyl esters of maleic acid, fumaric acid, monoalkyl esters and dialkyl esters of fumaric acid, maleimide based monomers (for example, maleimide, methylmaleimide, ethylmaleimide, propylmaleimide, butylmaleimide, hexylmaleimide, octylmaleimide, dodecylmaleimide, stearylmaleimide, phenylmaleimide, and cyclohexylmaleimide), nitrile group-containing monomers (for example, acrylonitrile and methacrylonitrile), amide group-containing monomers (for example, acrylamide and methacrylamide), vinyl ester based monomers (for example, vinyl acetate, vinyl propionate, vinyl pivalate, vinyl benzoate, and vinyl cinnamate), olefins (for example, ethylene and propylene), conjugated diene based monomers (for example, butadiene and isoprene), vinyl halides (for example, vinyl chloride), vinylidene halides (for example, vinylidene chloride), allyl halides (for example, allyl chloride), allyl alcohol, vinylpyrrolidone, vinylpyridine, N-vinylcarbazole, methyl vinyl ketone, and vinyl isocyanate. In addition, there are enumerated macro monomers having one polymerizable double bond in one molecule thereof, the principal chain of which is a macromer of styrene, a (meth) acrylic acid ester, a diorganosiloxane, or an alkylene glycol.

Examples of a monomer having two addition polymerizable double bonds include divinylbenzene and di(meth) acrylate based monomers. Examples of the di(meth)acrylate based monomer include 1,3-butanediol di(meth)acrylate, 1,4-butanediol di(meth)acrylate, 1,6-hexanediol di(meth) acrylate, polyethylene glycol di(meth)acrylate, diethylene glycol di(meth)acrylate, neopentyl glycol di(meth)acrylate, triethylene glycol di(meth)acrylate, tripropylene glycol di(meth)acrylate, hydroxypivalic acid ester neopentyl glycol di(meth)acrylate, trimethylolpropane di(meth)acrylate, bis [(meth)acryloyloxyethoxy]bisphenol A, bis[(meth)acryloyloxyethoxy]tetrabromobisphenol A, bis[(meth)acryloxypolyethoxy]bisphenol A, 1,3-bis(hydroxyethyl)5,5-dimethylhydantoin, 3-methylpentanediol di(meth)acrylate, di(meth)acrylates of hydroxypivalic acid ester neopentyl glycol derivatives, and bis[(meth)acryloyloxypropyl]tetramethyldisiloxane. In addition, there are enumerated macro monomers having two polymerizable double bonds in the molecule thereof, the principal chain of which is a macromer of styrene, a (meth)acrylic acid ester, a diorganosiloxane, or an alkylene glycol.

Examples of a monomer having three or more addition polymerizable double bonds include trimethylolpropane tri (meth)acrylate, pentaerythritol tri(meth)acrylate, pentaerythritol tetra(meth)acrylate, dipentaerythritol monohydroxypenta(meth)acrylate, tris(2-hydroxyethyl isocyanate) tri(meth)acrylate, tris(diethylene glycol)trimellate tri(meth) acrylate, 3,7,14-tris[(((meth)acryloyloxypropyl)dimethylsiloxy)]-1,3,5,7,9,11,14-heptaethyltricyclo[7.3.3.1$^{5,11}$]heptasiloxane, 3,7,14-tris[(((meth)acryloyloxypropyl) dimethylsiloxy)]-1,3,5,7,9,11,14-heptaisobutyltricyclo [7.3.3.1$^{5,11}$]heptasiloxane, 3,7,14-tris[(((meth) acryloyloxypropyl)dimethylsiloxy)]-1,3,5,7,9,11,14-heptaisooctyltricyclo[7.3.3.1$^{5,11}$]heptasiloxane, 3,7,14-tris [(((meth)acryloyloxypropyl)dimethylsiloxy)]-1,3,5,7,9,11, 14-heptacyclopentyltricyclo[7.3.3.1$^{5,11}$]heptasiloxane, 3,7, 14-tris[(((meth)acryloyloxypropyl)dimethylsiloxy)]-1,3,5,7, 9,11,14-heptaphenyltricyclo[7.3.3.1$^{5,11}$]heptasiloxane, octakis(3-(meth)acryloyloxypropyldimethylsiloxy)octasilsesquioxane, and octakis(3-(meth)acryloyloxypropyl)octasilsesquioxane. In addition, there are enumerated macro monomers having three or more polymerizable double bonds in the molecule thereof, the principal chain of which is a macromer of styrene, a (meth)acrylic acid ester, a diorganosiloxane, or an alkylene glycol.

The foregoing monomers may be used singly, or a plurality thereof may be copolymerized. The copolymerization may be random copolymerization or block copolymerization. Of these monomers to be used in the invention, (meth)acrylic acid derivatives and styrene derivatives are preferred; and (meth)acrylic acid derivatives are more preferred. Plural (meth)acrylic acid derivatives may be copolymerized, or plural styrene derivatives may be copolymerized. At least one (meth)acrylic acid derivative and at least one styrene derivative may be copolymerized.

Next, a method for subjecting an addition polymerizable monomer to atom transfer radical polymerization in the presence of a transition metal complex as a catalyst by using, as an initiator, the compound (1-1), the compound (1-2) or the compound (1-3) will be hereunder described. The atom transfer radical polymerization method in the invention is one of living radical polymerization methods. Examples of documents which describe the living radical polymerization method include *J. Am. Chem. Soc.*, 117 (1995), 5614-, *Macromolecules*, 28 (1995), 7901—, and *Science*, 272 (1996), 866-.

Preferred examples of the transition metal complex which is used as the polymerization catalyst include metal complexes containing, as a central metal, an element belongs to the group 7, group 8, group 9, group 10 or group 11 of the periodic table. More preferred examples of the catalyst include zero-valent copper complexes, monovalent copper complexes, divalent ruthenium complexes, divalent iron complexes, and divalent nickel complexes. Above all, copper complexes are preferred. Examples of a monovalent copper compound include cuprous chloride, cuprous bromide, cuprous iodide, cuprous cyanide, cuprous oxide, and cuprous perchlorate. In the case of using a copper compound, for the purpose of enhancing catalytic activity, a polycyclic alkaloid such as 2,2'-bipyridyl or derivatives thereof, 1,10-phenanthroline or derivatives thereof, pyridylmethaneimines (for example, N-(n-propyl)-2-pyridylmethaneimine), polyamines (for example, tetramethylethylenediamine, pentamethyldiethylenetriamine, and hexamethyltris (2-aminoethyl)amine), and L-(−)-sparteine is added as a ligand. A ruthenium(II) chloride tristriphenylphosphine complex (RuCl$_2$(PPh$_3$)$_3$) is also preferred as the catalyst. In the case of using a ruthenium compound as the catalyst, an aluminum alkoxide is added as an activator. Besides, preferred examples of the catalyst include a divalent iron bistriphenylphosphine complex (FeCl$_2$(PPh$_3$)$_2$), a divalent nickel bistriphenylphosphine complex (NiCl$_2$(PPh$_3$)$_2$), and a divalent nickel bistributylphosphonine complex (NiBr$_2$ (PBu$_3$)$_2$).

A solvent may be used in the polymerization reaction. Examples of the solvent which is used include aromatic hydrocarbons (for example, benzene and toluene), ethers (for example, diethyl ether, THF, diphenyl ether, anisole, and dimethoxybenzene), halogenated hydrocarbons (for example, methylene chloride, chloroform, and chlorobenzene), ketones (for example, acetone, methyl ethyl ketone, and methyl isobutyl ketone), alcohols (for example, methanol, ethanol, propanol, isopropanol, n-butyl alcohol, and tert-butyl alcohol), nitrites (for example, acetonitrile, propionitrile, and benzonitrile), esters (for example, ethyl acetate and butyl acetate), carbonate based solvents (for example, ethylene carbonate and propylene carbonate), amide based solvents (for example, N,N-dimethylformamide and N,N-dimethylacetamide), hydrochlorofluorocarbon based solvents (for example, HCFC-141b and HCFC-225), hydrofluorocarbon based solvents (for example, HFCs), perfluorocarbon based solvents (for example, perfluoropentane and perfluorohexane), alicyclic hydrofluorocarbon based solvents (for example, fluorocyclopentane and fluorocyclobutane), oxygen-containing fluorine based solvents (for example, fluoroethers, fluoropolyethers, fluoroketones, and fluoroalchols), and water. The compounds as enumerated in the parentheses are respectively a preferred example of the solvent. These solvents may be used singly or in combination of two or more kinds thereof. The polymerization can also be carried out in an emulsion system or a system using supercritical fluid $CO_2$ as a medium. Incidentally, it should not be construed that the useful solvent is limited thereto.

The atom transfer radical polymerization can be carried out under a reduced pressure, an atmospheric pressure or an elevated pressure depending upon the kind of the addition polymerizable monomer or the kind of the solvent. There is some possibility that the polymerization catalyst or formed radical is deactivated upon contact with oxygen. In such case, the polymerization speed may possibly be lowered, or a satisfactory living polymer may not possibly be obtained. Thus, it is important to carry out the polymerization in an inert gas atmosphere such as nitrogen and argon. In this reaction, dissolved oxygen within the polymerization system must be removed under a reduced pressure in advance. After the removal step of dissolved oxygen, it is possible to transfer the system into the polymerization step as it is under a reduced pressure. For the atom transfer radical polymerization, usual methods can be employed, and there are no particular limitations by the polymerization method. For example, a block polymerization method, a solution polymerization method, a suspension polymerization method, an emulsion polymerization method, a block-suspension polymerization method, and the like can be employed. The polymerization temperature is in the range of 0 to 200° C., and preferably from room temperature to 150° C.

When a compound (1-1-2) is used as the initiator, a polymer as obtained by the foregoing method is represented by Formula (P-1). In the following description, the polymer represented by Formula (P-1) is expressed as "polymer (P-1)".

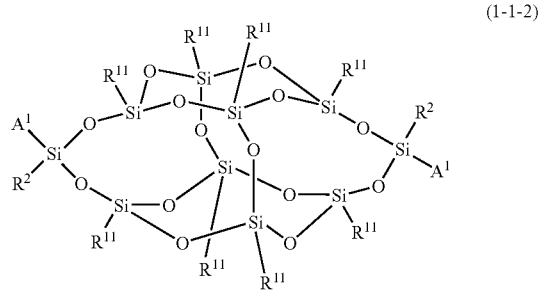
(1-1-2)

In Formula (1-1-2), all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $A^1$ is a group represented by the foregoing formula (2-1-1).

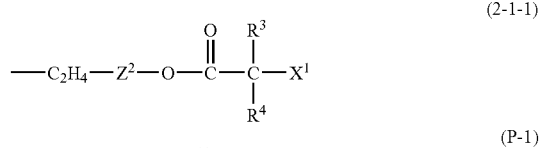
(2-1-1)

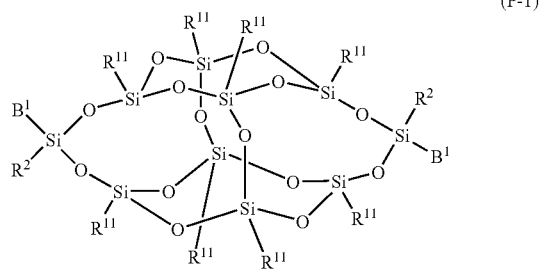
(P-1)

In Formula (P-1), $R^{11}$ and $R^2$ have the same meanings as those in Formula (1-1-2), respectively; and $B^1$ is a group represented by Formula (2-1-P).

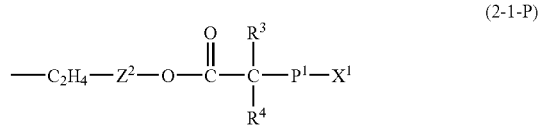
(2-1-P)

In Formula (2-1-P), $Z^2$, $R^3$, $R^4$, and $X^1$ have the same meanings as those in Formula (2-1-1), respectively; and $P^1$ is a chain of a constitutional unit obtained by polymerization of an addition polymerizable monomer.

When a compound (1-2-2) is used as the initiator, a polymer as obtained by the foregoing method is represented by Formula (P-2). In the following description, the polymer represented by Formula (P-2) is expressed as "polymer (P-2)".

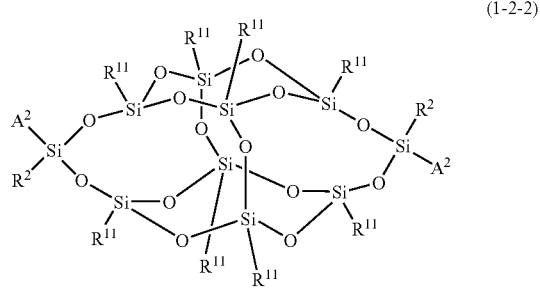
(1-2-2)

In Formula (1-2-2), $R^{11}$ and $R^2$ have the same meanings as those in Formula (1-1-2), respectively; and $A^2$ is a group represented by the foregoing formula (2-2-1).

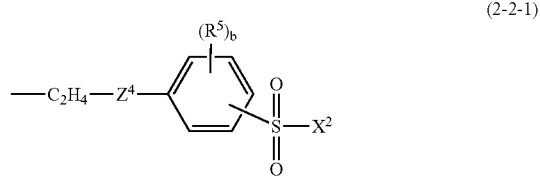
(2-2-1)

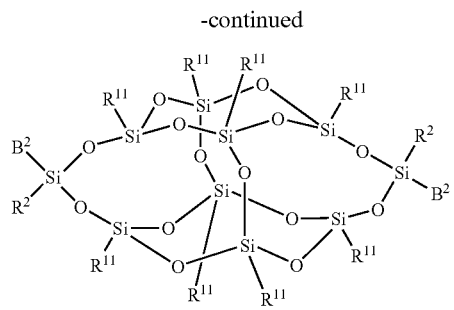 (P-2)

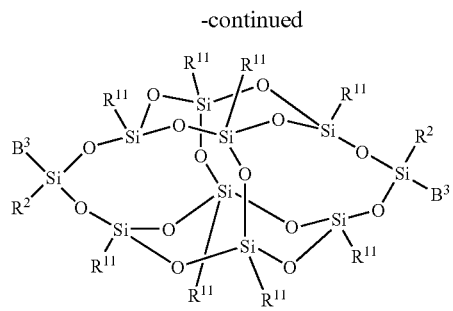 (P-3)

In Formula (P-2), $R^{11}$ and $R^2$ have the same meanings as those in Formula (1-2-2), respectively; and $B^2$ is a group represented by Formula (2-2-P).

In Formula (P-3), $R^{11}$ and $R^2$ have the same meanings as those in Formula (1-3-2), respectively; and $B^3$ is a group represented by Formula (2-3-P).

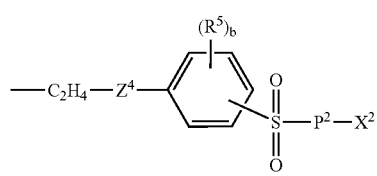 (2-2-P)

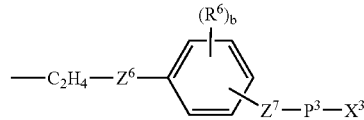 (2-3-P)

In Formula (2-2-P), $Z^4$, $R^5$, b, $R^4$, and $X^2$ have the same meanings as those in Formula (2-2-1), respectively; $P^2$ is a chain of a constitutional unit obtained by polymerization of an addition polymerizable monomer; and the bonding positions of —$SO_2$— and $R^5$ on the benzene ring are the same as the bonding positions of —$SO_2$— and $R^5$ in Formula (2-2-1), respectively.

When a compound (1-3-2) is used as the initiator, a polymer as obtained by the foregoing method is represented by Formula (P-3). In the following description, the polymer represented by Formula (P-3) is expressed as "polymer (P-3)".

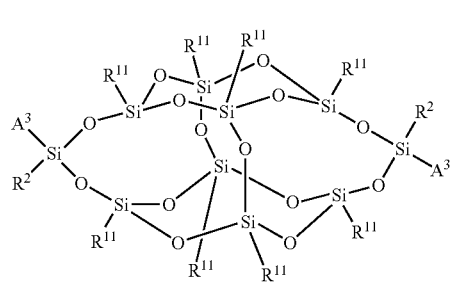 (1-3-2)

In Formula (1-3-2), $R^{11}$ and $R^2$ have the same meanings as those in Formula (1-1-2), respectively; and $A^3$ is a group represented by the foregoing formula (2-3-1).

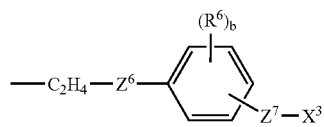 (2-3-1)

In Formula (2-3-P), $Z^6$, $R^6$, b, $Z^7$, and $X^3$ have the same meanings as those in Formula (2-3-1), respectively; $P^3$ is a chain of a constitutional unit obtained by polymerization of an addition polymerizable monomer; and the bonding positions of $Z^7$ and $R^6$ on the benzene ring are the same as the bonding positions of $Z^7$ and $R^6$ in Formula (2-3-1), respectively.

By properly selecting a monomer to be used, it is possible to control the structure of the polymer (P-1). For example, when homopolymerization of a monomer is carried out, a silsesquioxane derivative having a homopolymer bound therein is obtained. When a mixture of plural monomers is polymerized, a silsesquioxane derivative having a random copolymer bound therein is obtained. When a method for successively adding monomers, for example, a method in which after completion of polymerization of a first monomer, a second monomer is added to complete polymerization, is employed, a silsesquioxane derivative having a block copolymer bounded therein can be obtained. By repeating this stepwise polymerization by using plural monomers, a silsesquioxane derivative having a multi-block copolymer bound therein can be obtained. If desired, by making a polyfunctional monomer, a crosslinked polymer having a three-dimensional network structure can also be obtained.

At the time of polymerizing a usual addition polymerizable monomer, by jointly using a compound having a polymerizable functional group and having a function as an initiator at the same time, a silsesquioxane having a highly branched type polymer bound therein can be obtained. Examples of such a compound include 2-(2-bromopropanoyloxy)ethyl(meth)acrylate, 2-(2-bromoisobutyryloxy)ethyl(meth)acrylate, 2-(2-bromopropanoyloxy)styrene, and 2-(2-bromoisobutyryloxy)styrene. By jointly using a silicon compound having a (meth)acryl group or a styryl group, a constitutional unit containing a silicon atom can be introduced in the structure of the polymer. Examples of this silicon compound include trialkoxysilanes, polydimethylsiloxanes and silsesquioxane. A graft copolymer can also be formed by copolymerization with an addition polymerizable monomer having an initiating group which does not participate in the atom transfer radical polymerization and further polymerization of an addition polymerizable monomer using the resulting polymer as an initiator in other polymerization mode (for example, nitroxyl polymerization and photoiniferter polymerization). Examples of the addition polymerizable monomer having an initiating group which does not participate in the atom transfer radical polymerization include 1-(2-(4-vinylphenylmethoxy)-1-phenylethoxy)-2,2,6,6-tetramethylpiperidine, 1-(meth)acryloyloxy-2-phenyl-2-(2,2,6,6-tetramethyl-1-piperidinyloxy) ethane, (1-(4-(4-(meth)acryloyloxyethoxyethyl) phenylethoxy)piperidine, and vinylphenylmethyl dithiocarbamate.

By copolymerization with a glycidyl group-containing monomer (for example, glycidyl (meth)acrylate), an oxetanyl group-containing monomer (for example, 3-ethyl-3-(meth)acryloyloxymethyloxetane), or a dioxolane ring-containing monomer (for example, 4-(meth)acryloyloxymethyl-2-methyl-2-ethyl-1,3-dioxolane) and subsequent addition of an aliphatic sulfonium salt, an aromatic sulfonium salt, or an aromatic iodonium salt as a thermally latent or photolatent cationic polymerization initiator to the resulting polymer, a crosslinked polymer having a three-dimensional structure by cationic polymerization can also be obtained. Examples of the aliphatic sulfonium salt as the thermally latent cationic polymerization initiator include 3-methyl-2-butenyltetramethylenesulfonium hexafluoroantimonate and 2-butenyltetramethylenesulfonium hexafluoroantimonate, all of which are sold by Asahi Denka Co., Ltd. As the aromatic sulfonium salt as the thermally latent or photolatent cationic polymerization initiator, a number of products are sold by Sanshin Chemical Industry Co., Ltd. and Asahi Denka Co., Ltd. Diphenyl-4-thiophenoxyphenylsulfonium hexafluoroantimonate is an example of the aromatic sulfonium salt, too. Examples of the aromatic iodonium salt include (4-pentadecyloxyphenyl)phenyl iodonium hexafluoroantimonate. In carrying out the photolatent cationic polymerization, a photosensitizer such as ADEKA OPTOMER SP-100 (manufactured by Asahi Denka Co., Ltd.) may be used jointly. Furthermore, in obtaining a crosslinked polymer having a three-dimensional network structure by cationic polymerization, a monofunctional or polyfunctional glycidyl based crosslinking agent or a monofunctional or polyfunctional oxetane based crosslinking agent may be made coexistent.

Next, a purification method of the polymer (P-1) will be described. Isolation/purification of this polymer is achieved by efficiently removing the unreacted addition polymerizable monomer. Though a variety of methods are employable, a purification method by a reprecipitation operation is preferred. This purification method is carried out in the following way. First of all, to a polymerization reaction solution containing the polymer (P-1) and the unreacted monomer, a so-called precipitating agent which is a solvent which does not dissolve the polymer (P-1) therein but dissolves the unreacted monomer therein is added, thereby precipitating only the polymer (P-1). A preferred amount of the precipitating agent to be used is 20 to 50 times on the basis of the weight of the foregoing polymerization reaction solution.

The precipitating agent is preferably a solvent which is compatible with the solvent to be used at the time of polymerization, does not at all dissolve the polymer (P-1) therein but dissolves only the unreacted monomer therein, and has a relatively low boiling point. Preferred examples of the precipitating agent include lower alcohols and aliphatic hydrocarbons. Methanol and hexane are especially preferred as the precipitating agent. In order to further enhancing the removal efficiency of the unreacted monomer, the number of repetition of the reprecipitation operation may be increased.

In this way, it is possible to deposit only the polymer (P-1) in a poor solvent, and it is possible to easily separate the unreacted monomer and the polymer from each other by a filtration operation.

Since the transition metal complex as the polymerization catalyst remains in the polymer (P-1) as isolated by the foregoing method, problems such as coloration of the polymer, influences on physical properties, and environmental safety may possibly be caused. Thus, this catalyst residue must be removed at the time of completion of the polymerization reaction. The catalyst residue can be removed by an adsorption treatment using active carbon, etc. Examples of adsorbing agents other than active carbon include ion exchange resins (for example, acidic, basic or chelate type ion exchange resins) and inorganic adsorbing agents. The inorganic adsorbing agent has a solid acidic, solid basic or neutral nature. Since this inorganic adsorbing agent is a particle having a porous structure, it has a very high adsorbing ability. It is one of characteristic features of the inorganic adsorbing agent that it can be used in a wide temperature range of from low temperatures to high temperatures.

Examples of the inorganic adsorbing agent include clay based adsorbing agents such as silicon dioxide, magnetic oxide, silica/alumina, aluminum silicate, active alumina, acid clay, and activated clay; zeolite based adsorbing agents; dawsonite compounds; and hydrotalcite compounds. The zeolite includes a natural product and a synthetic product, all of which are employable. Though the silicon dioxide includes various kinds of products such as a crystalline product, an amorphous product, a non-crystalline product, a glassy product, a synthetic product, and a natural product, powdered silicon dioxide can be used in the invention regardless of the kind. Examples of the natural aluminum silicate include pumice, fly ash, kaolin, bentonite, activated clay, and diatomaceous earth. The synthetic aluminum silicate has a large specific surface area and has a high adsorption ability. The hydrotalcite compound is a hydrated carbonate of an aluminum/magnesium hydroxide.

It is preferred that the acidic adsorbing agent or the basic adsorbing agent is used jointly with active carbon. Examples of the acidic adsorbing agent include acid clay, activated clay, and aluminum silicate. Examples of the basic adsorbing agent include active alumina, the foregoing zeolite based adsorbing agent, and a hydrotalcite compound. These adsorbing agents may be used singly or in admixture of two or more kinds thereof. The polymer (P-3) as produced by the atom transfer radical polymerization can be purified upon contact with active alumina. As the active alumina, commercial products available from Aldrich and the like can be used. In the case of carrying out an adsorption treatment by using active alumina together with other adsorbing agent, while the adsorbing agents can be mixed and brought into contact with each, they may be brought into contact with each other in separate steps. In contacting the adsorbing agent, the reaction solution may be used as it is, or the reaction solution may be diluted with a solvent. The diluting solvent may be selected from general solvents only under a condition that it is not a poor solvent of the polymer. Though the treatment temperature with the adsorbing agent is not particularly limited, it is in general in the range of 0° C. to 200° C., and preferably from room temperature to 180° C. An amount of the adsorbing agent to be used is in the range of 0.1 to 500% by weight on the basis of the weight of the polymer (P-1). A preferred range of the amount of the adsorbing agent to be used is 0.5 to 10% by weight while taking into account the economy and operability.

In the solid-liquid contact between the adsorbing agent and the polymer solution, stirring and mixing and a method of batch system for carrying out solid-solution separation by a batch operation can be utilized. Besides, continuous methods such as a fixed bed system for filling an adsorbing agent in a vessel and passing a polymer solution therethrough; a moving bed system for passing a liquid through a moving bed of an adsorbing agent; and a fluidized bed system for fluidizing an adsorbing agent with a liquid and adsorbing the liquid can be utilized. In addition, if desired, it is possible to combine a mixing and dispersing operation by stirring with an operation for improving dispersion efficiency by means of shaking a vessel, utilizing a supersonic wave, etc. After bringing the polymer solution into contact with the adsorbing agent, the adsorbing agent is removed by a method such as filtration, centrifugation, and sedimentation and separation, and a water washing treatment is carried out, if desired, thereby obtaining a purified polymer solution. Though the treatment with the adsorbing agent may be carried out for the polymer (P-1) as a final product, it may also be carried out for an intermediate for producing this polymer. For example, in the respective polymerization stages of a block copolymer as obtained by the atom transfer radical polymerization, this polymer can be isolated and subjected to an adsorption treatment. The polymer (P-1) having been treated with the adsorbing agent may be separated by depositing it in a poor solvent or distilling off a volatile component such as the solvent in vacuo.

The catalyst residue can be removed by a purification treatment by using a water-insoluble solvent and a complexing agent aqueous solution or by using a water-insoluble solvent and a complexing agent aqueous solution further containing an electrolyte component. That is, after dissolving the polymer (P-1) in a water-insoluble solvent, a complexing agent aqueous solution or a complexing agent aqueous solution further containing an electrolyte component is added to this solution of the polymer (P-1), followed by stirring and mixing, thereby converting the transition metal component into a complex with this complexing agent; and the complex is then extracted into an aqueous layer, whereby the concentration of the catalyst component remaining in the polymer (P-1) can be remarkably reduced.

Also, the polymerization reaction solution may be subjected to a purification treatment. In the case where the viscosity of the polymerization reaction solution is high, the polymerization reaction solution may be subjected to a purification treatment after adding a water-insoluble solvent thereto to adjust the solution at an appropriate viscosity. That is, after completion of the polymerization reaction, the polymerization reaction solution containing the polymer (P-1) is diluted with a prescribed amount of a water-insoluble solvent; a complexing agent aqueous solution or a complexing agent aqueous solution further containing an electrolytic component is added to this solution, followed by stirring and mixing, thereby complexing the transition metal component and transferring it into the foregoing aqueous solution; and the foregoing aqueous solution and the water-insoluble solvent containing the polymer (P-1) are then separated from each other by a physical operation such as centrifugation and standing separation. By such a purification treatment, the concentration of the catalyst component remaining in the polymer (P-1) can be remarkably reduced.

The operational procedures of this purification treatment do not always follow the foregoing procedures. For example, after adding a complexing agent or a complexing agent and an electrolyte component to the polymer (P-1) or the polymerization reaction solution containing the polymer (P-1), a water-insoluble solvent may be added, followed by optionally adding water. Even by carrying out the purification treatment by any operational procedures, the final stage becomes an extraction treatment likewise the case of the operational procedures as first described, thereby obtaining the same effect.

In the following description, a solution having the polymer (P-1) dissolved in a water-insoluble solvent, a polymerization reaction solution containing the polymer (P-1), a solution having this polymerization reaction solution diluted with a water-insoluble solvent is sometimes called the polymer (P-1) solution. Mixing and contact of the polymer (P-1) solution and a complexing agent aqueous solution or a complexing agent aqueous solution further containing an electrolyte component are preferably carried out by stirring in a batch-tank type processing tank equipped with a stirring unit. A shaking-tank type processing tank may also be used. On condition that the polymer (P-1) solution is uniform and has a viscosity such that stirring and mixing with the complexing agent aqueous solution can be achieved, the polymer concentration in the polymer (P-1) solution is preferably not more than 40% by weight. In the case where the polymer concentration in the polymer (P-1) solution is increased, there is some possibility that deposition or thickening of the polymer becomes problematic. On this occasion, the treatment may be carried out under heating by using a processing tank equipped with a heating unit such as a steam coil or a steam jacket capable of achieving heating at from about 70 to 100° C. So far as the polymer concentration in the polymer (P-1) solution is low and the polymer (P-1) solution is uniform at room temperature, stirring and contact can also be carried out at room temperature.

For oil-water separation between the polymer (P-1) solution and the complexing agent aqueous solution or the complexing agent aqueous solution further containing an electrolyte component, centrifugation or standing separation utilizing a difference of specific gravity, or an electrostatic oil purifier utilizing a difference in electric properties can be utilized. In the invention, since oil-water separation between the two phases is necessary, it is the most suitable to use a decanter of a two-phase separation type. As a matter of course, other centrifuges can be used. Furthermore, in the case of jointly using an inorganic adsorbing agent, since a solid such as sludge is contained, a decanter of a three-phase separation type is used. On this occasion, as a matter of course, other centrifuges can be used. The polymer having been treated in the foregoing steps can be isolated by depositing it in a poor solvent or distilling off a volatile component such as the solvent in vacuo.

The number of mixing and contact and oil-water separation steps of the polymer (P-1) solution and the complexing agent aqueous solution or the complexing agent aqueous solution further containing an electrolyte component is not particularly limited so far as the concentration of the catalyst component remaining in the polymer (P-1) can be remarkably reduced. That is, in the case where the mixing and contact and the oil-water separation steps are considered as one step, a stage at which the transition metal component in the polymer (P-1) is analyzed and reduced to the desired content in every step may be taken as the number in this step.

It is preferred that a proportion of addition of the complexing agent to the transition metal component to be contained in the polymer (P-1) is in general 1 to 1,000 equivalents in terms of a molar ratio of the complexing agent to the transition metal component. Since the content of the transition metal in the polymer (P-1) can be estimated in advance by calculation at the time of charging the polymerization reaction solution, the foregoing amount of the complexing agent may be determined depending upon the content of the transition metal as contained in the polymer (P-1) to be treated. A concentration of the complexing agent in the complexing agent aqueous solution is preferably in the range of 0.001 to 20% by weight.

In addition, in the complexing agent aqueous solution further containing an electrolyte component, its amount of use is not particularly limited so far as it is the principal object to improve oil-water separation efficiency by increasing a specific gravity of the aqueous solution and the time required for the separation is shortened. In general, the saturated or half saturated complexing agent aqueous solution further containing an electrolyte component can be used.

Though such a step may be carried out for the polymer (P-1) as a final product, it may also be carried out for an intermediate for producing this polymer. For example, in the respective polymerization stages of a block copolymer as obtained by the atom transfer radical polymerization, this polymer can be isolated and subjected to such a treatment.

Examples of the water-insoluble solvent which is used in this purification step include anisole, benzene, carbon tetrachloride, chlorobenzene, chloroform, 1-chloronaphthalene, dibenzylnaphthalene, o-dichlorobenzene, m-dichlorobenzene, 1,1-dichloroethane, 1,2-dichloroethane, dichloromethane, diisopropyl ether, N,N-dimethylaniline, diphenyl ether, ethyl acetate, mesitylene, methyl acetate, isoamyl acetate, cyclohexanone, cyclopentanone, nitrobenzene, nitromethane, tetrachloroethylene, tetralin, toluene, trichloroethylene, and xylene. Of these, chloroform, ethyl acetate, and toluene are more preferred.

The complexing agent aqueous solution is an aqueous solution of at least one compound selected from aliphatic carboxylic acids, aromatic carboxylic acids, ammonia, amines, amiocarboxylic acids, amino acids, phosphoric acids, phosphonic acids, and inorganic sulfur compounds. If desired, of these compounds, compounds other than inorganic sulfur compounds can be used in a form of a salt such as a salt of an alkali metal (for example, sodium, potassium, and lithium), a salt of an alkaline earth metal (for example, calcium and barium), a salt of a heavy metal (for example, iron(III) and vanadium), a hydrochloric acid salt, an ammonium salt, an amine salt, a partial neutral salt of an equivalent or more or less of a metal or a basic substance to the carboxyl group, and a mixture of these salts.

Examples of the aliphatic carboxylic acid include formic acid, acetic acid, propionic acid, butyric acid, isobutyric acid, valeric acid, isovaleric acid, oxalic acid, malonic acid, succinic acid, glutaric acid, maleic acid, adipic acid, fumaric acid, citraconic acid, itaconic acid, tricarballylic acid, propane-1,1,2,3-tetracarboxylic acid, butane-1-glycolic acid, lactic acid, β-hydroxypropionic acid, malic acid, tartaric acid, citric acid, alloisocitric acid, gluconic acid, pyruvic acid, oxaluric acid, diglycolic acid, and thiodiglycolic acid. Examples of the aromatic carboxylic acid include benzoic acid, phthalic acid, isophthalic acid, mandelic acid, salicylic acid, 5-sulfosalicylic acid, α-carboxy-o-anisic acid, and o-(carboxymethylthio)benzoic acid.

Examples of the amine include diethylamine, methylamine, ethylamine, propylamine, triethylamine, morpholine, piperidine, ethylenediamine, N-methylethylenediamine, N-ethylethylenediamine, N-n-propylethylenediamine, N-isopropylethylenediamine, N-(2-hydroxyethyl)ethylenediamine, N,N-dimethylethylenediamine, N,N-diethylethylenediamine, N,N'-dimethylethylenediamine, N,N'-diethylethylenediamine, N,N'-di-n-propylethylenediamine, N,N-di(2-hydroxyethyl)ethylenediamine, N,N,N',N'-tetramethylethylenediamine, 1,2-diaminopropane, meso-2,3-diaminobutane, rac-2,3-diaminobutane, trimethylenediamine, tetramethylenediamine, pentamethylenediamine, triethylenediamine, diethylenetriamine, 3,3'-diaminodipropylamine, triethylenetetramine, 2-hydroxyethylamine, 2-methoxyethylamine, 2,2'-dihydroxydiethyleneamine, and polyamideamine.

Examples of the aminocarboxylic acid include iminodiacetic acid, iminodipropionic acid, N-methyliminodiacetic acid, N-(3,3'-dimethylbutyl)iminodiacetic acid, phenyliminodiacetic acid, hydroxyethyliminodiacetic acid, hydroxyethyliminodipropionic acid, hydroxypropyliminodiacetic acid, 2-hydroxycyclohexyliminodiacetic acid, methoxyethyliminodiacetic acid, 2-hydroxybenzyliminodiacetic acid, N-(o-carboxyphenyl)iminodiacetic acid, N-(m-carboxyphenyl)iminodiacetic acid, N-(p-carboxyphenyl)iminodiacetic acid, N-(carbamoylmethyl)iminodiacetic acid, cyanomethyliminodiacetic acid, aminoethyliminodiacetic acid, 2-ethoxycarbonylaminoethyliminodiacetic acid, phosphonomethyliminodiacetic acid, phosphonoethyliminodiacetic acid, sulfoethyliminodiacetic acid, o-sulfophenyliminodiacetic acid, m-sulfophenyliminodiacetic acid, nitrilotriacetic acid, carboxyethyliminodiacetic acid, carboxymethyliminodipropionic acid, nitrilotripropionic acid, N,N'-ethylenediamine, ethylenediamine-N,N'-dipropionic acid, N,N'-di(hydroxyethyl)ethylenediaminediacetic acid, N-n-butylethylenediaminetriacetic acid, N-cyclohexylethylenediaminetriacetic acid, N'-hydroxyethyl-N,N,N'-triacetic acid, benzylethylenediaminetriacetic acid, ethylenediaminetetraacetic acid, ethylenediaminetetraacetic acid-zinc, ethylenediaminetetraacetic acid-disodium, ethylenediaminetetraacetic acid-potassium, ethylenediaminetetraacetic acid-magnesium, ethylenediaminetetraacetic acid-dipotassium, ethylenediamine-N,N'-diaetic acid-N,N'-dipropionic acid, ethylenediamine-N,N'-di(2-propionic acid), ethylenediamine-N,N'-disuccinic acid, ethylenediamine-N,N'-diglutaric acid, ethylenediaminetetrapropionic acid, 1,2-propylenediaminetetraacetic acid, trimethylenediaminetetraacetic acid, tetramethylenediaminetetraacetic acid, pentamethylenediaminetetraacetic acid, hexamethylenediaminetetraacetic acid, octamethylenediaminetetraacetic acid, 1,2-cyclopentanediaminetetraacetic acid, trans-cyclohexane-1,2-diaminetetraacetic acid, cyclohexane-1,4-diaminetetraacetic acid, 1,3,5-triaminocyclohexaacetic acid, o-phenylenediaminetetraacetic acid, 2-hydroxytrimethylenediaminetetraacetic acid, ethyl ether diaminetetraacetic acid, hydantoinic acid, (S,S)-ethylenediaminedisuccinic acid, (S,S)-ethylenediaminediglutaric acid, (S)-aspartic acid-N,N-diacetic acid, (S,S)-iminodisuccinic acid, (S)-glutamic acid-N,N-diacetic acid, (S)-α-alanine-N,N-diacetic acid, and taurine-N,N-diacetic acid.

Examples of the amino acid include glycine, sarcosine, glycine methyl ester, valine, alanine, β-alanine, norleucine, leucine, isoleucine, phenylalanine, tyrosine, cysteine, methionine, serine, threonine, asparagine, glutamine, lysine, ε-polylysine, histidine, arginine, glutamic acid, polyglutamic acid, aspartic acid, 1,2-diaminopropionic acid, proline, tryptophan, and N-ethylglycine.

Examples of the phosphoric acid include hexametaphosphoric acid, tetrametaphosphoric acid, and condensed phosphoric acid. Examples of the phosphonic acid include ethylidenediphosphonic acid, diethylenetriaminepenta(methylenephosphonic acid), methyldiphosphonic acid, nitrilotris(methylenephosphonic acid), ethylenediaminetetrakis(methylenephosphonic acid), and 1,2-propylenediaminetetra(methylenephosphonic acid).

Examples of the inorganic sulfur compound include thiosulfuric acid salts (for example, sodium thiosulfate), polythionic acid salts (for example, $SO_3$—$(S)_n$—$SO_3$ (n=1 to 4)), dithionous acid salts (for example, sodium dithionite), sulfurous acid salts (for example, sodium sulfite), and dithionic acid salts (for example, sodium dithionate).

With respect to water to be used, there is no selection condition other than consideration for preventing contamination of the polymer. Though water which has passed through a filter of not more than 50 µm is preferred, pure water having been treated with an ion exchange resin is more preferred.

Examples of the electrolyte component include sodium chloride, ammonium chloride, sodium acetate, a sodium salt of phosphoric acid, sodium citrate, sodium tartarate, sodium benzoate, sodium sorbate, sodium phthalate, and sodium metabisulfite. Corresponding potassium salts may also be used. Materials which can be utilized as the electrolyte component are also included among the compounds to be used in the foregoing complexing agent aqueous solution. When the electrolyte component is used, at least one of such materials is added to the complexing agent aqueous solution.

For the purpose of removing the residual catalyst, an adsorption treatment using active carbon, etc. may be employed together with the foregoing method. In the case of jointly using the solid-liquid contact between the ion exchange resin or the inorganic adsorbing agent and the polymer solution, a batch method for carrying out the stirring and mixing and the solid-liquid separation in a batch operation can be utilized. Besides, continuous methods such as a fixed bed system for filling an adsorbing agent in a vessel and passing a polymer solution therethrough; a moving bed system for passing a liquid through a moving bed of an adsorbing agent; and a fluidized bed system for fluidizing an adsorbing agent with a liquid and adsorbing the liquid can be utilized. In addition, if desired, it is possible to combine a mixing and dispersing operation by stirring with an operation for improving dispersion efficiency by means of shaking a vessel, utilizing a supersonic wave, etc. After bringing the polymer solution into contact with the adsorbing agent, the adsorbing agent is removed by a method such as filtration, centrifugation, and sedimentation and separation, and a water washing treatment is carried out, if desired, whereby the degree of purification can be further increased.

An analytical method of the molecular weight and the molecular weight distribution of the polymer (P-1) will be hereunder described. In general, the molecular weight of an addition polymer can be measured by gel permeation chromatography (GPC) using a calibration curve with, as a standard sample, a linear polymer such as poly(methyl methacrylate). However, the polymer (P-1) belongs to a polymer of an addition polymerizable monomer using a silsesquioxane as a starting point, namely a branched type polymer compound. For that reason, it is considered that in the structure of the polymer (P-1) as it is, in determining its molecular weight, it is problematic in view of the precision of the molecular weight analysis to use a calibration curve with, as a standard sample, a linear polymer such as polystyrene and poly(methyl methacrylate). However, since the terminal portion of the polymer (P-1) is a silsesquioxane, the polymer can be easily decomposed under an acidic condition or a basic condition. That is, by cutting off the addition polymer from the silsesquioxane and then measuring its molecular weight, the precision of the molecular weight analysis of the polymer segment can be further improved. In the case of decomposing the polymer (P-1) under an acidic condition, it is preferred to use hydrofluoric acid. In the case of decomposing the polymer (P-1) under a basic condition, it is preferred to use potassium hydroxide. The decomposition of the polymer (P-1) can be carried out in any of a homogeneous system or a heterogeneous system. For example, the silsesquioxane segment of the polymer (P-1) can be cut off in a homogeneous mixed system of an organic solvent capable of dissolving the polymer (P-1) therein (for example, THF and acetonitrile) and hydrofluoric acid. The decomposition of the silsesquioxane segment can also be carried out in a heterogeneous mixed system of toluene and hydrofluoric acid. On this occasion, it is preferred to jointly use a phase transfer catalyst. Examples of the phase transfer catalyst include benzyltrimethylammonium chloride, tetramethylammonium chloride, tetrabutylammonium bromide, trioctylammonium chloride, dioctylmethylammonium chloride, triethylamine, and dimethylaniline. In the case of using potassium hydroxide, it is also possible to decompose the polymer in a mixed solvent of THF, ethanol and water.

By measuring the addition polymer as cut off by the foregoing method by GPC, the molecular weight of the addition polymer segment in the polymer (P-1), namely the molecular weight of a so-called graft chain, can be determined. By suing a universal calibration curve as obtained from the viscosity and the GPC data, it is also possible to determine the molecular weight of the polymer (P-1) itself. An absolute molecular weight of the polymer (P-1) can be determined by a terminal group quantitative method, a film osmotic pressure method, an ultracentrifugation method, a light scattering method, or the like.

A molecular weight of the graft chain of the polymer (P-1) is preferably in the range of 500 to 1,000,000, and more preferably 1,000 to 100,000 in terms of a number average molecular weight as reduced into poly(methyl methacrylate). However, the upper limit and the lower limit of this range do not have specific meanings. The molecular weight distribution is preferably in the range of 1.01 to 2.0 in terms of a degree of dispersion (Mw/Mn).

The molecular weight of the graft chain can be adjusted by a ratio of the addition polymerizable monomer and the α-haloester group as the initiating group. That is, a theoretical molecular weight of the graft chain of the polymer (P-1) can be predicted from a molar ratio of addition polymerizable monomer/α-haloester group and a rate of consumption of the monomer according to the following calculation expression.

$Mn=\{[Rate of consumption of monomer (mole \%)]/100\} \times MW_M \times$(Molar ratio of addition polymerizable monomer to α-haloester group)$+MW_I$ In this calculation expression, Mn is a theoretical number average molecular weight; $MW_M$ is a molecular weight of the addition polymerizable monomer; and $MW_I$ is a molecular weight of the α-haloester group. In obtaining a polymer having the foregoing number average molecular weight range, the molar ratio of addition polymerizable monomer/α-haloester group can be selected from the range of from approximately 2/1 to 40,000/1, and preferably from approximately 10/1 to 5,000/1. Furthermore, this number average molecular weight can be adjusted by changing the polymerization time.

A theoretical molecular weight of the polymer (P-1) itself can also be predicted from a molar ratio of addition polymerizable monomer/compound (1-1-2) and a rate of consumption of the monomer according to the following calculation expression.

Mn={[Rate of consumption of monomer (mole %)]/100}×MW$_M$×[Molar ratio of addition polymerizable monomer to compound (1-1-2)]+MW$_1$ In this calculation expression, Mn is a theoretical number average molecular weight; MW$_M$ is a molecular weight of the addition polymerizable monomer; and MW$_1$ is a molecular weight of the compound (1-1-2).

As a method for determining the rate of consumption of the monomer (hereinafter sometimes referred to as "conversion"), any methods of GPC, $^1$H—NMR, and gas chromatography can be employed.

The foregoing description regarding the polymer (P-1) is also applicable to the polymer (P-2) and the polymer (P-3).

Next, a method for photopolymerizing an addition polymerizable monomer using the compound (1-4) as an initiator, namely, a so-called photoiniferter polymerization method, will be described. In this photoiniferter polymerization, it is well known that a dithiocarbamate group causes radical dissociation by light and has excellent polymerization initiating ability and sensitization ability. It is also well known that the photopolymerization of this case is radical polymerization and proceeds in a living polymerization way. Such information is disclosed in, for example, *Polymer Bulletin,* 11 (1984), 135- and *Macromolecules,* 19 (1986), 287-. Accordingly, the silicon compound having a dithiocarbamate group according to the invention can continue to keep a polymerization initiating ability so far as light is irradiated and has a photopolymerization initiating ability for any radical polymerizable monomers.

It is also well known that the dithiocarbamate group has respective functions of a polymerization initiator, a chain transfer agent and a polymerization terminator at the same time during the photopolymerization, and its reaction mechanism has already become clear. The compound (1-4) having a dithiocarbamate group according to the invention is dissociated into a radical on the alkylphenyl group bound on the silsesquioxane and a dithiocarbamate radical upon irradiation with light. The radical on the alkylphenyl group participates in the initiation reaction, and the dithiocarbamate radical participates in the termination reaction. When the irradiation with light is stopped or the monomer is completely consumed, the dithiocarbamate radical adds, as a terminator, to the growth terminal, thereby again forming the dithiocarbamate group. Accordingly, the thus formed polymer can also be used as a polymer photoinitiator having a photopolymerization initiating ability. By decomposition upon irradiation with ultraviolet rays having energy necessary for subjecting the dithiocarbamate group to radical dissociation and having a wavelength of 250 to 500 nm, and more preferably 300 to 400 nm, the silicon compound having a dithiocarbamate group according to the invention can initiate polymerization of the addition polymerizable monomer which is coexistent therewith.

With respect to an embodiment for carrying out the polymerization reaction, the polymerization can be properly employed from block polymerization, solution polymerization, suspension polymerization, emulsion polymerization, block-suspension polymerization, and the like. As a solvent to be used in the case of production by solution polymerization, a solvent having a small chain transfer constant and capable of dissolving an addition polymerizable monomer and its polymer therein is preferred. Examples of such a preferred solvent include benzene, toluene, xylene, ethylbenzene, acetone, methyl ethyl ketone, methyl isobutyl ketone, ethyl acetate, methyl cellosolve, ethyl cellosolve, dimethylformamide, isopropyl alcohol, butanol, hexane, and heptane. Rather than otherwise, a solvent having characteristic absorption in an ultraviolet ray region of 250 to 500 nm is preferred. The polymerization temperature is in the range of 0 to 200° C., and preferably from room temperature to 150° C. but is not particularly limited.

The photoiniferter polymerization can be used under a reduced pressure, an atmospheric pressure or an elevated pressure depending upon the kind of the addition polymerizable monomer or the kind of the solvent. In general, it is important to carry out the polymerization in an inert gas atmosphere such as nitrogen and argon, for example, under circulation of an inert gas. Since dissolved oxygen within the polymerization system must be removed under a reduced pressure in advance, after the removal step of dissolved oxygen, it is possible to transfer the system into the polymerization step as it is under a reduced pressure.

When a compound (1-4-2) is used as an initiator, the polymer as obtained by the foregoing method is represented by Formula (P-4). In the following description, the polymer represented by Formula (P-4) is expressed as "compound (P-4)".

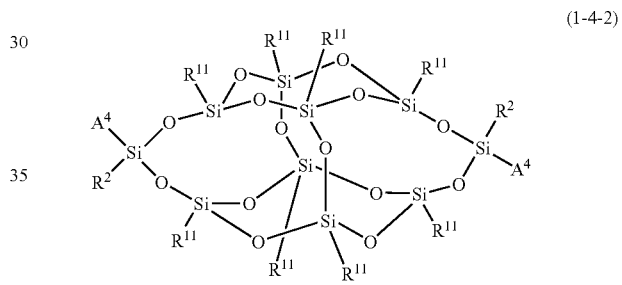

(1-4-2)

In Formula (1-4-2), R$^{11}$ and R$^2$ have the same meanings as those in Formula (1-1-2), respectively; and A$^4$ is a group represented by the foregoing formula (2-4-1).

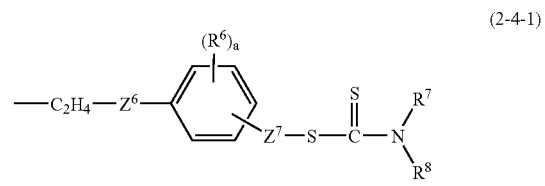

(2-4-1)

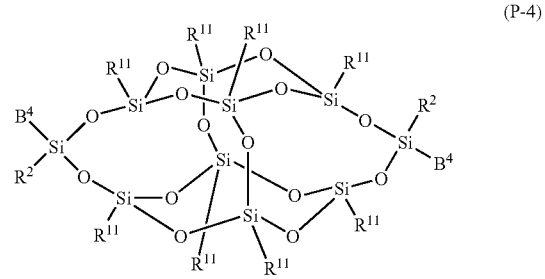

(P-4)

In Formula (P-4), R$^{11}$ and R$^2$ have the same meanings as those in Formula (1-4-2), respectively; and B$^4$ is a group represented by the foregoing formula (2-4-P).

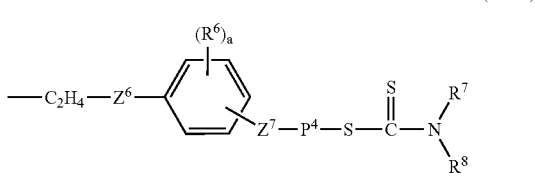

(2-4-P)

In Formula (2-4-P), $P^4$ is a chain of a constitutional unit as obtained by polymerization of an addition polymerizable monomer; other symbols have the same meanings as those in Formula (2-4-1), respectively; and the bonding positions of $R^6$ and $Z^7$ on the benzene ring are the same as the bonding positions of $R^6$ and $Z^7$ in Formula (2-4-1), respectively.

The structure of the polymer (P-4) can be controlled in the same manner as in the case of obtaining the polymer (P-1) by an atom transfer radical polymerization method. By jointly using an initiator monomer (for example, N,N-diethyldithiocarbamoylmethylstyrene and N-ethyldithiocarbamoylmethylstyrene) at the time of usual polymerization of an addition polymerizable monomer, a silsesquioxane derivative having a highly branched type polymer bound therein can be obtained. A graft copolymer can also be formed by copolymerization with an addition polymerizable monomer having an initiating group which does not participate in the photoiniferter polymerization and further polymerization of an addition polymerizable monomer using the resulting polymer as an initiator in other polymerization mode (for example, an atom transfer radical polymerization method). Examples of the addition polymerizable monomer having an initiating group which does not participate in the photoiniferter polymerization include 1-(2-((4-ethenylphenyl)methoxy)-1-phenylethoxy)-2,2,6,6-tetramethylpiperidine, 1-(meth)acryloyloxy-2-phenyl-(2,2,6,6-tetramethyl-1-piperidinyloxy)ethane, (1-(4-((4-(meth)acryloyloxy)ethoxyethyl)phenylethoxy)piperidine, 2-(2-bromopropanoyloxy)ethyl(meth)acrylate, 2-(2-bromoisobutyryloxy)ethyl(meth)acrylate, p-chloromethylstyrene, 2-(2-bromopropanoyloxy)styrene, and 2-(2-bromoisobutyryloxy)styrene.

Incidentally, after completion of the photoiniferter polymerization, by treating the terminal dithiocarbamate group, the polymer (P-4) can be inactivated for ultraviolet rays. Examples of a method of inactivation include a method for treating the polymer (P-4) with an acidic solution or a basic solution, a method of treating the polymer (P-4) at a high temperature of 250° C. or higher for several minutes, a method of irradiating the polymer (P-4) with electron beams with high energy having a wavelength of not more than 220 nm, a method of adding a monomer having an ultraviolet absorbing group and then photopolymerizing it, and a method of simply adding an ultraviolet absorber. It is also possible to substitute the terminal dithiocarbamate group by adding a reagent having a large chain transfer constant (for example, thiol derivatives, thiurams, xanthates, and nitroxides) while irradiating the resulting polymer (P-4) with ultraviolet rays.

An isolation and purification method of the polymer (P-4) will be hereunder described. The isolation and purification of this compound is carried out by efficiently removing the unreacted addition polymerizable monomer. Though there are a variety of methods, the foregoing purification method by a reprecipitation operation is preferred. According to this method, it is possible to deposit only the polymer (P-4) in a poor solvent and to easily separate the unreacted monomer and the polymer by a filtration operation. By distilling off non-volatile components such as the solvent and the unreacted monomer under a reduced pressure condition, the polymer may be isolated. A preferred solvent for dissolving the polymer (P-4) therein is a solvent having a large dissolution power and having a relatively low boiling point. A preferred precipitating agent is a solvent which is compatible with the solvent of the polymer (P-4), does not at all dissolve the compound (P-4) therein but dissolves only the impurities or unreacted monomer therein, and has a relatively low boiling point. Examples of the preferred precipitating agent include lower alcohols and aliphatic hydrocarbons. Methanol and hexane are especially preferred as the precipitating agent. In order to further enhance the degree of purification, the number of repetition of the reprecipitation operation may be increased.

The molecular weight and molecular weight distribution of the polymer (P-4) can be analyzed in the same manner as in the method as described previously regarding the polymer (P-1). The polymer of an addition polymerizable monomer having a silsesquioxane bound therein has a number average molecular weight of a so-called graft chain in the range of 500 to 1,000,000. The number average molecular weight is more preferably in the range of 1,000 to 100,000. However, the upper limit and the lower limit of this range do not have specific meanings. The molecular weight distribution of the graft chain is preferably in the range of 1.01 to 3.0 in terms of a degree of dispersion. Furthermore, by using a universal calibration curve as obtained from the viscosity and the GPC data, it is also possible to determine the molecular weight of the polymer (P-4). An absolute molecular weight of the polymer (P-4) can be determined by a terminal group quantitative method, a film osmotic pressure method, an ultracentrifugation method, a light scattering method, or the like. The molecular weight of the graft chain in the polymer (P-4) can be adjusted in the same manner as in the case of the polymer (P-1).

The polymer of the invention may be used by itself. For example, the polymer can be shaped to porous membrane by applying the solution comprising the polymer on a substrate and drying the coating film.

When the polymer of the invention is mixed with an existing polymer, an effect as a resin modifier can be expected. Among existing polymers, examples of a thermoplastic resin include polyethylene, polypropylene, polyvinylidene chloride, polyvinyl ether, polyvinyl ketone, polyethers, polymethyl methacrylate, polyacrylates, polystyrenes, acrylonitrile-styrene based resins, acrylonitrile-butadiene-styrene based resins, polyvinyl alcohol, polyamides, polyacetals, polycarbonates, polyphenylene ether, polyphenylene oxide, polyethylene terephthalate, polybutylene terephthalate, polysulfones, polyether sulfone, polyphenylene sulfide, polyarylates, polyamide-imides, polyether imide, polyetherehterketones, polyimides, liquid crystal polymers, and polytetrafluoroethylene. Examples of a thermosetting resin include phenol resins, urea resins, melamine resins, alkyd resins, unsaturated polyester resins, epoxy resins, diallyl phthalate resins, polyurethane resins, and silicone resins.

EXAMPLES

The invention will be more specifically described below with reference to the following Examples, but it should not be construed that the invention is limited thereto. Symbols as used in the Examples have the following meanings.

Ph: Phenyl

TMS: Trimethylsilyl

Mn: Number average molecular weight

Mw: Weight average molecule weight

EDTA·2Na: Disodium ethylenediaminetetraacetate dihydrate

Data of molecular weight in the Examples are a value as reduced into polystyrene as determined by GPC (gel permeation chromatography). A measurement condition of GPC is as follows.

Device: JASCO GULLIVER 1500, manufactured by JASCO Corporation (intelligent differential refractometer RI-1530)

Solvent: Tetrahydrofuran (THF)

Flow rate: 1 mL/min

Column temperature: 40° C.

Used column: Column as described below, which is manufactured by Tosoh Corporation (columns were connected to each other in series and provided for use)

TSKguardcolumn HXL-L (GUARDCOLUMN)

TSHgel G1000HxL (exclusion limit molecular weight (polystyrene): 1,000)

TSHgel G2000HxL (exclusion limit molecular weight (polystyrene): 10,000)

Standard sample for calibration curve: Polymer Standards (PL), Polystyrene, manufactured by Polymer Laboratories Ltd.

Incidentally, in Examples 6 to 19, SHODEX KF-G (GUARDCOLUMN) as manufactured by Showa Denko K.K. and two of SHODEX KF-804L (exclusion limit molecular weight (polystyrene): 400,000) as manufactured by Showa Denko K.K. were connected to each other in series and provided for use; and SHODEX STANDARD M-75 (polymethyl methacrylate) as manufactured by Showa Denko K.K. was used as a standard sample for calibration curve. Other conditions are the same as described above.

Example 1

Synthesis of Compound (3-1-1): Compound Represented by Formula (3-1) wherein $R^1$ is phenyl, and M is Na A reaction vessel having an internal volume of 50 liters and equipped with a reflux condenser, a thermometer and a stirring unit was charged with phenyltrimethoxysilane (6.54 kg), 2-propanol (26.3 liters), pure water (0.66 kg), and sodium hydroxide (0.88 kg) and then sealed with dry nitrogen. The mixture was heated while stirring and reacted in a reflux state for 5 hours. After completion of the reaction, a heater was removed from the reaction vessel, and the vessel was allowed to stand at room temperature for 15 hours, thereby cooling the reaction mixture. A supernatant was removed from the thus obtained reaction mixture by decantation. A white solid remaining in the reaction vessel was washed once with 2-propanol (9.87 kg). This was transferred into a polytetrafluoroethylene sheet-lined vat made of stainless steel and dried at an inside temperature of 80° C. under a pressure of $6.7 \times 10^{-4}$ MPa for 24 hours by using a vacuum dryer, thereby obtaining 2.22 kg of Compound (A-1) as a white powder.

Example 2

Introduction of trimethylsilyl group into Compound (A-1)

A 50-mL four-necked flask equipped with a reflux condenser was charged with Compound (A-1) (1.2 g), tetrahydrofuran (10 g), and triethylamine (1.6 g) and then sealed with dry nitrogen. Trimethylchlorosilane (2.2 g) was added dropwise over about one minute under stirring by a magnetic stirrer while keeping the solution temperature at 15° C. to 20° C. After completion of the dropwise addition, stirring was continued at 15° C. for 3.5 hours. After completion of the reaction, the reaction mixture was washed with pure water and dried in vacuo to obtain a white solid (1.2 g). This is designated as Compound (A-T).

Compound (A-T) was subjected to structural analysis by gel permeation chromatography (GPC), $^1$H-NMR, and $^{29}$Si-NMR. It was confirmed from a GPC chart that the white solid was monodispersed and had a number average molecular weight of 970 and a weight average molecular weight of 990 as reduced into polystyrene. It was confirmed from a $^1$H-NMR chart that a phenyl group and a trimethylsilyl group were present in an integral ratio of 2/1. It was confirmed from a $^{29}$Si-NMR chart that this compound had a phenyl group and had two peaks derived from a T-structure at −76.12 ppm and −78.95 ppm in an integral ratio of 1/1 and one peak derived from the trimethylsilyl group at 10.62 ppm (all of which were on the basis of tetramethylsilane). These results support that Compound (A-T) has a structure represented by Formula (3-T). Accordingly, Compound (A-1) is a compound having a structure represented by Formula (3-1-1). Incidentally, the T-structure is a terminology expressing a partial structure in which three oxygen atoms are bound to one silicon atom, namely —Si(O—)$_3$.

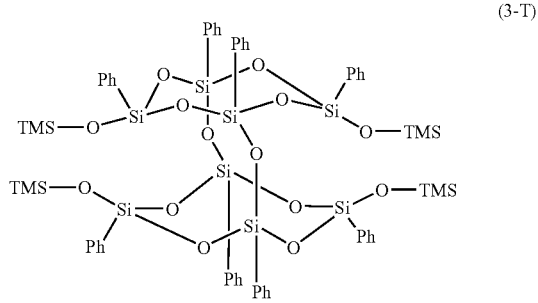

(3-T)

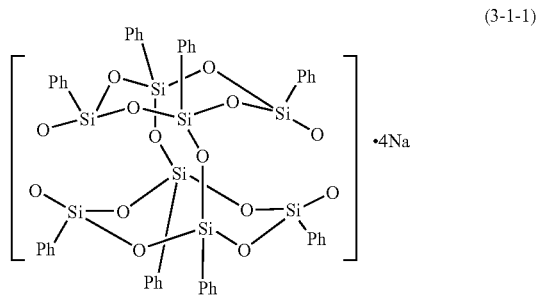

(3-1-1)

Example 3

Synthesis of Compound (5-1): Organosilicon Compound Represented by Formula (5) wherein $R^1$ is phenyl, and $R^2$ is methyl A three-necked flask having an internal volume of 300 mL and equipped with a dropping funnel, a thermometer, and a reflux condenser was charged with a stirrer, Compound (3-1-1) (11.6 g) as obtained by utilizing the method of Example 1, and tetrahydrofuran (100 g) and then sealed with dry nitrogen. Methyldichlorosilane (3.4 g) was added dropwise while stirring by the magnetic stirrer. After completion of the dropwise addition, stirring was continued at room temperature for one hour. After completion of the reaction, 50 g of pure water was charged to dissolve formed sodium chloride therein and also hydrolyze unreacted methyldichlorosilane. The thus obtained reaction mixture was transferred into the dropping funnel and separated into an organic layer and an aqueous layer. After washing the resulting organic layer with saturated salt water, water washing was repeated until the organic layer became neutral. The resulting organic layer was dried over anhydrous magnesium sulfate and concentrated in vacuo by a rotary evaporator. The resulting residue was washed with methanol and dried to obtain 6.9 g of a white powdered solid. The following analytical data suggested that this compound had a structure represented by Formula (5-1).

$^1$H—NMR (400 MHz, CDCl$_3$, TMS standards: δ=0.0 ppm): 0.37 (s, 6H), 4.99 (s, 2H), 7.15 to 7.56 (m, 40H) $^{29}$Si—NMR (79 MHz, CDCl$_3$, TMS standards: δ=0.0 ppm): −32.78 (s, 2Si), −77.91 (s, 4Si), −79.39 (t, 4Si).

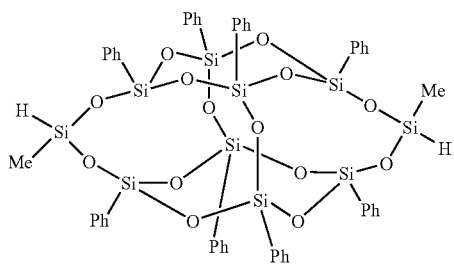

(5-1)

Example 4

Synthesis of Silicon Compound Having hydroxyethoxypropyl Group

A 300-mL three-necked flask equipped with a reflux condenser, a dropping funnel, a thermometer, and a stirrer was charged with Compound (5-1) (15 g) as obtained by utilizing the method of Example 3, tetrahydrofuran (150 g), and a platinum-divinyltetramethyldisiloxane complex/xylene solution (platinum content: 3.0% by weight, 50 μL) and then sealed with dry nitrogen. In addition, the mixture was heated to a reflux state and stirrer by the magnetic stirrer. Thereafter, a mixed solution of ethylene glycol monoallyl ether (4 g) and toluene (4 g) was added dropwise, and reaction was continued for one hour. The reaction solution was sampled and subjected to an IR analysis. As a result, it was confirmed that the absorption at 2,138 cm$^{-1}$ suggesting an Si—H group disappeared. Subsequently, powered active carbon (0.8 g) was added to the reaction solution, and the mixture was stirred for 1.5 hours. After removing the active carbon, the residue was concentrated in vacuo to obtain 15.4 g of a white powered solid. The following analytical data suggested that this compound had a structure represented by Formula (7-1).

$^1$H-NMR (400 MHz, CDCl$_3$, TMS standards: δ=0.0 ppm): 0.31 (d, 6H), 0.73 (s, 4H), 1.69 (s, 4H), 1.92 (s, 2H), 3.29 (s, 8H), 3.52 (s, 4H), 7.21 to 7.53 (m, 40H). $^{13}$C-NMR (100 MHz, CDCl$_3$, TMS standards: δ=0.0 ppm): 0.90, 13.68, 23.73, 62.68, 72.40, 74.40, 128.72 to 135.07 $^{29}$Si-NMR (79 MHz, CDCl$_3$, TMS standards: δ=0.0 ppm): −17.43, −78.69, −79.54, −79.63, −79.71.

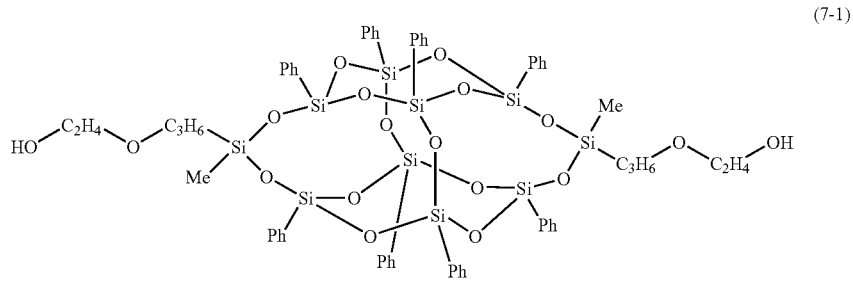

(7-1)

Example 5

Synthesis of Silicon Compound Having 2-bromo-2-methylpropanoyloxyethoxypropyl Group An eggplant type flask having an internal volume of 300 mL was charged with Compound (7-1) (10 g) as obtained in Example 4, triethylamine (2.98 g) having been dried by molecular sieves (4A), and dry methylene chloride (90 mL) in an argon atmosphere. After dissolving the Compound (7-1) at room temperature with stirring by using a magnetic stirrer, the solution was cooled by using a dry ice-methanol bath, and the liquid temperature was kept at −78° C. Subsequently, 2-bromo-2-methylpropanoyl bromide (6.78 g) was rapidly added to this solution, and the mixture was stirred at −78° C. for one hour and further stirred at room temperature for 2 hours. After completion of the reaction, the triethylamine hydrobromide was removed by filtration. Methylene chloride (50 mL) was added to the resulting reaction solution, and the mixture was successively washed twice with a sodium hydrogencarbonate aqueous solution (1%, 100 mL) and twice with water (100 mL), followed by drying over anhydrous magnesium sulfate (5 g). Thereafter, this solution was concentrated at room temperature by using a rotary evaporator to an extent that the liquid amount was about 15 mL. Methanol (100 mL) was added to this concentrated solution (15 mL), thereby causing phase separation of a white solid component. Thereafter, the mixture was statically placed in a freezer at −35° C., thereby thoroughly achieving the phase separation of the white solid component, which was then collected by decantation. This white solid component was dried in vacuo at 40° C. for 3 hours to obtain a white powdered solid (11.8 g).

This white powdered solid had a GPC purity of 99.7%. From the following results of $^1$H-NMR, $^{13}$C-NMR and $^{29}$Si-NMR, it was noted that this compound had a structure represented by Formula (1-1-3).

$^1$H-NMR (400 MHz, CDCl$_3$, TMS standards: δ=0.0 ppm): 0.31 (s, 6H), 0.74 (s, 4H), 1.667 (t, 4H), 1.85 (s, 12H), 3.33 (t, 4H), 3.43 (t, 4H), 4.02 (t, 4H), 7.19 to 7.53 (m, 40H). $^{13}$C-NMR (100 MHz, CDCl$_3$, TMS standards: δ=0.0 ppm): 0.99, 13.74, 23.80, 31.72, 56.73, 66.15, 68.92, 74.45, 128.81 to 135.20. $^{29}$Si-NMR (79 MHz, CDCl$_3$, TMS standards: δ=0.0 ppm): −17.36, −78.69, −79.54, −79.63, −79.71.

which was then further added an anisole solution of Compound (1-1-3) as obtained in Example 5, methyl methacrylate and L-(−)-sparteine, followed by rapidly cooling by using liquefied nitrogen. Thereafter, freeze vacuum deaeration (pressure: 1.0 Pa) was carried out thrice by using a vacuum device installed with an oil rotary pump, and the ampoule was rapidly sealed by using a hand burner while keeping the vacuum state. At this time, a proportion of Compound (1-1-3) to methyl methacrylate to cuprous bromide to L-(−)-sparteine in the solution for polymerization was set up at 1/600/2/4 by mole, and the amount of anisole to be used was set up at an amount such that the concentration of methyl methacrylate was 50% by weight.

Polymerization

The foregoing heat-resistant glass-made ampoule was set in a constant temperature shaking bath to allow the mixture to polymerize, thereby obtaining a brown, viscous solution of Polymer (a). At this time, the polymerization temperature was 70° C., and the polymerization time was 0.5 hours. A monomer conversion in this polymerization reaction system was analyzed on the basis of peak areas as obtained by GPS measurement of poly(methyl methacrylate) having a known concentration. The resulting Polymer (a) was recovered by reprecipitation purification by hexane to prepare an ethyl acetate solution of this Polymer (a) (5% by weight), which was then subjected to flashing together with an EDTA·2Na aqueous solution (2% by weight, 100 mL) by a 300-mL separating funnel, thereby adsorbing and removing a copper complex. In addition, this solution was added dropwise to hexane, thereby reprecipitating the polymer, followed by drying in vacuo (at 80° C. for 6 hours). A monomer conversion in this polymerization reaction system, a theoretical number average molecular weight of Polymer (a) derived from the monomer conversion, a number average molecular weight as actually measured by GPC measurement, and results of analysis of molecular weight distribution are shown in the following Table 6-1.

Analysis of Theoretical Molecular Weight of Graft Chain

Incidentally, the theoretical molecular weight of the graft chain was calculated according to the following expression on the assumption that the ester bonds as an initiation terminal of the polymerization are cut by hydrolysis by a treatment with hydrogen fluoride and that all the termination

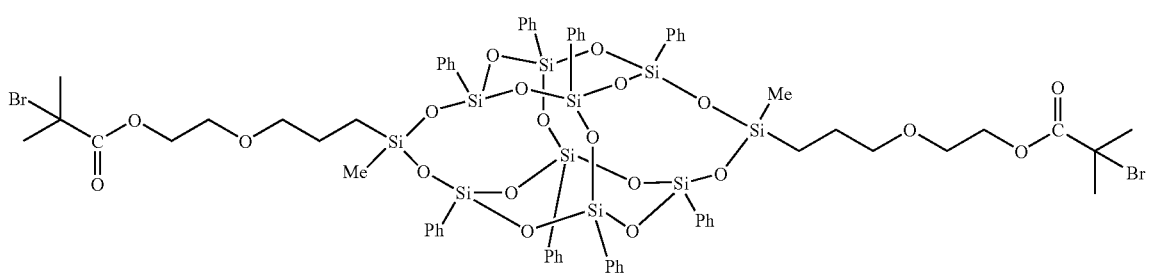

(1-1-3)

Example 6

Preparation of Solution for Polymerization

In an ultraviolet ray-cut draft, cuprous bromide was introduced into a heat-resistant glass-made ampoule, to terminals of the polymerization become Br. The results obtained are shown in the following Table 6-2.

Calculation Expression (Theoretical Mn of graft chain)={[Rate of consumption of monomer (mole %)]/100}×MW$_M$×(Molar ratio of addition polymerizable monomer to α-bromoester group)+MW$_I$ Parameters as Used in Calculation
  $MW_M$=100 (methyl methacrylate)
  Molar ratio of addition polymerizable monomer to α-bromoester group=300
  $MW_I$=167.01 (BrC(CH$_3$)$_2$CO$_2$H)

Measurement of Molecular Weight of Graft Chain

A mixed solution of hydrofluoric acid (0.17 mL) and acetonitrile (0.83 mL) was prepared. Polymer (a) (10 mg) was dissolved in this mixed solution in a polypropylene-made micro tube (1.5 mL) having a stirrer introduced thereinto, and the solution was stirred at 40° C. for 24 hours in an incubator equipped with a magnetic stirrer. Thereafter, the reaction mixture was dried at 80° C. for 3 hours by using a vacuum dryer, thereby recovering a polymer. This polymer was subjected to GPC measurement. The results obtained are shown in the following Table 6-2.

Examples 7 to 11

Polymerization was carried out in the same manner as in Example 6, except for changing the polymerization time as shown in Table 6-1, thereby obtaining a brown, viscous solution of each of Polymer (b) to Polymer (f). Each of these polymers was purified and determined for monomer conversion, theoretical number average molecular weight, number average molecular weight and molecular weight distribution in the same manner as in Example 6. The results obtained are shown in Table 6-1. Calculation of a theoretical number average molecular weight of the graft chain, treatment of the polymer with hydrofluoric acid, measurement of a number average molecular weight of the graft chain by GPC measurement, and analysis of molecular weight distribution were carried out in the same manners as in Example 6. The results obtained are shown in Table 6-2.

TABLE 6-1

| Example | Polymer | Polymerization time (hr) | Conversion (% by mole) | Mn Calculated value | Mn Found value | Mw/Mn Found value |
|---|---|---|---|---|---|---|
| 6 | a | 0.53 | 22.9 | 15,400 | 14,300 | 1.17 |
| 7 | b | 1.0 | 35.3 | 22,800 | 20,300 | 1.15 |
| 8 | c | 2.0 | 49.7 | 31,500 | 30,500 | 1.15 |
| 9 | d | 3.0 | 60.7 | 38,100 | 39,400 | 1.14 |
| 10 | e | 4.0 | 67.3 | 42,000 | 43,200 | 1.17 |
| 11 | f | 5.15 | 69.7 | 43,500 | 48,200 | 1.16 |

TABLE 6-2

| Example | Polymer | Mn Calculated value | Mn Found value | Mw/Mn (Found value) |
|---|---|---|---|---|
| 6 | a | 7,000 | 8,800 | 1.13 |
| 7 | b | 10,800 | 11,600 | 1.14 |
| 8 | c | 15,100 | 16,900 | 1.13 |
| 9 | d | 18,400 | 21,400 | 1.10 |
| 10 | e | 20,400 | 24,500 | 1.10 |
| 11 | f | 21,100 | 27,700 | 1.10 |

Example 12

Preparation of Solution for Polymerization

In an ultraviolet ray-cut draft, cuprous bromide was introduced into a heat-resistant glass-made ampoule, to which was then further added an anisole solution of Compound (1-1-3), methyl methacrylate and L-(−)-sparteine, followed by rapidly cooling by using liquefied nitrogen. Thereafter, freeze vacuum deaeration (pressure: 1.0 Pa) was carried out thrice by using a vacuum device installed with an oil rotary pump, and the ampoule was rapidly sealed by using a hand burner while keeping the vacuum state. At this time, a proportion of Compound (1-1-3) to methyl methacrylate to cuprous bromide to L-(−)-sparteine in the solution for polymerization was set up at 1/300/2/4 by mole, and the amount of anisole to be used was set up at an amount such that the concentration of methyl methacrylate was 50% by weight.

Polymerization

The foregoing heat-resistant glass-made ampoule was set in a constant temperature shaking bath to allow the mixture to polymerize, thereby obtaining a brown, viscous solution of Polymer (2a). At this time, the polymerization temperature was 70° C., and the polymerization time was 0.25 hours. A monomer conversion in this polymerization reaction system was analyzed on the basis of peak areas as obtained by GPS measurement of poly(methyl methacrylate) having a known concentration. The resulting Polymer (2a) was recovered by reprecipitation purification by hexane to prepare an ethyl acetate solution of this Polymer (2a) (5% by weight), which was then subjected to flashing together with an EDTA·2Na aqueous solution (2% by weight, 100 mL) by a 300-mL separating funnel, thereby adsorbing and removing a copper complex. In addition, this solution was added dropwise to hexane, thereby reprecipitating the polymer (2a), followed by drying in vacuo (at 80° C. for 6 hours). A monomer conversion in this polymerization reaction system, a theoretical number average molecular weight of Polymer (2a) derived from the monomer conversion, a number average molecular weight as actually measured by GPC measurement, and results of analysis of molecular weight distribution are shown in the following Table 7-1.

Analysis of Theoretical Molecular Weight of Graft Chain

Incidentally, the theoretical molecular weight of the graft chain was calculated according to the following expression on the assumption that the ester bonds as an initiation terminal of the polymerization are cut by hydrolysis by a treatment with hydrogen fluoride and that all the termination terminals of the polymerization become Br. The results obtained are shown in the following Table 7-2.

Calculation Expression
  (Theoretical Mn of graft chain)={[Rate of consumption of monomer (mole %)]/100}×$MW_M$×(Molar ratio of addition polymerizable monomer to α-bromoester group)+$MW_I$ Parameters as Used in Calculation
  $MW_M$=100 (methyl methacrylate)
  Molar ratio of addition polymerizable monomer to α-bromoester group=150
  $MW_I$=167.01 (BrC(CH$_3$)$_2$CO$_2$H)

Measurement of Molecular Weight of Graft Chain

A mixed solution of hydrofluoric acid (0.17 mL) and acetonitrile (0.83 mL) was prepared. Polymer (2a) (10 mg) was dissolved in this mixed solution in a polypropylene-made micro tube (1.5 mL) having a stirrer introduced thereinto, and the solution was stirred at 40° C. for 24 hours in an incubator equipped with a magnetic stirrer. Thereafter, the reaction mixture was dried at 80° C. for 3 hours by using a vacuum dryer, thereby recovering a polymer. This polymer was subjected to GPC measurement. The results obtained are shown in the following Table 7-2.

Examples 13 to 18

Polymerization was carried out in the same manner as in Example 12, except for changing the polymerization time as shown in Table 7-1, thereby obtaining a brown, viscous solution of each of Polymer (2b) to Polymer (2g). Each of these polymers was purified and determined for monomer conversion, theoretical number average molecular weight, number average molecular weight and molecular weight distribution in the same manner as in Example 12. The results obtained are shown in Table 7-1. Calculation of a theoretical number average molecular weight of the graft chain, treatment of the polymer with hydrofluoric acid, measurement of a number average molecular weight of the graft chain by GPC measurement, and analysis of molecular weight distribution were carried out in the same manners as in Example 12. The results obtained are shown in Table 7-2.

TABLE 7-1

| Example | Polymer | Polymerization time (hr) | Conversion (% by mole) | Mn Calculated value | Mn Found value | Mw/Mn Found value |
|---|---|---|---|---|---|---|
| 12 | 2a | 0.25 | 14.6 | 6,000 | 6,500 | 1.12 |
| 13 | 2b | 0.5 | 35.9 | 12,400 | 12,000 | 1.17 |
| 14 | 2c | 1.0 | 53.6 | 17,700 | 17,200 | 1.16 |
| 15 | 2d | 1.5 | 67.8 | 22,000 | 22,300 | 1.15 |
| 16 | 2e | 2.0 | 79.0 | 25,400 | 25,200 | 1.16 |
| 17 | 2f | 2.5 | 82.8 | 26,500 | 28,000 | 1.16 |
| 18 | 2g | 3.0 | 87.1 | 27,800 | 30,900 | 1.16 |

TABLE 7-2

| Example | Polymer | Mn Calculated value | Mn Found value | Mw/Mn Found value |
|---|---|---|---|---|
| 12 | 2a | 2,400 | 4,300 | 1.12 |
| 13 | 2b | 5,600 | 6,500 | 1.17 |
| 14 | 2c | 8,200 | 9,100 | 1.16 |
| 15 | 2d | 10,300 | 11,500 | 1.15 |
| 16 | 2e | 12,000 | 13,200 | 1.16 |
| 17 | 2f | 12,600 | 15,200 | 1.16 |
| 18 | 2g | 13,200 | 15,300 | 1.16 |

Example 19

Synthesis of Compound (3-2-1): silanol-containing phenyl silsesquioxane Starting from Compound (3-1-1)

A reaction vessel having an internal volume of 100 mL and equipped with a dropping funnel and a thermometer was charged with Compound (3-1-1) (6 g) as obtained in Example 1 and tetrahydrofuran (50 mL) and then sealed with dry nitrogen. Glacial acetic acid (2.4 g) was added dropwise with stirring over about 10 seconds while keeping the solution temperature at 22 to 27° C. After completion of dropwise addition, stirring was continued at room temperature for one hour, and ion-exchanged water (20 g) was then added dropwise. After completion of the dropwise addition, stirring was continued for 10 minutes, and the mixture was then transferred into a separating funnel, thereby separating an organic layer and an aqueous layer. The thus obtained organic layer was washed once with saturated sodium hydrogencarbonate water, and water washing with ion-exchanged water was repeated until the organic layer became neutral. Subsequently, the organic layer was dried over anhydrous magnesium sulfate and then concentrated in vacuo to obtain 5.3 g of a white powdered solid.

The white powdered solid thus obtained was subjected to IR analysis. As a result, absorption on the basis of expansion and contraction of Si—OH was confirmed at 3,300 cm$^{-1}$. As a result of the measurement of $^{29}$Si-NMR, one signal derived from a structure represented by PhSi(OH)O$_{2/2}$ and one signal derived from a structure represented by PhSiO$_{3/2}$ were confirmed at −69.32 ppm and −79.45 ppm, respectively. As a result of the measurement of $^1$H-NMR, any signal other than a phenyl group was not confirmed. As a result of the measurement of an average molecular weight by GPC, a number average molecular weight and a weight average molecular weight as reduced into polystyrene were 760 and 780, respectively. These data suggest that the resulting white powdered solid has a structure represented by Formula (3-2-1).

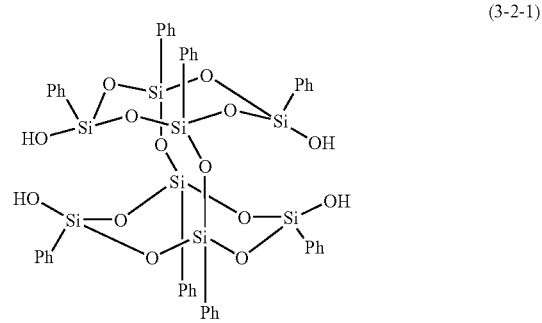

(3-2-1)

Example 20

Synthesis of Compound (5-1): Organosilicon Compound Having Hydrosilyl Group

Compound (5-1) can be synthesized by carrying out the same operations as in Example 3, except for using Compound (3-2-1) as obtained in Example 19 in place of Compound (3-1-1) as obtained in Example 1.

Example 21

Synthesis of Silicon Compound Having Hydroxypropyl Group

A compound represented by Formula (7-2) can be obtained by carrying out the same operations as in Example 4, except for using allyl alcohol (4.0 equivalents or more to Compound (5-1)) in place of ethylene glycol monoallyl ether.

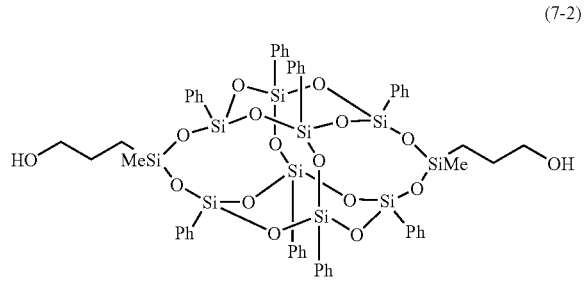
(7-2)

Example 22

Synthesis of Silicon Compound Having 2-bromo-2-methylpropanoyloxypropyl Group A silicon compound represented by Formula (1-1-4) can be synthesized by carrying out the same operations as in Example 5, except for Compound (7-2) as obtained in Example 21 in place of Compound (7-1) as obtained in Example 4.

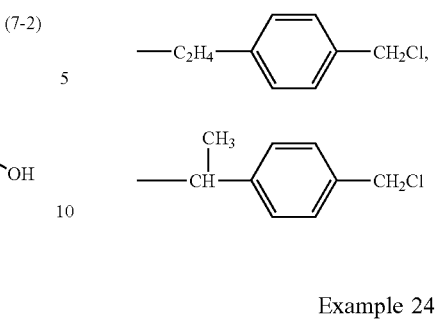

Example 24

Synthesis of Silicon Compound Having Dithiocarbamoyl Group

A silicon compound having a dithiocarbamoyl group represented by Formula (1-4-3) can be synthesized by using Compound (1-3-3) as obtained in Example 23 as a raw material and reacting sodium N,N-diethyldithiocarbamate trihydrate (1.0 equivalent or more to the chloromethylphenylethyl group) therewith in tetrahydrofuran.

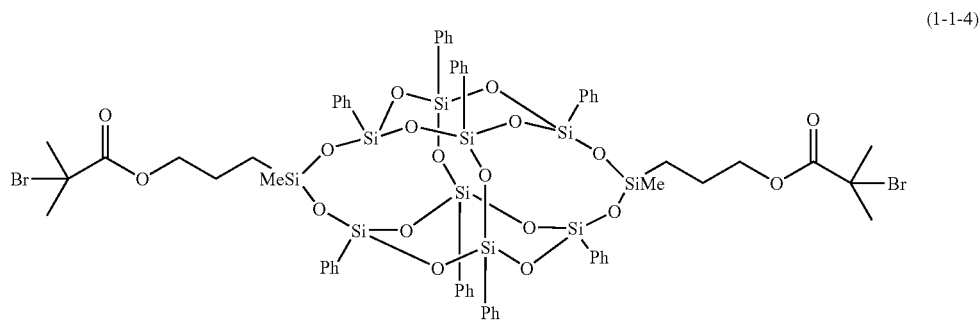
(1-1-4)

Example 23

Synthesis of Silicon Compound Having chloromethylphenylethyl Group

A silicon compound represented by Formula (1-3-3) can be synthesized by carrying out the same operations as in Example 4, except for except using chloromethylstyrene (4.0 equivalents or more to Compound (5-1)) in place of ethylene glycol monoallyl ether.

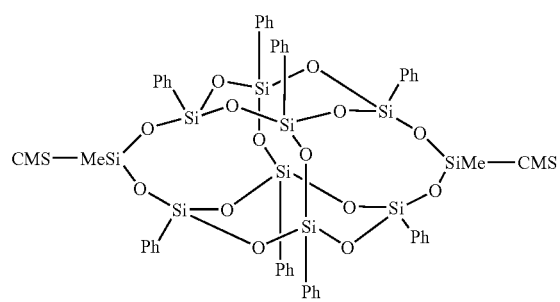
(1-3-3)

In this formula, CMS is a group represented by any one of following formulae.

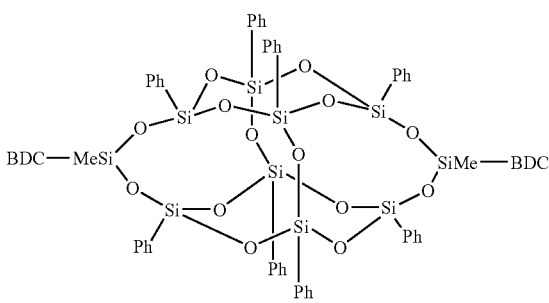
(1-4-3)

In this formula, BDC is a group represented by any one of following formulae.

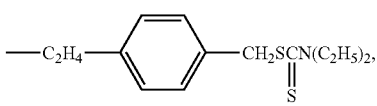

-continued

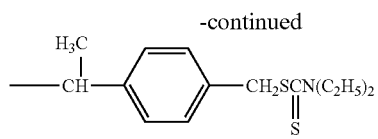

Example 25

Synthesis of 2-bromo-2-methylpropanoyloxypropyl-methyldichlorosilane

A compound represented by Formula (10) is synthesized by using allyl alcohol as a raw material and reacting 2-bromo-2-methylpropanoyl bromide (1.0 equivalent or more to the hydroxyl group) therewith in methylene chloride in the presence of triethylamine (1.0 equivalent or more to the hydroxyl group). In addition, 2-bromo-2-methylpropanoyloxypropylmethyldichlorosilane represented by Formula (11-1) can be synthesized by subjecting Compound (10) and methyldichlorosilane (1.0 equivalent or more to the allyl group) to a hydrosilylation reaction by using a platinum-divinyltetramethyldisiloxane complex/xylene solution ($1 \times 10^{-6}$ to $1 \times 10^{-2}$ moles as a transition metal catalyst atom per mole of the Si—H group) as a catalyst.

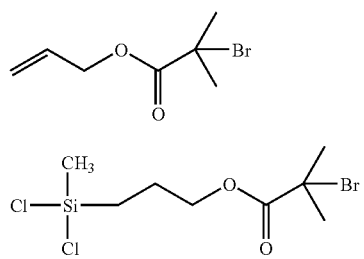

Example 26

Synthesis of Silicon Compound Having 2-bromo-2-methylpropanoyloxypropyl Group

A silicon compound represented by Formula (1-1-4) can be synthesized by carrying out the same operations as in Example 3, except for using 2-bromo-2-methylpropanoyloxypropylmethyldichlorosilane (4.0 equivalents or more to Compound (3-1-1)) as obtained in Example 25 in place of methyldichlorosilane.

Example 27

Synthesis of Silicon Compound Having 2-bromo-2-methylpropanoyloxypropyl Group

The silicon compound represented by Formula (1-1-4) can be synthesized by carrying out the same operations as in Example 26, except for using Compound (3-2-1) in place of Compound (3-1-1).

Example 28

Synthesis of 2-bromo-2-methylpropanoyloxyethoxypropylmethyldichlorosilane

2-Bromo-2-methylpropanoyloxyethoxypropylmethyldichlorosilane represented by Formula (11-2) can be synthesized by carrying out the same operations as in Example 25, except for using ethylene glycol monoallyl ether in place of allyl alcohol.

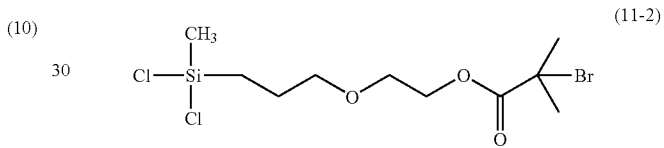

Example 29

Synthesis of Silicon Compound Having 2-bromo-2-methylpropanoyloxyethoxypropyl Group A silicon compound represented by Formula (1-1-3) can be synthesized by carrying out the same operations as in Example 26, except for using 2-bromo-2-methylpropanoyloxyethoxypropylmethyldichlorosilane (4.0 equivalents or more to Compound (3-1-1)) as obtained in Example 28 in place of 2-bromo-2-methylpropanoyloxypropylmethyldichlorosilane as obtained in Example 25.

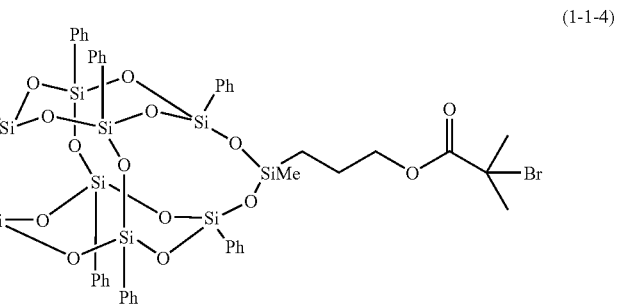

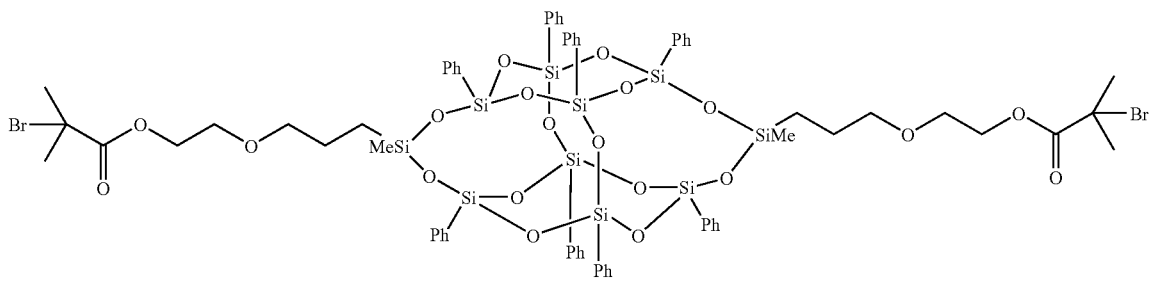

(1-1-3)

Example 30

Synthesis of Silicon Compound Having 2-bromo-2-methylpropanoyloxyethoxypropyl Group The silicon compound represented by Formula (1-1-3) can be synthesized by carrying out the same operations as in Example 29, except for using Compound (3-2-1) in place of Compound (3-1-1).

Example 31

Synthesis of (chloromethylphenylethyl)methyldichlorosilane (Chloromethylphenylethyl)methyldichlorosilane represented by Formula (11-3) can be synthesized by carrying out the same operations as in Example 25, except for using chloromethylstyrene in place of allyl alcohol.

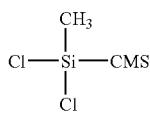

(11-3)

In this formula, CMS is a group represented by any one of following formulae.

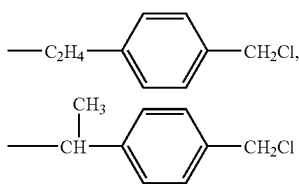

Example 32

Synthesis of Silicon Compound Having chloromethylphenylethyl Group

A silicon compound represented by Formula (1-3-3) can be synthesized by carrying out the same operations as in Example 26, except for using (chloromethylphenylethyl)methyldichlorosilane (4.0 equivalents or more to Compound (3-1-1)) as obtained in Example 31 in place of (2-bromo-2-methylpropanoyloxypropyl)methyldichlorosilane as obtained in Example 25.

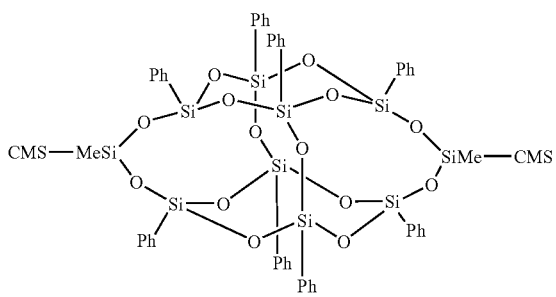

(1-3-3)

In this formula, CMS is the same as CMS in Formula (11-3).

Example 33

Synthesis of Silicon Compound Having Chloromethylphenylethyl Group

The silicon compound represented by Formula (1-3-3) can be synthesized by carrying out the same operations as in Example 32, except for using Compound (3-2-1) in place of Compound (3-1-1).

Example 34

Synthesis of (chlorosulfonylphenylethyl)methyldichlorosilane (Chlorosulfonylphenylethyl)methyldichlorosilane represented by Formula (11-4) can be synthesized by carrying out the same operations as in Example 25, except for using chlorosulfonylstyrene in place of allyl alcohol.

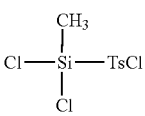

(11-4)

In this formula, TsCl is a group represented by any one of following formulae.

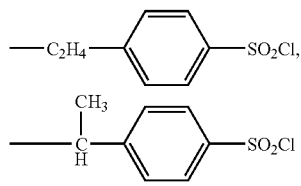

Example 35

Synthesis of Silicon Compound Having Chlorosulfonylphenylethyl Group

A silicon compound represented by Formula (1-2-3) can be synthesized by carrying out the same operations as in Example 26, except for using (chlorosulfonylphenylethyl)methyldichlorosilane (4.0 equivalents or more to Compound (3-1-1)) as obtained in Example 34 in place of 2-bromomethylpropanoyloxypropylmethyldichlorosilane as obtained in Example 25.

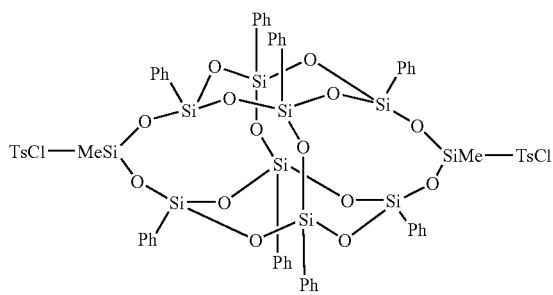

(1-2-3)

In this formula, TsCl is the same as TsCl in Formula (11-4).

Example 36

Synthesis of Silicon Compound Having Chlorosulfonylphenylethyl Group

The silicon compound represented by Formula (1-2-3) can be synthesized by carrying out the same operations as in Example 35, except for using Compound (3-2-1) in place of Compound (3-1-1).

Example 37

Preparation of Ordered Structure Thin Film 0.25 g of Polymer (a) as obtained in Example 7 was dissolved in 0.75 g of tetrahydrofuran to obtain a solution having a concentration of the polymer of 25% by weight. Respective solutions of Polymers (2a) and (2b) as obtained in Examples 12 and 13 were obtained in the same manner. Each of the resulting solutions was coated on a glass substrate and dried at room temperature for 24 hours to obtain a thin film. As a result of observation by a scanning electron microscope (SEM), each of the resulting thin films had an ordered structure as shown in FIGS. 1 to 3. A pore size as estimated from each of the SEM images is shown in Table 8.

TABLE 8

| Polymer | Number average molecular weight (Mn) | Pore size (nm) |
| --- | --- | --- |
| 2a | 6,500 | 100 |
| 2b | 12,000 | 200 |
| a | 20,200 | 600 |

INDSUTRIAL APPLICABILITY

The silicon compound to be provided by the invention is a silsesquioxane derivative and has excellent a living polymerizable radical polymerization initiating function. The silicon compound of the invention exhibits an excellent living radical polymerization promoting function especially for (meth)acrylic acid derivatives and styrene derivatives. For example, by initiating polymerization of a (meth)acrylic monomer by the silicon compound of the invention, it is possible to form a (meth)acrylic polymer by starting from two points of the silsesquioxane structure of the invention. With respect to the thus obtained polymer having an organic group of a silsesquioxane structure in the center thereof, it is also possible to positively utilize a mutual action between organic groups of the silsesquioxane structure. In this way, not only an organic-inorganic composite material having a distinct structure can be obtained, but also the structure as a molecular agglomerate of this polymer can be controlled. In addition, this polymer can be utilized as a resin modifier upon mixing with an existing resin. The silicon compound of the invention also has characteristics other than the function as a polymerization initiator. For example, since an α-haloester has strong electrophilicity, by reacting the silicon compound of the invention and a nucleophilic reagent, a variety of silsesquioxane derivatives can be synthesized depending upon the nucleophilic reagent. Accordingly, the silicon compound of the invention is useful as an intermediate in organic synthesis, too.

The invention claimed is:
1. A silicon compound represented by Formula (1):

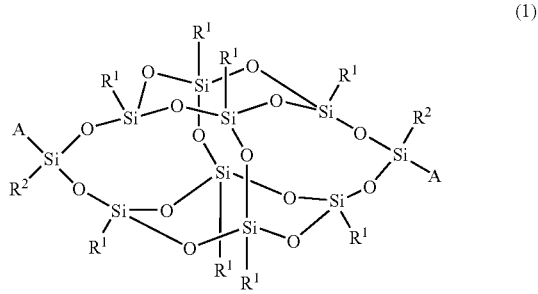

(1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and A is a group having a polymerization initiating ability for addition polymerizable monomers.

2. The silicon compound according to claim 1, wherein each $R^1$ is a group independently selected from hydrogen, an alkyl having 1 to 45 carbon atoms in which arbitrary hydrogen may be replaced by fluorine and arbitrary —$CH_2$— may be replaced by —O— or a cycloalkylene, a substituted or unsubstituted aryl, and an arylalkyl constituted of a substituted or unsubstituted aryl group and an alkylene group in which arbitrary hydrogen may be replaced by fluorine and arbitrary —$CH_2$— may be replaced by —O—or a cycloalkylene; each $R^2$ is a group independently selected from an alkyl having 1 to 8 carbon atoms, phenyl, and cyclohexyl; and A is a group having a living radical polymerization initiating ability for addition polymerizable monomers.

3. The silicon compound according to claim 1, wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and A is a group represented by any one of Formula (2-1), formula (2-2), formula (2-3) and formula (2-4):

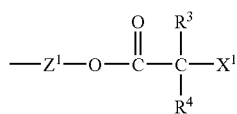
(2-1)

wherein $Z^1$ is an alkylene having 3 to 20 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

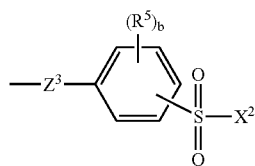
(2-2)

wherein $Z^3$ is an alkylene having 2 to 10 carbon atoms in which arbitrary —$CH_2$— may be replaced by —O—, —COO—, or —OCO—; $R^5$ is an alkyl having 1 to 3 carbon atoms; b is an integer of 0 to 2; $X^2$ is a halogen; the bonding position of —$SO_2X^2$ on the benzene ring is an ortho-position, a meta-position, or a para-position with respect to the bonding position of $Z^3$; and the bonding position of $R^5$ is an arbitrary position excluding the respective bonding positions of $Z^3$ and —$SO_2X^2$;

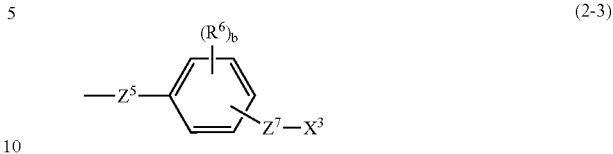
(2-3)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^5$; and the bonding position of $R^6$ is an arbitrary position excluding the respective bonding positions of $Z^5$ and $Z^7$;

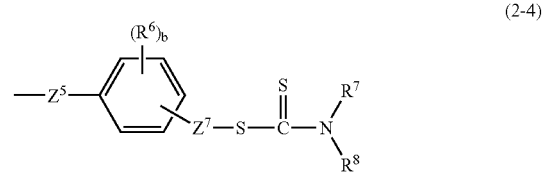
(2-4)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-positive with respect to the bonding position of $Z^5$; and the bonding position of $R^6$ is an arbitrary position excluding the respective bonding positions of $Z^5$ and $Z^7$.

4. The silicon compound according to claim 3, wherein each $R^1$ is a group independently selected from hydrogen and an alkyl having 1 to 30 carbon atoms; and in this alkyl, arbitrary hydrogen may be replaced by fluorine, and arbitrary —$CH_2$— may be replaced by —O— or a cycloalkylene.

5. The silicon compound according to claim 3, wherein each $R^1$ is a group independently selected from phenyl in which arbitrary hydrogen may be replaced by a halogen or an alkyl having 1 to 10 carbon atoms and unsubstituted naphthyl; in the alkyl as a substituent of the phenyl, arbitrary hydrogen may be replaced by fluorine, and arbitrary —$CH_2$— may be replaced by —O—, a cycloalkylene, or phenylene; and when the phenyl has plural substituents, those substituents may be the same group or a different group.

6. The silicon compound according to claim 3, wherein each $R^1$ is a group independently selected from a phenylalkyl constituted of a phenyl group in which arbitrary hydrogen may be replaced by a halogen or an alkyl having 1 to 12 carbon atoms and an alkylene group having 1 to 12 carbon atoms in which arbitrary hydrogen may be replaced by fluorine, and arbitrary —CH$_2$— may be replaced by —O— or a cycloalkylene; in the alkyl as a substituent of the phenyl group, arbitrary hydrogen may be replaced by fluorine, and arbitrary —CH$_2$— may be replaced by —O—, a cycloalkylene, or phenylene; and when the phenyl group has plural substituents, those substituents may be the same group or a different group.

7. The silicon compound according to claim 3, wherein each R$^1$ is a group independently selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; in the alkyl having 1 to 8 carbon atoms, arbitrary hydrogen may be replaced by fluorine, and arbitrary —CH$_2$— may be replaced by —O— or a cycloalkylene; and when the phenyl or the phenyl group of the phenylalkyl has plural substituents, those substituents may be the same group or a different group.

8. The silicon compound according to claim 3, wherein all R$^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; in the alkyl having 1 to 8 carbon atoms, arbitrary hydrogen may be replaced by fluorine, and arbitrary —CH$_2$— may be replaced by —O— or a cycloalkylene; when the phenyl or the phenyl group of the phenylalkyl has plural substituents, those substituents may be the same group or a different group; and each R$^2$ is a group independently selected from an alkyl having 1 to 4 carbon atoms, phenyl, and cyclohexyl.

9. The silicon compound according to claim 3, wherein R$^1$ is phenyl.

10. The silicon compound according to claim 3, wherein R$^1$ is phenyl; and R$^2$ is methyl.

11. The silicon compound according to claim 3, wherein all R$^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; in the alkyl having 1 to 8 carbon atoms, arbitrary hydrogen may be replaced by fluorine, and arbitrary —CH$_2$— may be replaced by —O— or a cycloalkylene; when the phenyl or the phenyl group of the phenylalkyl has plural substituents, those substituents may be the same group or a different group; each R$^2$ is a group independently selected from an alkyl having 1 to 4 carbon atoms, phenyl, and cyclohexyl; and A is a group represented by Formula (2-1):

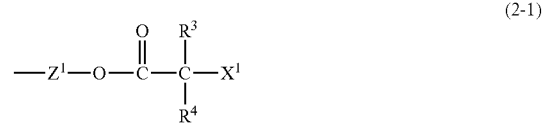

(2-1)

wherein Z$^1$ is an alkylene having 3 to 20 carbon atoms, and arbitrary —CH$_2$— in this alkylene may be replaced by —O—; R$^3$ is hydrogen, an alkyl having 1 to 20 carbon atoms, an aryl having 6 to 20 carbon atoms, or an arylalkyl having 7 to 20 carbon atoms; R$^4$ is an alkyl having 1 to 20 carbon atoms, an aryl having 6 to 20 carbon atoms, or an arylalkyl having 7 to 20 carbon atoms; and X$^1$ is a halogen.

12. The silicon compound according to claim 11, wherein R$^1$ is phenyl; and Z$^1$ is an alkylene having 3 to 10 carbon atoms in which arbitrary —CH$_2$— may be replaced by —O—.

13. The silicon compound according to claim 11, wherein R$^1$ is phenyl; R$^2$ is methyl; Z$^1$ is —C$_3$H$_6$— or —C$_3$H$_6$—O—C$_2$H$_4$—; R$^3$ and R$^4$ are each methyl; and X$^1$ is bromine.

14. The silicon compound according to claim 3, wherein all R$^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; in the alkyl having 1 to 8 carbon atoms, arbitrary hydrogen may be replaced by fluorine, and arbitrary —CH$_2$— may be replaced by —O— or a cycloalkylene; when the phenyl or the phenyl group of the phenylalkyl has plural substituents, those substituents may be the same group or a different group; each R$^2$ is a group independently selected from an alkyl having 1 to 4 carbon atoms, phenyl, and cyclohexyl; and A is a group represented by Formula (2-2):

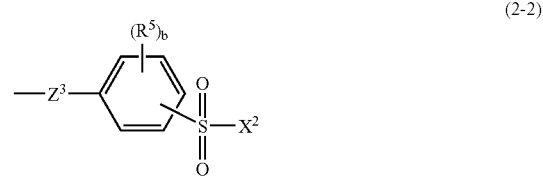

(2-2)

wherein Z$^3$ is an alkylene having 2 to 10 carbon atoms in which arbitrary —CH$_2$— may be replaced by —O—, —COO—, or —OCO—; R$^5$ is an alkyl having 1 to 3 carbon atoms; b is an integer of 0 to 2; X$^2$ is a halogen; the bonding position of —SO$_2$X$^2$ on the benzene ring is an ortho-position, a meta-position, or a para-position with respect to the bonding position of Z$^3$; and the bonding position of R$^5$ is an arbitrary position excluding the respective bonding positions of Z$^3$ and —SO$_2$X$^2$.

15. The silicon compound according to claim 14, wherein R$^1$ is phenyl; Z$^3$ is —C$_2$H$_4$—Z$^4$; and Z$^4$ is a single bond or an alkylene having 1 to 8 carbon atoms in which arbitrary —CH$_2$— may be replaced by —O—, —COO—, or —OCO—.

16. The silicon compound according to claim 14, wherein $R^1$ is phenyl; $R^2$ is methyl; $Z^3$ is —$C_2H_4$—; $X^2$ is chlorine or bromine; and b is 0.

17. The silicon compound according to claim 3, wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-3):

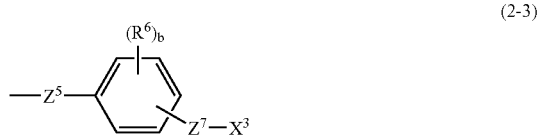

(2-3)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^5$; and the bonding position of $R^6$ is an arbitrary position excluding the respective bonding positions of $Z^5$ and $Z^7$.

18. The silicon compound according to claim 17, wherein $R^1$ is phenyl; $Z^5$ is —$C_2H_4$—$Z^6$; and $Z^6$ is a single bond or an alkylene having 1 to 8 carbon atoms in which arbitrary —$CH_2$— may be replaced by —O—, —COO—, or —OCO—.

19. The silicon compound according to claim 17, wherein $R^1$ is phenyl; $R^2$ is methyl; $Z^5$ is —$C_2H_4$—; $Z^7$ is —$CH_2$—; $X^3$ is chlorine or bromine; and b is 0.

20. The silicon compound according to claim 3, wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and A is a group represented by Formula (2-4):

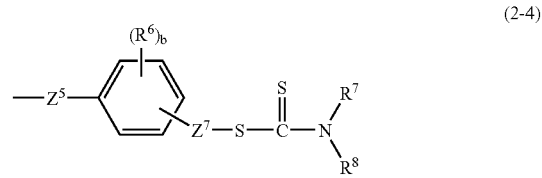

(2-4)

wherein $Z^5$ is an alkylene having 2 to 10 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-positive with respect to the bonding position of $Z^5$; and the bonding position of $R^6$ is an arbitrary position excluding the respective bonding positions of $Z^5$ and $Z^7$.

21. The silicon compound according to claim 20, wherein $R^1$ is phenyl; $Z^5$ is —$C_2H_4$—$Z^6$; and $Z^6$ is a single bond or an alkylene having 1 to 8 carbon atoms in which arbitrary —$CH_2$— may be replaced by —O—, —COO—, or —OCO—.

22. The silicon compound according to claim 20, wherein $R^1$ is phenyl; $R^2$ is methyl; $Z^5$ is —$C_2H_4$—; $R^7$ and $R^8$ are each ethyl; $Z^7$ is —$CH_2$—; and b is 0.

23. A process for producing a silicon compound represented by Formula (1-1), characterized by carrying out the following step (a), step (b) and step (c), successively:

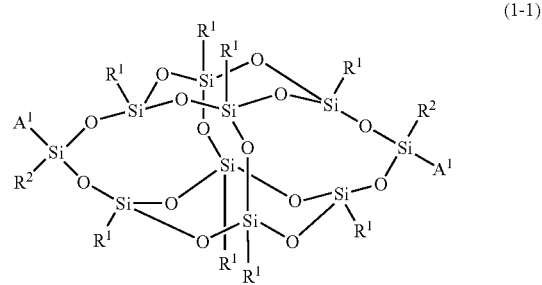

(1-1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

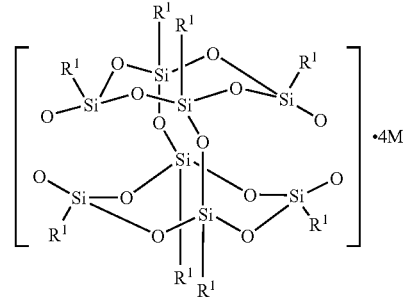

(3-1)

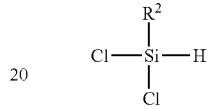

(4)

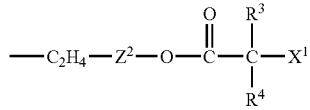

(2-1-1)

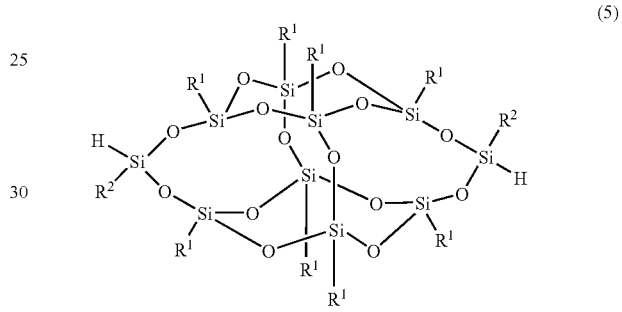

(5)

wherein $Z^2$ is an alkylene having 1 to 18 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; R is an alkyl having 1 to 20 carbon atoms, an aryl having 6 to 20 carbon atoms, or an arylalkyl having 7 to 20 carbon atoms; and $X^1$ is a halogen;

Step (a)

A step for reacting a compound represented by Formula (3-1) and a compound represented by Formula (4) to obtain a compound represented by Formula (5):

wherein $R^1$ and $R^2$ have the same meanings as those in Formula (1-1), respectively; and M is a monovalent alkali metal atom;

Step (b)

A step for reacting the compound represented by Formula (5) and a compound represented by Formula (6) in the presence of a transition metal catalyst to obtain a silicon compound represented by Formula (7):

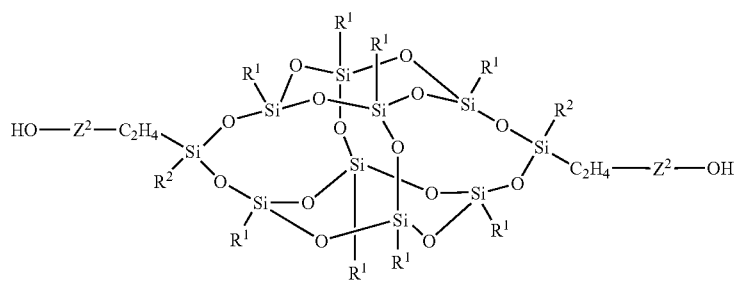

(7)

wherein $Z^2$ has the same meaning as $Z^2$ in Formula (2-1-1); and $R^1$ and $R^2$ have the same meanings as those in Formula (1-1), respectively;

Step (c)

A step for reacting the compound represented by Formula (7) and a compound represented by Formula (8) to obtain the silicon compound represented by Formula (1-1):

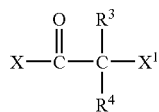
(8)

wherein $R^3$, $R^4$ and $X^1$ have the same meanings as those in Formula (2-1-1), respectively; and X is a halogen.

24. The process according to claim 23, wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; in the alkyl having 1 to 8 carbon atoms, arbitrary hydrogen may be replaced by fluorine, and arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

25. The process according to claim 23, wherein $R^1$ is phenyl; and $R^2$ is methyl.

26. A process for producing a silicon compound represented by Formula (1-1), characterized by carrying out the following step (d), step (b) and step (c), successively:

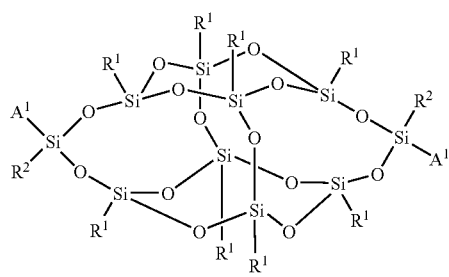
(1-1)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

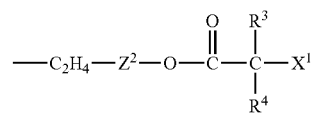
(2-1-1)

wherein $Z^2$ is a single bond or an alkylene having 1 to 18 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

Step (d)

A step for reacting a compound represented by Formula (3-2) and a compound represented by Formula (4) to obtain a compound represented by following formula (5):

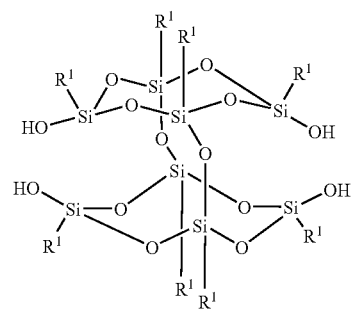
(3-2)

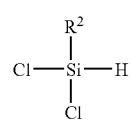
(4)

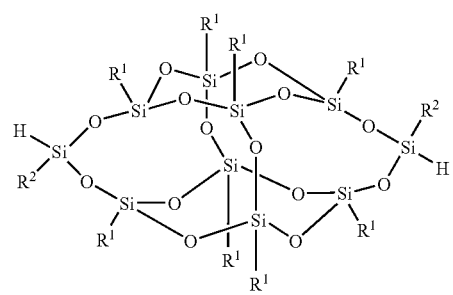
(5)

wherein $R^1$ and $R^2$ have the same meanings as those in Formula (1-1), respectively;

Step (b)

A step for reacting the compound represented by Formula (5) and a compound represented by Formula (6) in the presence of a transition metal catalyst to obtain a silicon compound represented by Formula (7):

$CH_2$=$CH$—$Z^2$—$OH$ (6)

(7)

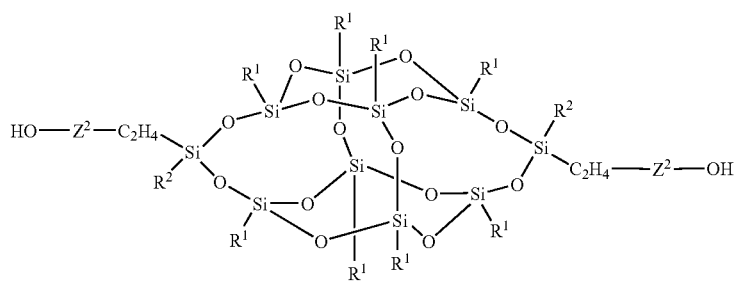

wherein $Z^2$ has the same meaning as $Z^2$ in Formula (2-1-1); and $R^1$ and $R^2$ have the same meanings as those in Formula (1-1), respectively;

Step (c)

A step for reacting the compound represented by Formula (7) and a compound represented by Formula (8) to obtain the silicon compound represented by Formula (1-1):

(8)

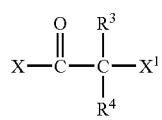

wherein $R^3$, $R^4$ and $X^1$ have the same meanings as those in Formula (2-1-1), respectively; and X is a halogen.

27. The process according to claim 26, wherein all $R^1$s are the same group selected from an alkyl having 1 to 8 carbon atoms, phenyl in which arbitrary hydrogen may be replaced by a halogen, methyl or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; in the alkyl having 1 to 8 carbon atoms, arbitrary hydrogen may be replaced by fluorine, and arbitrary —CH$_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

28. The process according to claim 26, wherein $R^1$ is phenyl; and $R^2$ is methyl.

29. A process for producing a silicon compound represented by Formula (1-3), characterized by carrying out the following step (e) and step (f), successively:

(1-3)

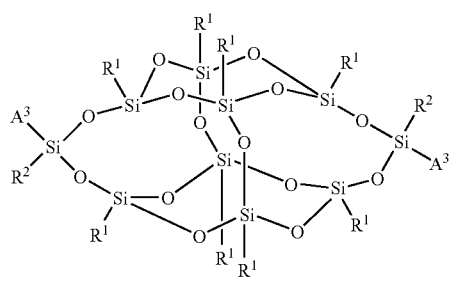

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —CH$_2$— may be replaced by —O— or a cycloalkylene; in the alkylene group of the arylalkyl, arbitrary hydrogen may be replaced by fluorine, and arbitrary —CH$_2$— may be replaced by —O— or a cycloalkylene; each $R^2$ is a group independently selected from an alkyl having 1 to 8 carbon atoms, phenyl, and cyclohexyl; and $A^3$ is a group represented by Formula (2-3-1):

(2-3-1)

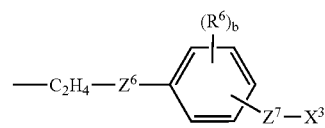

wherein $Z^6$ is a single bond or an alkylene having 1 to 8 carbon atoms in which arbitrary —CH$_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —CH$_2$— may be replaced by —O—; $X^3$ is a halogen; the bonding position of $Z^7$ on the benzene ring is a meta-position or a para-position with respect to the bonding position of $Z^6$; and the bonding position of $R^6$ is an arbitrary position excluding the respective bonding positions of $Z^6$ and $Z^7$;

Step (e)

A step for reacting a compound represented by Formula (4) and a compound represented by Formula (3-1) or a compound represented by Formula (3-2) to obtain a silicon compound represented by Formula (5):

(4)

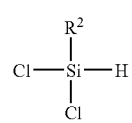

-continued

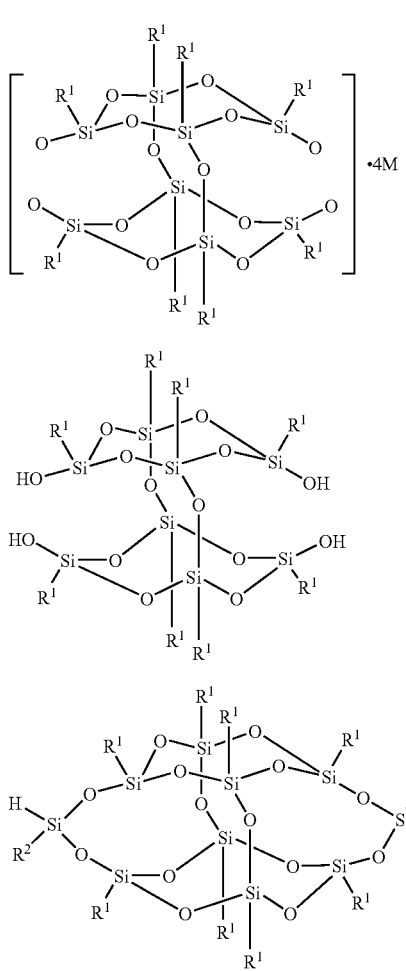

(3-1)

(3-2)

(5)

wherein $R^1$ and $R^2$ have the same meanings as those in Formula (1-3), respectively; and M is a monovalent alkali metal atom;

Step (f)

A step for reacting the compound represented by Formula (5) and a compound represented by Formula (2-3-2) to obtain the silicon compound represented by Formula (1-3):

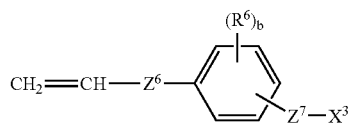

(2-3-2)

wherein $Z^6$, $R^6$, b, $Z^7$ and $X^3$ have the same meanings as those in Formula (2-3-1), respectively; and the bonding positions of $Z^7$ and $R^6$ on the benzene ring are the same as the bonding positions of $Z^7$ and $R^6$ in Formula (2-3-1), respectively.

30. The process according to claim 29, wherein all $R^1$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

31. The process according to claim 29, wherein $R^1$ is phenyl; and $R^2$ is methyl.

32. A process for producing a silicon compound represented by Formula (1-4), characterized by reacting a silicon compound represented by the formula (1-3) and a compound represented by the formula (9):

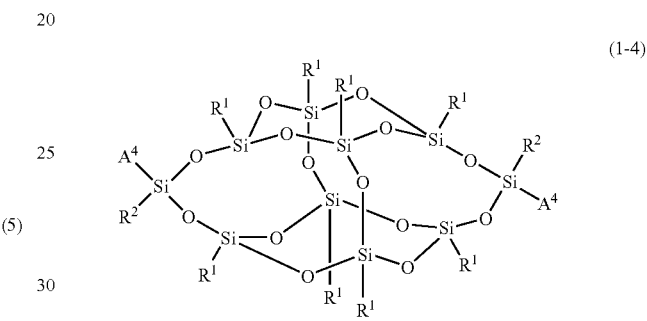

(1-4)

wherein each $R^1$ is a group independently selected from hydrogen, an alkyl having 1 to 45 carbon atoms in which arbitrary hydrogen may be replaced by fluorine and arbitrary —$CH_2$— may be replaced by —O— or a cycloalkylene, a substituted or unsubstituted aryl, and an arylalkyl constituted of a substituted or unsubstituted aryl group and an alkylene group in which arbitrary hydrogen may be replaced by fluorine and arbitrary —$CH_2$— may be replaced by —O— or a cycloalkylene; each $R^2$ is group independently selected from an alkyl having 1 to 8 carbon atoms, phenyl, and cyclohexyl; and $A^4$ is a group represented by Formula (2-4-1):

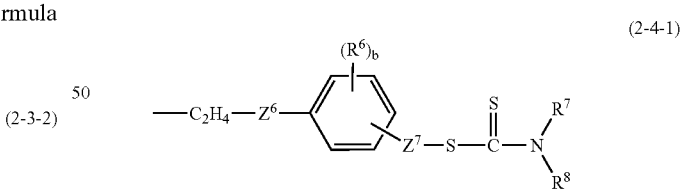

(2-4-1)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-position with respect to the bonding position of $Z^6$; and the bonding position of $R^6$ is an arbitrary position excluding the respective bonding positions of $Z^6$ and $z^7$;

(1-3)
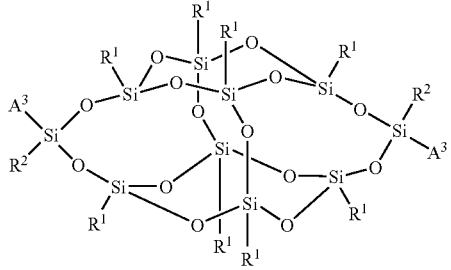

wherein $R^1$ and $R^2$ have the same meanings as those in Formula (1-4), respectively; and $A^3$ is a group represented by Formula (2-3-1):

(2-3-1)
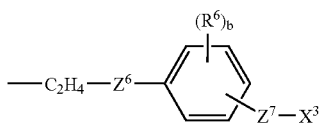

wherein $Z^6$, $R^6$, b, and $Z^7$ have the same meanings as those in Formula (2-4-1), respectively; $X^3$ is a halogen; and the bonding positions of $Z^7$ and $R^6$ on the benzene ring are the same as the bonding positions of $Z^7$ and $R^6$ in Formula (2-4-1), respectively;

(9)
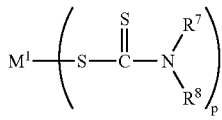

wherein $R^7$ and $R^8$ have the same meanings as those in Formula (2-4-1), respectively; $M^1$ is a metal atom belonging to the group 1 or group 2 of the periodic table; and p is a value equal to the valence of $M^1$.

33. The process according to claim 32, wherein all $R^1$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

34. The process according to claim 32, wherein $R^1$ is phenyl; and $R^2$ is methyl.

35. A process for producing a silicon compound represented by Formula (1-1), characterized by carrying out the following step (g) and step (h), successively:

(1-1)
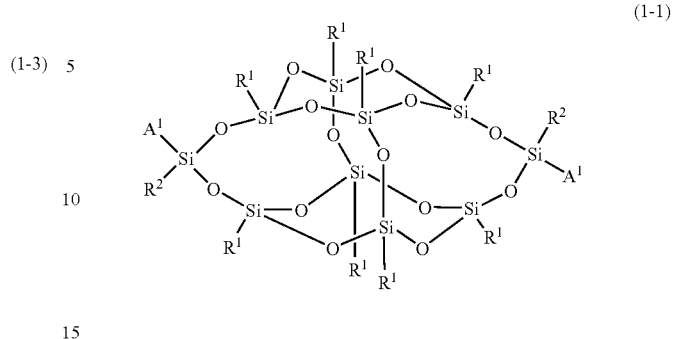

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —$CH_2$— may be replaced by —O— or a cycloalkylene; in the alkylene group of the arylalkyl, arbitrary hydrogen may be replaced by fluorine, and arbitrary —$CH_2$— may be replaced by —O— or a cycloalkylene; each $R^2$ is a group independently selected from an alkyl having 1 to 8 carbon atoms, phenyl, and cyclohexyl; and $A^1$ is a group represented by Formula (2-1-1):

(2-1-1)
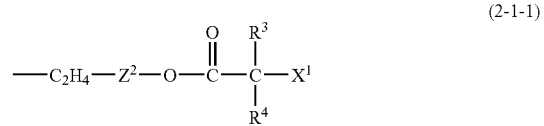

wherein $Z^2$ is an alkylene having 1 to 18 carbon atoms, and arbitrary —$CH_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; and $X^1$ is a halogen;

Step (g)
A step for reacting a compound represented by Formula (4) and a compound represented by Formula (2-1-2) in the presence of a transition metal catalyst to obtain a compound represented by Formula (2-1-3):

(4)

(2-1-2)
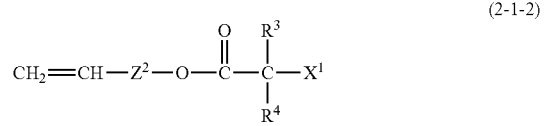

(2-1-3)
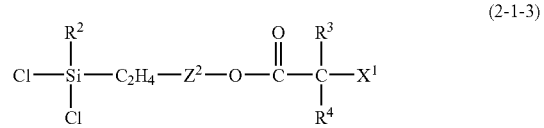

wherein R² has the same meaning as R² in Formula (1-1); and Z², R³, R⁴, and X¹ have the same meanings as those in Formula (2-1-1), respectively;

Step (h)

A step for reacting the compound represented by Formula (2-1-3) and a compound represented by Formula (3-1) or a compound represented by Formula (3-2) to obtain the silicon compound represented by Formula (1-1):

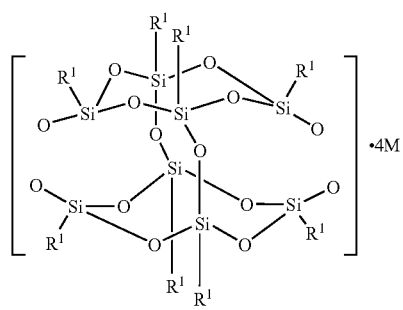

(3-1)

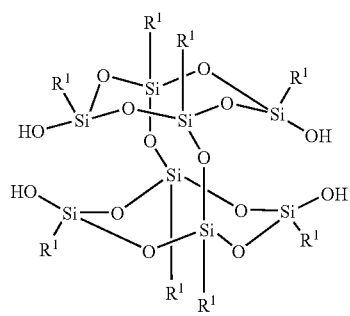

(3-2)

wherein R¹ has the same meaning as R¹ in Formula (1-1); and M is a monovalent alkali metal atom.

36. The process according to claim 35, wherein all R¹'s are the same group selected from an alkyl having 1 to 8 carbon atoms in which arbitrary hydrogen may be replaced by fluorine and arbitrary —CH₂— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH₂— may be replaced by —O— or a cycloalkylene; when the phenyl or the phenyl group of the phenylalkyl has plural substituents, those substituents may be the same group or a different group; and each R²is a group independently selected from an alkyl having 1 to 4 carbon atoms, phenyl, and cyclohexyl.

37. The process according to claim 35, wherein R¹ is phenyl; and R² is methyl.

38. A process for producing a silicon compound represented by Formula (1-2), characterized by carrying out the following step (i) and step (j), successively:

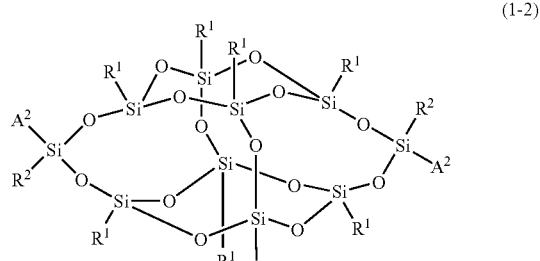

(1-2)

wherein each R¹ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —CH₂— may be replaced by —O— or a cycloalkylene; in the alkylene group of the arylalkyl, arbitrary hydrogen may be replaced by fluorine, and arbitrary —CH₂— may be replaced by —O— or a cycloalkylene; each R² is a group independently selected from an alkyl having 1 to 8 carbon atoms, phenyl, and cyclohexyl; and A² is a group represented by Formula (2-2-1):

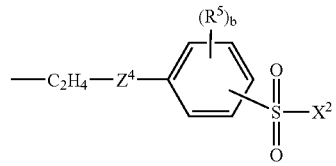

(2-2-1)

wherein Z⁴ is a single bond or an alkylene having 1 to 8 carbon atoms, and arbitrary —CH₂— in this alkylene may be replaced by —O—, —COO—, or —OCO—; R⁵ is an alkyl having 1 to 3 carbon atoms; b is an integer of 0 to 2; X² is a halogen; the bonding position of —SO₂X² on the benzene ring is an ortho-position, a meta-position, or a para-position with respect to the bonding position of Z⁴; and the bonding position of R⁵ is an arbitrary position excluding the respective bonding positions of Z⁴ and —SO₂X²;

Step (i)

A step for reacting a compound represented by Formula (4) and a compound represented by Formula (2-2-2) in the presence of a transition metal catalyst to obtain a compound represented by Formula (2-2-3):

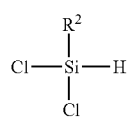

(4)

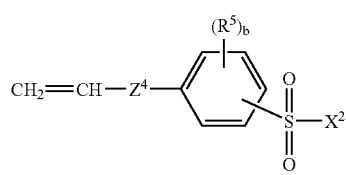

(2-2-2)

-continued

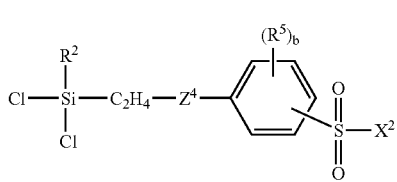
(2-2-3)

wherein $R^2$ has the same meaning as $R^2$ in Formula (1-2); $Z^4$, $R^5$, b, and $X^2$ have the same meanings as those in Formula (2-2-1), respectively; and the bonding positions of —SO$_2$X$^2$ and $R^5$ on the benzene ring are the same as the bonding positions of —SO$_2$X$^2$ and $R^5$ in Formula (2-2-1), respectively;

Step (j)

A step for reacting the compound represented by Formula (2-2-3) and a compound represented by Formula (3-1) or a compound represented by Formula (3-2) to obtain the silicon compound represented by Formula (1-2):

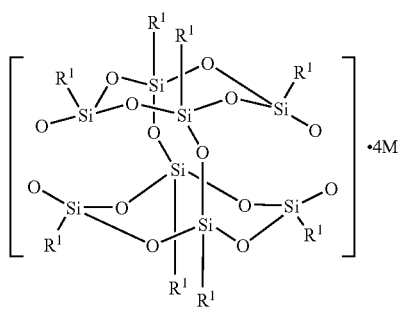
(3-1)

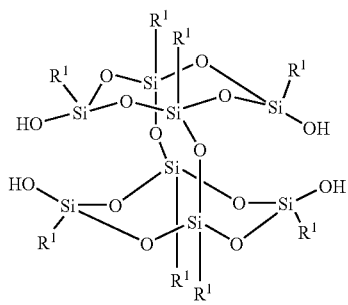
(3-2)

wherein $R^1$ has the same meaning as $R^1$ in Formula (1-2); and M is a monovalent alkali metal atom.

39. The process according to claim 38, wherein all $R^1$s are the same group selected from an alkyl having 1 to 8 carbon atoms in which arbitrary hydrogen may be replaced by fluorine and arbitrary —CH$_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

40. The process according to claim 38, wherein $R^1$ is phenyl; and $R^2$ is methyl.

41. A process for producing a silicon compound represented by Formula (1-3), characterized by carrying out the following step (k) and step (l), successively:

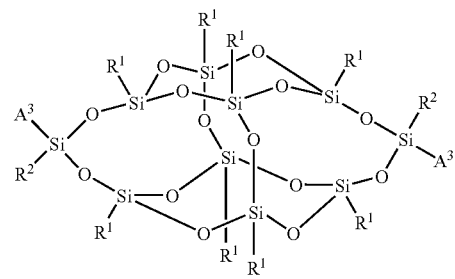
(1-3)

wherein each $R^1$ is a group independently selected from hydrogen, an alkyl having 1 to 45 carbon atoms, a substituted or unsubstituted aryl, and an arylalkyl constituted of a substituted or unsubstituted aryl group and an alkylene group; in the alkyl having 1 to 45 carbon atoms, arbitrary hydrogen may be replaced by fluorine, and arbitrary —CH$_2$— may be replaced by —O— or a cycloalkylene; in the alkylene group of the arylalkyl, arbitrary hydrogen may be replaced by fluorine, and arbitrary —CH$_2$— may be replaced by —O— or a cycloalkylene; each $R^2$ is a group independently selected from an alkyl having 1 to 8 carbon atoms, phenyl, and cyclohexyl; and $A^3$ is a group represented by Formula (2-3-1):

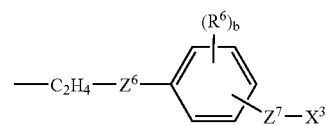
(2-3-1)

wherein $Z^6$ is a single bond or an alkylene having 1 to 8 carbon atoms in which arbitrary —CH$_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —CH$_2$— may be replaced by —O—; $X^3$ is a halogen; the bonding position of $Z^7$ on the benzene ring is a meta-position or a para-position with respect to the bonding position of $Z^6$; and the bonding position of $R^6$ is an arbitrary position excluding the respective bonding positions of $Z^6$ and $Z^7$;

Step (k)

A step for reacting a compound represented by Formula (4) and a compound represented by Formula (2-3-2) in the presence of a transition metal catalyst to obtain a compound represented by Formula (2-3-3):

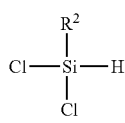
(4)

-continued (2-3-2)

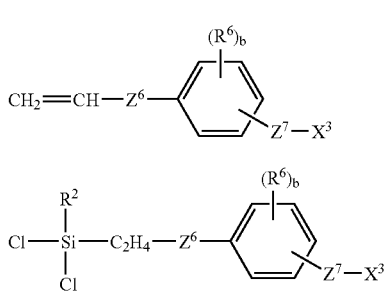

(2-3-3)

wherein $R^2$ has the same meaning as $R^2$ in Formula (1-3); $Z^6$, $R^6$, b, $Z^7$, and $X^3$ have the same meanings as those in Formula (2-3-1), respectively; and the bonding positions of $Z^7$ and $R^6$ on the benzene ring are the same as the bonding positions of $Z^7$ and $R^6$ in Formula (2-3-1), respectively;

Step (l)

A step for reacting the compound represented by Formula (2-3-3) and a compound represented by Formula (3-1) or a compound represented by Formula (3-2) to obtain the silicon compound represented by Formula (1-3):

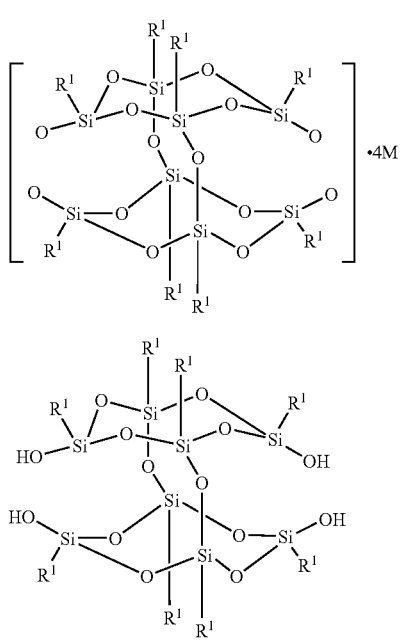

(3-1)

(3-2)

wherein $R^1$ has the same meaning as $R^1$ in Formula (1-3); and M is a monovalent alkali metal atom.

42. The process according to claim 41, wherein all $R^1$'s are the same group selected from an alkyl having 1 to 8 carbon atoms in which arbitrary hydrogen may be replaced by fluorine and arbitrary —CH$_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; when the phenyl or the phenyl group of the phenylalkyl has plural substituents, those substituents may be the same group or a different group; and each $R^2$ is a group independently selected from an alkyl having 1 to 4 carbon atoms, phenyl, and cyclohexyl.

43. The process according to claim 41, wherein $R^1$ is phenyl; and $R^2$ is methyl.

44. A polymer obtained by polymerizing an addition polymerizable monomer using the silicon compound as described in claim 1 as an initiator in the presence of a transition metal complex as a catalyst.

45. A polymer obtained by polymerizing an addition polymerizable monomer using the silicon compound as described in claim 3 as an initiator in the presence of a transition metal complex as a catalyst.

46. A polymer represented by Formula (P-1):

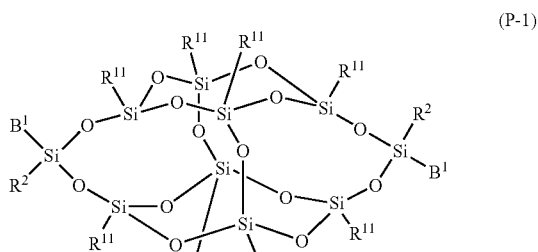

(P-1)

wherein all $R^{11}$'s are the same group selected from an alkyl having 1 to 8 carbon atoms in which arbitrary hydrogen may be replaced by fluorine and arbitrary —CH$_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —CH$_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^1$ is a group represented by Formula (2-1-P):

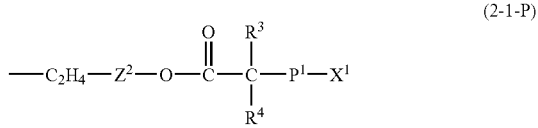

(2-1-P)

wherein $Z^2$ is an alkylene group having 1 to 18 carbon atom, and arbitrary —CH$_2$— in this alkylene may be replaced by —O—; $R^3$ is hydrogen, an alkyl having 1 to 20 carbon atoms, an aryl having 6 to 20 carbon atoms, or an arylalkyl having 7 to 20 carbon atoms; $R^4$ is an alkyl having 1 to 20 carbon atoms, an aryl having 6 to 20 carbon atoms, or an arylalkyl having 7 to 20 carbon atoms; $X^1$ is a halogen; and $P^1$ is a chain of a constitutional unit obtained by polymerization of an addition polymerizable monomer.

47. A polymer represented by Formula (P-2):

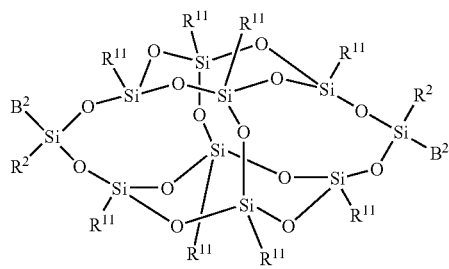

(P-2)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^2$ is a group represented by Formula (2-2-P):

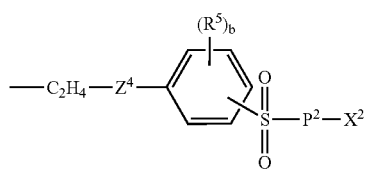

(2-2-P)

wherein $Z^4$ is a single bond or an alkylene having 1 to 8 carbon atoms in which arbitrary —$CH_2$— may be replaced by —O—, —COO—, or —OCO—; $R^5$ is an alkyl having 1 to 3 carbon atoms; b is an integer of 0 to 2; $X^2$ is a halogen; the bonding position of —$SO_2$—$P^2$—$X^2$ on the benzene ring is an ortho-position, a meta-position, or a para-position with respect to the bonding position of $Z^4$; the bonding position of $R^5$ is an arbitrary position excluding the respective bonding positions of $Z^4$ and —$SO_2$—$P^2$—$X^2$; and $P^2$ is a chain of a constitutional unit obtained by polymerization of an addition polymerizable monomer.

48. A polymer represented by Formula (P-3):

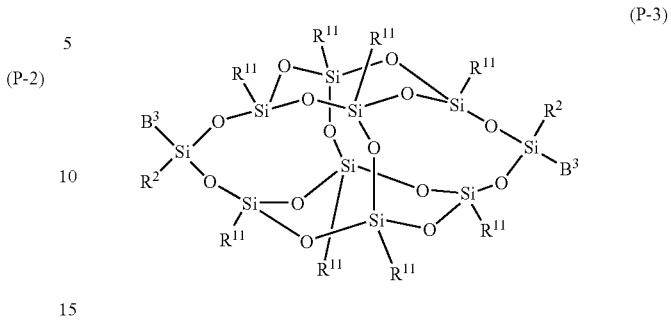

(P-3)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^3$ is a group represented by Formula (2-3-P):

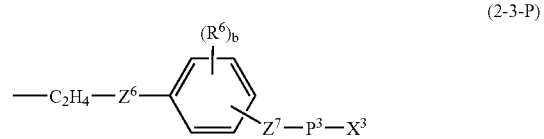

(2-3-P)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $X^3$ is a halogen; the bonding position of $Z^7$ on the benzene ring is a meta-position or a para-position with respect to the bonding position of $Z^6$; the bonding position of $R^6$ is an arbitrary position excluding the respective bonding positions of $Z^6$ and $Z^7$; and $P^3$ is a chain of a constitutional unit obtained by polymerization of an addition polymerizable monomer.

49. A polymer represented by Formula (P-4):

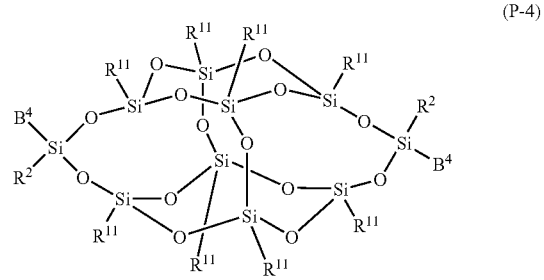

(P-4)

wherein all $R^{11}$s are the same group selected from an alkyl having 1 to 8 carbon atoms in which arbitrary hydrogen may be replaced by fluorine and arbitrary —$CH_2$— may be replaced by —O— or a cycloalkylene, phenyl in which arbitrary hydrogen may be replaced by a halogen, methyl, or methoxy, unsubstituted naphthyl, and a phenylalkyl constituted of a phenyl group in which arbitrary hydrogen may be replaced by fluorine, an alkyl having 1 to 4 carbon atoms, or methoxy and an alkylene group having 1 to 8 carbon atoms in which arbitrary —$CH_2$— may be replaced by —O— or a cycloalkylene; when the phenyl or the phenyl group of the phenylalkyl has plural substituents, those substituents may be the same group or a different group; each $R^2$ is a group independently selected from an alkyl having 1 to 4 carbon atoms, phenyl, and cyclohexyl; and $B^4$ is a group represented by Formula (2-4-P):

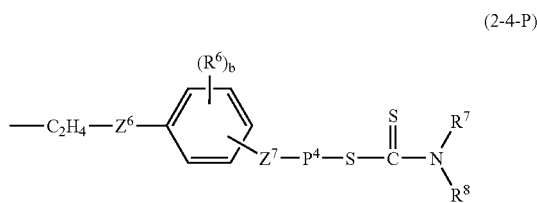

(2-4-P)

wherein $Z^6$ is a single bond or an alkylene having 1 to 8 carbon atoms in which arbitrary —$CH_2$— may be replaced by —O—, —COO—, or —OCO—; $R^6$ is an alkyl having 1 to 3 carbon atoms; b is an integer of 0 to 2; $Z^7$ is an alkylene having 1 to 3 carbon atoms in which arbitrary —$CH_2$— may be replaced by —O—; $R^7$ and $R^8$ are each independently hydrogen, an alkyl having 1 to 12 carbon atoms, a cycloalkyl having 5 to 10 carbon atoms, or an aryl having 6 to 10 carbon atoms, and $R^7$ and $R^8$ may be bound to each other to form a ring together with N; the bonding position of $Z^7$ on the benzene ring is a meta-position or a para-position with respect to the bonding position of $Z^6$; the bonding position of $R^6$ is an arbitrary position excluding the respective bonding positions of $Z^6$ and $Z^7$; and $P^4$ is a chain of a constitutional unit obtained by polymerization of an addition polymerizable monomer.

50. The polymer according to claim 46, wherein the addition polymerizable monomer is at least one member selected from (meth)acrylic acid derivatives and styrene derivatives.

51. The polymer according to claim 47, wherein the addition polymerizable monomer is at least one member selected from a (meth)acrylic acid derivative and a styrene derivative.

52. The polymer according to claim 48, wherein the addition polymerizable monomer is at least one member selected from a (meth)acrylic acid derivative and a styrene derivative.

53. The polymer according to claim 49, wherein the addition polymerizable monomer is at least one member selected from (meth)acrylic acid derivatives and styrene derivatives.

* * * * *